(12) United States Patent
Gambale et al.

(10) Patent No.: US 7,993,368 B2
(45) Date of Patent: Aug. 9, 2011

(54) SUTURE CLIPS, DELIVERY DEVICES AND METHODS

(75) Inventors: Richard A. Gambale, Tyngsboro, MA (US); Michael F. Weiser, Groton, MA (US); Edward Carlton Page, Baldwinville, MA (US); Alexander Kolnick, Marblehead, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 874 days.

(21) Appl. No.: 10/220,413

(22) PCT Filed: Mar. 5, 2001

(86) PCT No.: PCT/US01/07349
§ 371 (c)(1),
(2), (4) Date: Mar. 13, 2003

(87) PCT Pub. No.: WO01/66001
PCT Pub. Date: Sep. 13, 2001

(65) Prior Publication Data
US 2003/0167062 A1    Sep. 4, 2003

Related U.S. Application Data

(60) Provisional application No. 60/186,926, filed on Mar. 3, 2000, provisional application No. 60/205,741, filed on May 19, 2000, provisional application No. 60/205,444, filed on May 19, 2000, provisional application No. 60/253,970, filed on Nov. 29, 2000.

(51) Int. Cl.
*A61B 17/04* (2006.01)
*A44B 17/00* (2006.01)

(52) U.S. Cl. .................................. 606/232; 24/136 R
(58) Field of Classification Search ............... 606/232, 606/139, 144, 142, 151, 157–158; 24/136 R, 24/136 K, 136 L
See application file for complete search history.

(56) References Cited

U.S. PATENT DOCUMENTS

| 453,508 A | 6/1891 | Ruby |
| 730,152 A | 6/1903 | Pitner |
| 979,342 A | 12/1910 | Schaefer |

(Continued)

FOREIGN PATENT DOCUMENTS
DE         3909999 A1     9/1990
(Continued)

OTHER PUBLICATIONS

Bard Interventional Products Division, C. R. Bard, Inc., "RapidFire™ Multiple Band Ligator—Information for Use", No. AE1904601/01, Issued Jun. 1996.

(Continued)

*Primary Examiner* — Eduardo C Robert
*Assistant Examiner* — Diane Yabut
(74) *Attorney, Agent, or Firm* — Wolf, Greenfield & Sacks, P.C.

(57) ABSTRACT

Provided herein are suture clips that include a plug, a ring, and a shaft. Also provided is a catheter that includes a collet cage with a plurality of flexible collet fingers that engage a suture clip ring and a suture clip plug for assembly with a suture. The catheter is designed to hold and assemble the suture clip in a first position and release the suture clip and sever the suture ends proximal to the suture clip in a second position.

12 Claims, 91 Drawing Sheets

U.S. PATENT DOCUMENTS

| | | | |
|---|---|---|---|
| 1,325,699 A | 12/1919 | Oesterhaus | |
| 1,389,859 A * | 9/1921 | Chronister | 24/136 L |
| 1,868,308 A | 7/1932 | Brumfield | |
| 2,170,599 A | 8/1939 | Stricklen | |
| 2,443,155 A * | 6/1948 | Zahutnik | 403/211 |
| 2,587,364 A | 2/1952 | Mitchell | |
| 2,601,852 A | 7/1952 | Wendt | |
| 2,621,655 A | 12/1952 | Olson | |
| 2,650,593 A | 9/1953 | Weil et al. | |
| 2,880,728 A | 4/1959 | Rights | |
| 3,013,559 A | 12/1961 | Thomas | |
| 3,048,908 A * | 8/1962 | Bryan | 403/202 |
| 3,238,941 A | 3/1966 | Klein et al. | |
| 3,470,875 A | 10/1969 | Johnson | |
| 3,716,058 A | 2/1973 | Tanner | |
| 3,757,781 A | 9/1973 | Smart | |
| 3,760,810 A | 9/1973 | Hoorn | |
| 3,766,610 A * | 10/1973 | Thorsbakken | 403/211 |
| 3,845,772 A | 11/1974 | Smith | |
| 3,858,571 A | 1/1975 | Rudolph | |
| 4,126,124 A | 11/1978 | Miller | |
| 4,144,876 A | 3/1979 | Deleo | |
| 4,164,225 A | 8/1979 | Johnson et al. | |
| 4,210,148 A | 7/1980 | Stivala | |
| 4,216,777 A | 8/1980 | Pridemore | |
| 4,226,239 A | 10/1980 | Polk et al. | |
| 4,234,111 A | 11/1980 | Dischinger | |
| 4,236,470 A | 12/1980 | Stenson | |
| 4,291,698 A | 9/1981 | Fuchs et al. | |
| 4,345,601 A | 8/1982 | Fukunda | |
| 4,414,908 A | 11/1983 | Eguchi et al. | |
| 4,415,092 A | 11/1983 | Boyer | |
| 4,440,171 A | 4/1984 | Nomoto et al. | |
| 4,469,101 A | 9/1984 | Coleman et al. | |
| 4,474,174 A | 10/1984 | Petruzzi | |
| 4,493,319 A | 1/1985 | Polk et al. | |
| D279,504 S | 7/1985 | Tump | |
| 4,597,390 A | 7/1986 | Mulhollan et al. | |
| 4,607,620 A | 8/1986 | Storz | |
| 4,615,472 A | 10/1986 | Nash | |
| 4,621,640 A | 11/1986 | Mulhollan et al. | |
| 4,637,816 A | 1/1987 | Mann | |
| 4,665,906 A | 5/1987 | Jervis | |
| 4,672,979 A | 6/1987 | Pohndorf | |
| 4,706,653 A | 11/1987 | Yamamoto | |
| 4,721,103 A | 1/1988 | Freedland | |
| 4,735,194 A | 4/1988 | Stiegmann | |
| 4,738,255 A | 4/1988 | Goble et al. | |
| 4,741,330 A | 5/1988 | Hayhurst | |
| 4,759,364 A | 7/1988 | Boebel | |
| 4,794,911 A | 1/1989 | Okada | |
| 4,825,259 A | 4/1989 | Berry, Jr. | |
| 4,841,888 A | 6/1989 | Mills et al. | |
| 4,860,746 A | 8/1989 | Yoon | |
| 4,890,615 A | 1/1990 | Caspari et al. | |
| 4,898,156 A | 2/1990 | Gatturna et al. | |
| 4,899,743 A | 2/1990 | Nicholson et al. | |
| 4,923,461 A | 5/1990 | Caspari et al. | |
| 4,927,428 A | 5/1990 | Richards | |
| 4,932,962 A | 6/1990 | Yoon et al. | |
| 4,936,823 A | 6/1990 | Colvin et al. | |
| 4,946,468 A | 8/1990 | Li | |
| 4,950,285 A | 8/1990 | Wilk | |
| 4,968,315 A | 11/1990 | Gatturna | |
| 5,002,042 A | 3/1991 | Okada | |
| 5,002,550 A | 3/1991 | Li | |
| 5,037,021 A | 8/1991 | Mills et al. | |
| 5,037,422 A | 8/1991 | Hayhurst et al. | |
| 5,041,129 A | 8/1991 | Hayhurst et al. | |
| 5,046,513 A | 9/1991 | Gatturna et al. | |
| 5,078,731 A | 1/1992 | Hayhurst | |
| 5,080,663 A | 1/1992 | Mills et al. | |
| 5,100,417 A | 3/1992 | Cerier et al. | |
| 5,100,418 A | 3/1992 | Yoon et al. | |
| 5,100,421 A | 3/1992 | Christoudias | |
| 5,102,421 A | 4/1992 | Anspach et al. | |
| 5,116,349 A | 5/1992 | Aranyi | |
| 5,123,913 A | 6/1992 | Wilk et al. | |
| 5,125,553 A | 6/1992 | Oddsen et al. | |
| 5,147,379 A | 9/1992 | Sabbaghian et al. | |
| 5,152,769 A | 10/1992 | Baber | |
| 5,163,945 A | 11/1992 | Ortiz et al. | |
| 5,171,251 A | 12/1992 | Bregen et al. | |
| 5,176,682 A | 1/1993 | Chow | |
| 5,193,525 A | 3/1993 | Silverstein et al. | |
| 5,199,566 A | 4/1993 | Ortiz et al. | |
| 5,203,863 A | 4/1993 | Bidoia | |
| 5,207,679 A | 5/1993 | Li | |
| 5,207,690 A | 5/1993 | Rohrabacher | |
| 5,207,694 A | 5/1993 | Broome | |
| 5,211,650 A | 5/1993 | Noda | |
| 5,213,093 A | 5/1993 | Swindle | |
| 5,217,486 A | 6/1993 | Rice et al. | |
| 5,220,928 A | 6/1993 | Oddsen | |
| 5,224,946 A | 7/1993 | Hayhurst et al. | |
| 5,236,445 A | 8/1993 | Hayhurst et al. | |
| 5,242,431 A | 9/1993 | Kristiansen | |
| 5,254,126 A | 10/1993 | Filipi et al. | |
| 5,258,015 A | 11/1993 | Li et al. | |
| 5,258,016 A | 11/1993 | Dipoto et al. | |
| 5,259,366 A | 11/1993 | Reydel et al. | |
| 5,268,001 A | 12/1993 | Nicholson et al. | |
| 5,269,789 A | 12/1993 | Chin et al. | |
| 5,269,809 A | 12/1993 | Hayhurst et al. | |
| 5,273,053 A | 12/1993 | Pohndorf | |
| 5,281,236 A | 1/1994 | Bagnato et al. | |
| 5,281,237 A | 1/1994 | Gimpelson | |
| 5,282,832 A | 2/1994 | Toso et al. | |
| 5,284,485 A | 2/1994 | Kammerer et al. | |
| 5,290,296 A | 3/1994 | Phillips | |
| 5,290,297 A | 3/1994 | Phillips | |
| 5,297,536 A | 3/1994 | Wilk | |
| 5,304,184 A | 4/1994 | Hathaway et al. | |
| 5,306,280 A | 4/1994 | Bregen et al. | |
| 5,306,309 A | 4/1994 | Wagner et al. | |
| 5,312,438 A | 5/1994 | Johnson | |
| 5,320,630 A | 6/1994 | Ahmed | |
| 5,324,308 A | 6/1994 | Pierce | |
| 5,330,442 A | 7/1994 | Green et al. | |
| 5,330,486 A | 7/1994 | Wilk | |
| 5,333,624 A | 8/1994 | Tovey | |
| 5,334,200 A | 8/1994 | Johnson | |
| 5,336,229 A | 8/1994 | Nods | |
| 5,344,060 A | 9/1994 | Gravener et al. | |
| 5,354,298 A | 10/1994 | Lee et al. | |
| 5,356,413 A | 10/1994 | Martins et al. | |
| 5,356,416 A | 10/1994 | Chu et al. | |
| 5,364,407 A | 11/1994 | Poll | |
| 5,364,408 A | 11/1994 | Gordon | |
| 5,368,599 A | 11/1994 | Hirsch et al. | |
| 5,368,601 A | 11/1994 | Sauer et al. | |
| 5,370,662 A | 12/1994 | Stone et al. | |
| 5,372,599 A | 12/1994 | Martins | |
| 5,372,604 A | 12/1994 | Trott | |
| 5,376,101 A | 12/1994 | Green et al. | |
| 5,380,334 A | 1/1995 | Torrie et al. | |
| 5,383,905 A | 1/1995 | Golds et al. | |
| 5,389,103 A | 2/1995 | Melzer et al. | |
| 5,391,173 A | 2/1995 | Wilk | |
| 5,391,176 A | 2/1995 | Torre | |
| 5,391,182 A | 2/1995 | Chin | |
| 5,398,844 A | 3/1995 | Zaslavsky et al. | |
| 5,403,346 A | 4/1995 | Loeser | |
| 5,403,348 A | 4/1995 | Bonutti | |
| 5,405,354 A | 4/1995 | Sarrett | |
| 5,405,359 A | 4/1995 | Pierce | |
| 5,409,499 A | 4/1995 | Yi | |
| 5,411,506 A | 5/1995 | Golbe et al. | |
| 5,411,522 A | 5/1995 | Trott | |
| 5,411,523 A | 5/1995 | Goble | |
| 5,413,585 A | 5/1995 | Pagedasa | |
| 5,417,691 A | 5/1995 | Hayhurst | |
| 5,417,697 A | 5/1995 | Wilk et al. | |
| 5,417,699 A | 5/1995 | Klein et al. | |
| 5,423,834 A | 6/1995 | Ahmed | |
| 5,423,860 A | 6/1995 | Lizardi et al. | |
| 5,431,639 A | 7/1995 | Shaw | |

| | | | | | | |
|---|---|---|---|---|---|---|
| 5,431,666 A | 7/1995 | Sauer et al. | 5,899,921 A | | 5/1999 | Caspari et al. |
| 5,433,722 A | 7/1995 | Sharpe et al. | 5,902,321 A | * | 5/1999 | Caspari et al. ............... 606/232 |
| 5,437,680 A | 8/1995 | Yoon | 5,910,105 A | | 6/1999 | Swain et al. |
| 5,439,467 A | 8/1995 | Benderev et al. | 5,919,208 A | | 7/1999 | Valenti |
| 5,443,482 A | 8/1995 | Stone et al. | RE36,289 E | | 8/1999 | Le et al. |
| 5,445,167 A | 8/1995 | Yoon et al. | 5,931,844 A | | 8/1999 | Thompson et al. |
| 5,447,512 A | 9/1995 | Wilson et al. | 5,935,149 A | | 8/1999 | Ek |
| 5,458,608 A | 10/1995 | Wortrich | 5,938,586 A | | 8/1999 | Wilk et al. |
| 5,462,558 A | 10/1995 | Kolesa et al. | 5,947,983 A | | 9/1999 | Solar et al. |
| 5,462,559 A | 10/1995 | Ahmed | 5,972,001 A | | 10/1999 | Yoon |
| 5,462,561 A | 10/1995 | Voda | 5,984,917 A | | 11/1999 | Fleischman et al. |
| 5,464,426 A | 11/1995 | Bonutti | 5,997,556 A | | 12/1999 | Tanner |
| 5,466,241 A | 11/1995 | Leroy et al. | 6,001,110 A | | 12/1999 | Adams |
| 5,470,337 A | 11/1995 | Moss | 6,007,551 A | | 12/1999 | Peifer et al. |
| 5,474,572 A | 12/1995 | Hayhurst | 6,010,515 A | | 1/2000 | Swain et al. |
| 5,474,573 A | 12/1995 | Hatcher | 6,010,525 A | | 1/2000 | Bonutti et al. |
| 5,478,353 A | 12/1995 | Yoon | 6,015,428 A | | 1/2000 | Pagedas |
| 5,487,746 A | 1/1996 | Yu et al. | 6,024,755 A | | 2/2000 | Addis |
| 5,507,754 A | 4/1996 | Green et al. | 6,059,719 A | | 5/2000 | Yamamoto et al. |
| 5,507,758 A | 4/1996 | Thomason et al. | 6,059,798 A | | 5/2000 | Tolkoff |
| 5,507,797 A | 4/1996 | Suzuki et al. | 6,066,160 A | | 5/2000 | Colvin et al. |
| 5,514,159 A | 5/1996 | Matula et al. | 6,071,233 A | | 6/2000 | Ishikawa et al. |
| 5,520,700 A | 5/1996 | Beyar et al. | 6,071,292 A | | 6/2000 | Makower et al. |
| 5,520,702 A | 5/1996 | Saur et al. | 6,074,401 A | | 6/2000 | Gardiner et al. |
| 5,520,703 A | 5/1996 | Essig et al. | 6,086,600 A | | 7/2000 | Kortenbach |
| 5,527,318 A | 6/1996 | McGarry | 6,086,608 A | * | 7/2000 | Ek et al. ............... 606/232 |
| 5,531,763 A | 7/1996 | Mastri et al. | 6,099,535 A | | 8/2000 | Lamport et al. |
| 5,542,432 A | 8/1996 | Slater | 6,126,677 A | * | 10/2000 | Ganaja et al. ............... 606/232 |
| 5,545,170 A | 8/1996 | Hart | 6,129,661 A | | 10/2000 | Iafrati et al. |
| 5,545,180 A | 8/1996 | Le et al. | 6,136,009 A | | 10/2000 | Mears |
| 5,549,617 A | 8/1996 | Green et al. | 6,149,658 A | | 11/2000 | Gardiner et al. |
| 5,562,686 A | 10/1996 | Sauer et al. | 6,159,234 A | * | 12/2000 | Bonutti et al. ............... 606/232 |
| 5,562,689 A | 10/1996 | Green et al. | 6,200,329 B1 | | 3/2001 | Fung et al. |
| 5,569,274 A | 10/1996 | Rapacki et al. | 6,241,140 B1 | | 6/2001 | Adams et al. |
| 5,569,305 A | 10/1996 | Bonutti | 6,280,452 B1 | | 8/2001 | Mears |
| 5,584,835 A | 12/1996 | Greenfield | 6,358,259 B1 | | 3/2002 | Swain et al. |
| 5,584,861 A | 12/1996 | Swain et al. | 6,436,108 B1 | | 8/2002 | Mears |
| 5,584,862 A | 12/1996 | Bonutti | 6,514,265 B2 | | 2/2003 | Ho et al. |
| 5,591,177 A | 1/1997 | Lehrer | 6,551,332 B1 | | 4/2003 | Nguyen et al. |
| 5,591,180 A | 1/1997 | Hinchliffe | 6,607,541 B1 | | 8/2003 | Gardiner et al. |
| 5,601,530 A | 2/1997 | Nielsen et al. | 6,629,630 B2 | | 10/2003 | Adams |
| 5,601,571 A | 2/1997 | Moss | 6,689,130 B2 | | 2/2004 | Arai et al. |
| 5,609,597 A | 3/1997 | Lehrer | 6,719,763 B2 | | 4/2004 | Chung et al. |
| 5,618,314 A | 4/1997 | Harwin et al. | 6,736,828 B1 | | 5/2004 | Adams et al. |
| 5,624,453 A | 4/1997 | Ahmed | 2002/0177847 A1 | | 11/2002 | Long et al. |
| 5,626,590 A | 5/1997 | Wilk | 2003/0171651 A1 | | 9/2003 | Page et al. |
| 5,630,824 A | 5/1997 | Hart | 2003/0171760 A1 | | 9/2003 | Gambale et al. |
| 5,645,553 A | 7/1997 | Kolesa et al. | 2003/0176880 A1 | | 9/2003 | Long et al. |
| 5,658,313 A | 8/1997 | Thal et al. | 2003/0208209 A1 | | 11/2003 | Gambale et al. |
| 5,665,109 A | 9/1997 | Yoon | 2004/0034371 A1 | | 2/2004 | Lehman et al. |
| 5,665,112 A | 9/1997 | Thal | 2004/0138704 A1 | | 7/2004 | Gambale et al. |
| 5,681,328 A | 10/1997 | Lamport et al. | 2004/0158125 A1 | | 8/2004 | Aznoian et al. |
| 5,681,351 A | 10/1997 | Jamiolkowski et al. | 2005/0033319 A1 | | 2/2005 | Gambale et al. |
| 5,683,417 A | 11/1997 | Cooper | | | | |
| 5,683,419 A | 11/1997 | Thal | | | | |

FOREIGN PATENT DOCUMENTS

| | | |
|---|---|---|
| EP | 0591991 A2 | 4/1994 |
| EP | 0598219 A2 | 5/1994 |
| GB | 2165559 | 4/1986 |
| JP | 7-136177 | 5/1995 |
| WO | 95/32670 A1 | 12/1995 |
| WO | WO 96/09796 | 4/1996 |
| WO | WO 96/20647 | 7/1996 |
| WO | WO 97/30639 | 8/1997 |
| WO | 99/04699 A1 | 2/1999 |
| WO | WO 99/04698 | 2/1999 |
| WO | WO99/22650 | 5/1999 |
| WO | WO 01/66018 | 9/2001 |
| WO | WO 01/87144 | 11/2001 |
| WO | WO 01/89370 | 11/2001 |
| WO | WO 01/89393 | 11/2001 |

OTHER PUBLICATIONS

Cook® Wilson-Cook Medical GI Endoscopy, Sales Literature, www.wilsoncook.com.

Filipi, Transoral, Flexible Endoscopic Suturing for Treatment of GERD: A Multicenter Trial, *Gastrointest Endosc* Apr. 2001; 53 (4): 416-422.

Lehman et al., "Endoscopic Gastroesophageal Suturing: Does Addition of Cautery Aid Plication Persistence?" *Digestive Disease Week* Poster Board Presentation—May 2000, On-line Abstract Feb. 2000.

Martinez-Serna et al., Endoscopic Valvuloplasty for GERD, *Gastrointest Endosc* Nov. 2000; 52 (5): 663-70.

Sherman et al., "Efficacy of Endoscopic Sphincterotomy and Surgical Sphincteroplasty for Patients with Sphincter of Oddi Dysfunction: Randomized, Prospective Study", *Gastrointest Endosc*, vol. 37, No. 2, 1991, p. 249 (Abstract).

Sherman et al., "Endoscopic Sphincterotomy Induced Hemorrhage: Treatment with Multipolar Electrocoagulation", *Gastrointest Endosc*, vol. 37, No. 2, 1991, p. 249 (Abstract).

Supplementary Partial European Search Report for European Application No. EP 01918427.4, dated Apr. 22, 2008.

Extended European Search Report for European Patent Application 10 18 0078, dated Dec. 17, 2010 (8 pages).

* cited by examiner

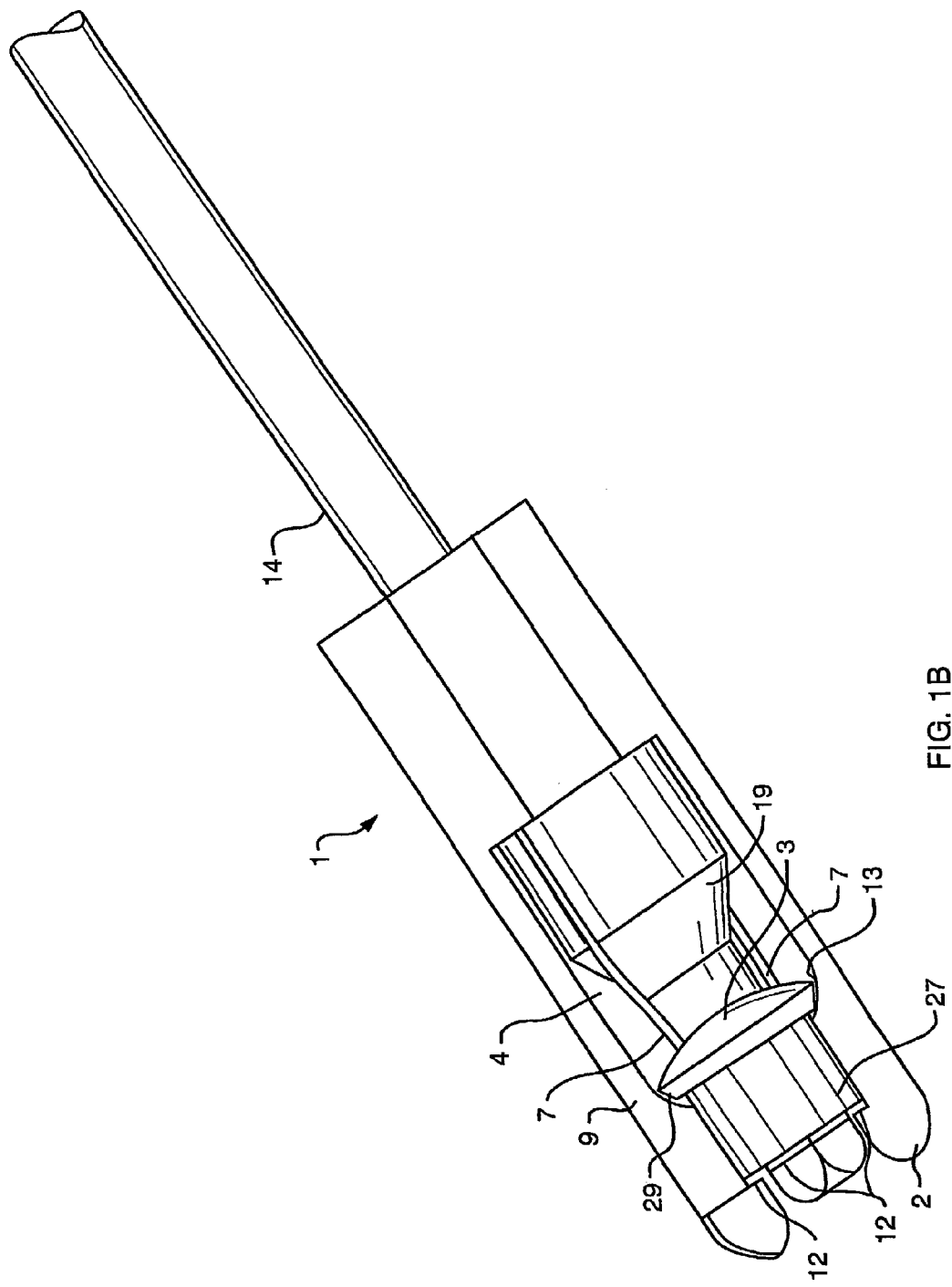

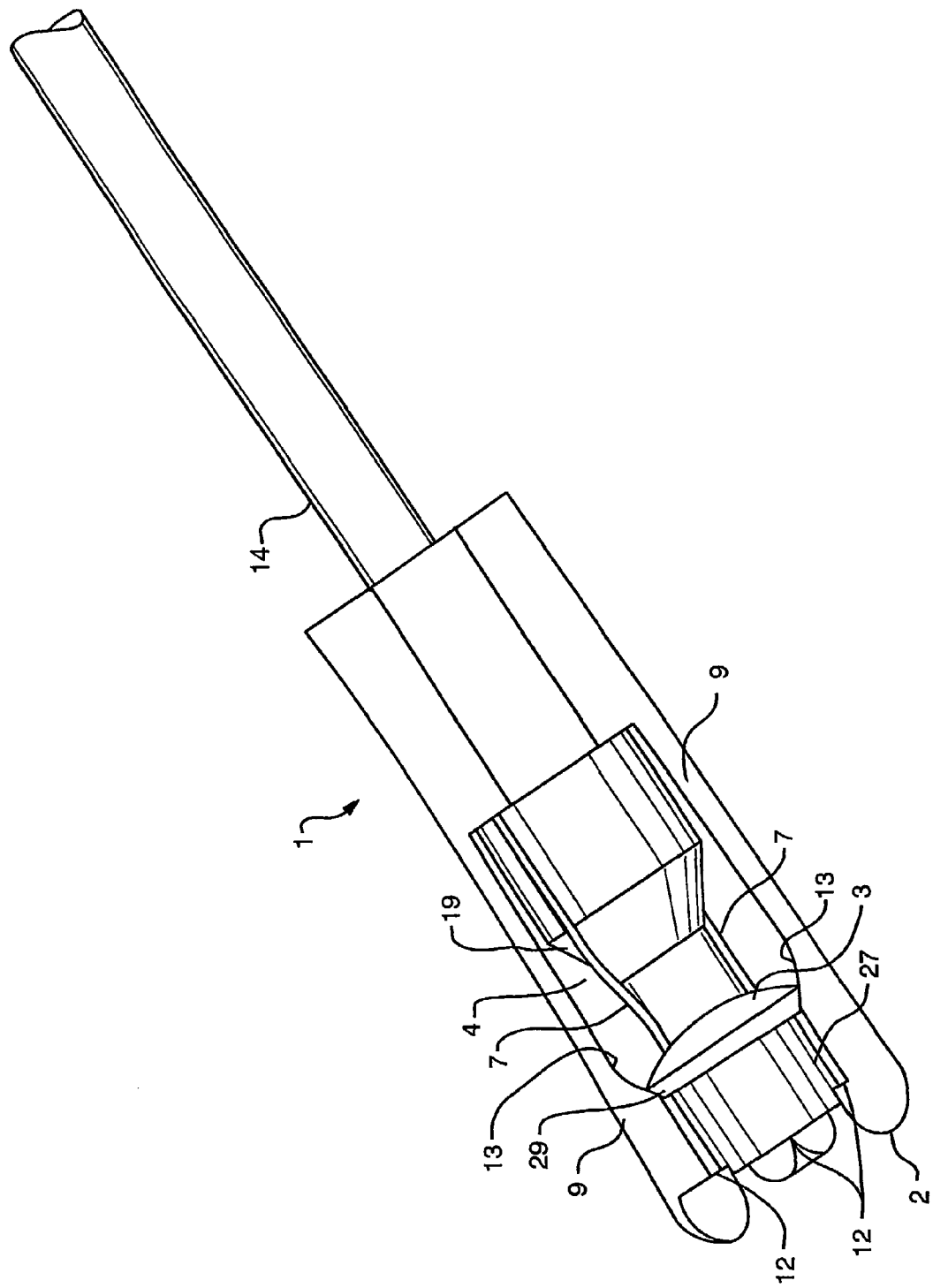

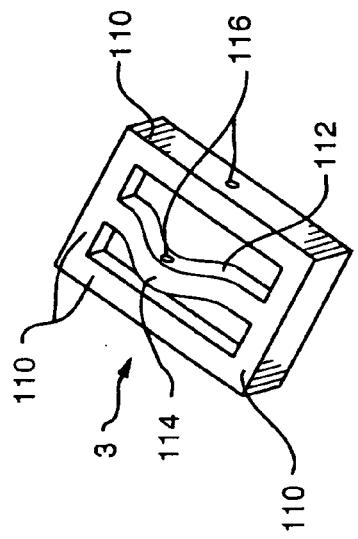
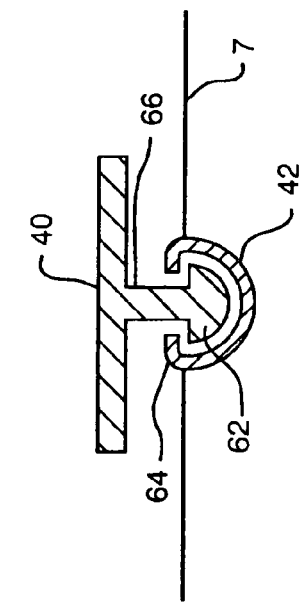
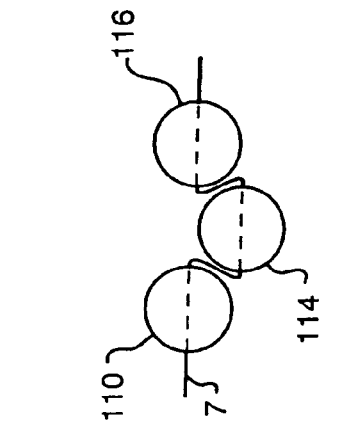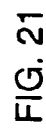
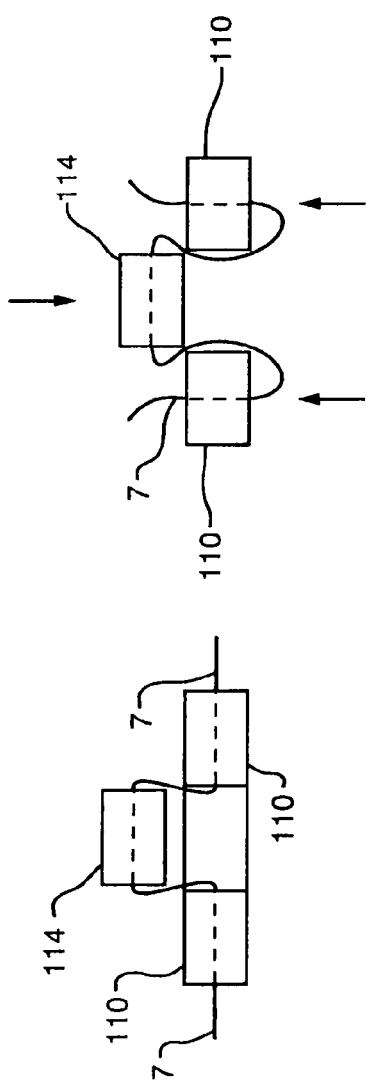

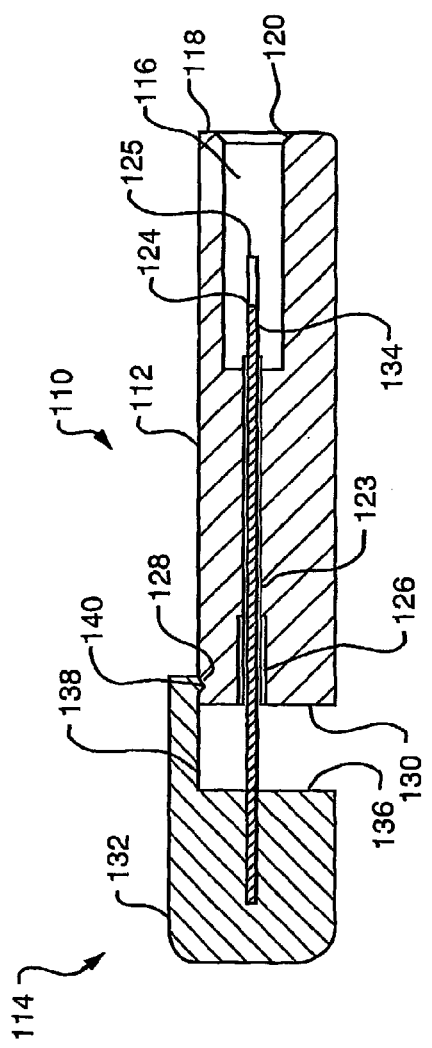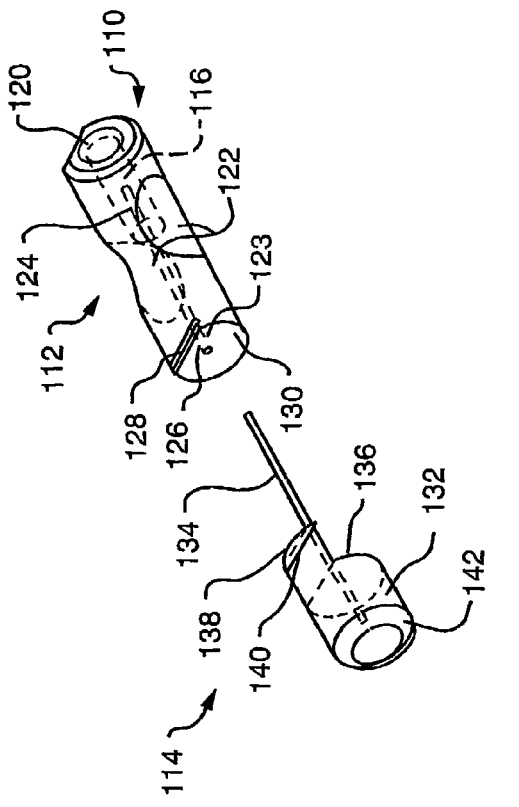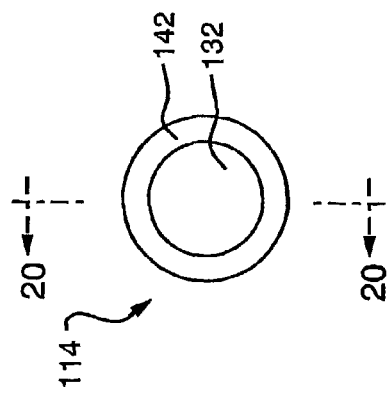
FIG. 154
FIG. 155
FIG. 156

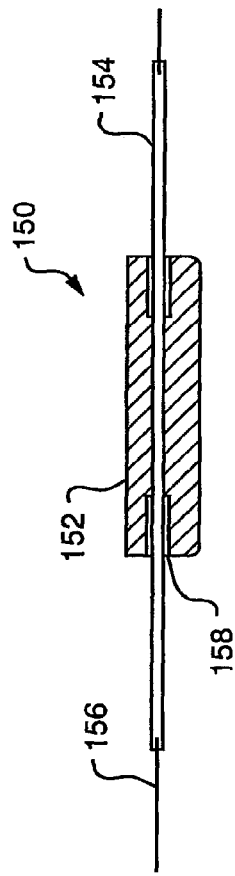
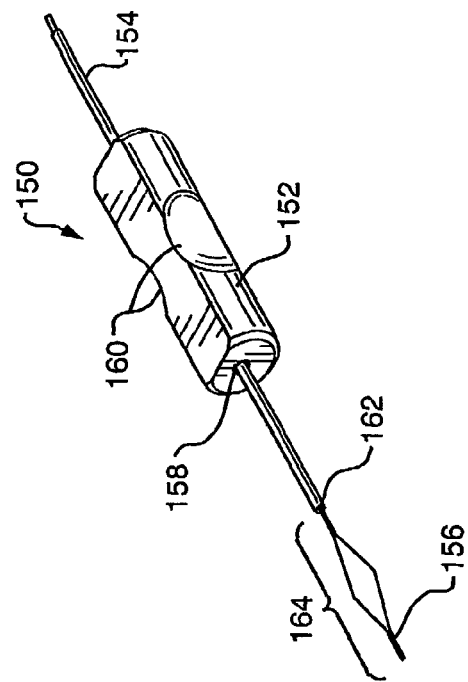
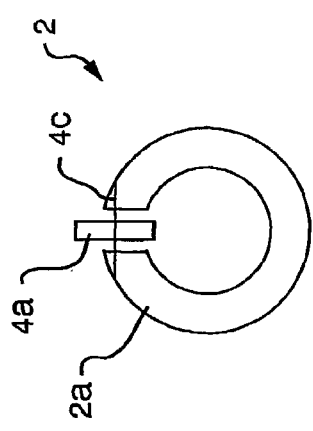
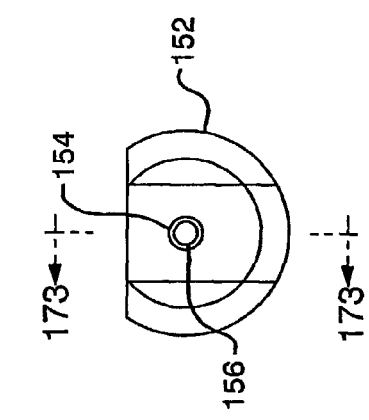
FIG. 172
FIG. 173
FIG. 174
FIG. 175

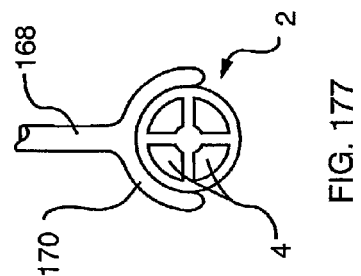
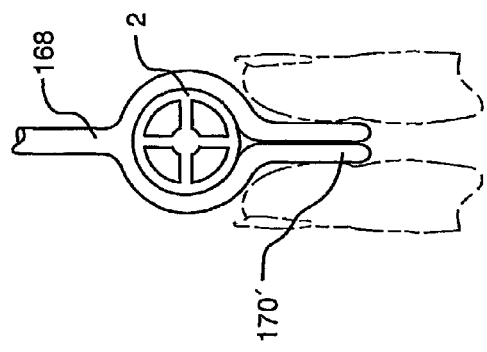
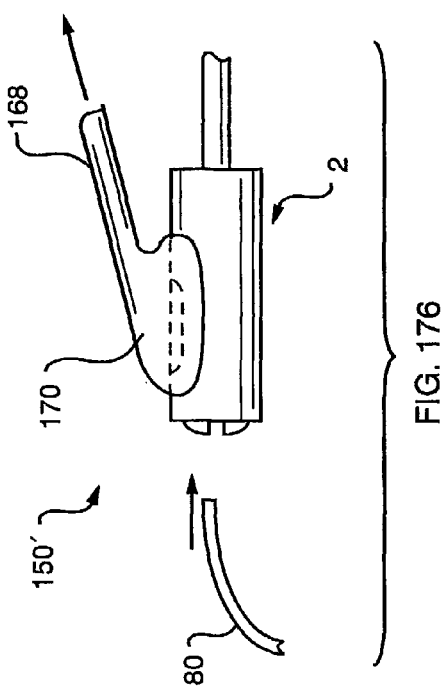
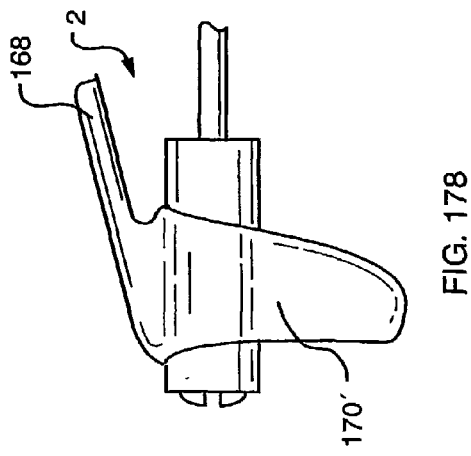

SUTURE CLIPS, DELIVERY DEVICES AND METHODS

CROSS REFERENCE TO RELATED APPLICATIONS

This application is the U.S. National Stage of International Application No. PCT/US01/07349, filed on Mar. 5, 2001, and published in English, which claims the benefit of U.S. Provisional Application No. 60/186,926, filed on Mar. 3, 2000, U.S. Provisional Application No. 60/205,741, filed on May 19, 2000, U.S. Provisional Application No. 60/205,444, filed on May 19, 2000, and U.S. Provisional Application No. 60/253,970, filed on Nov. 29, 2000. The entire disclosure of the above applications are incorporated herein by reference.

FIELD OF THE INVENTION

The disclosed invention relates generally to devices used to secure sutures. More particularly, the invention relates to suture clips and suture clip delivery devices used in conjunction with sewing devices used in flexible endoscopy; though it is also applicable to devices used in rigid endoscopy.

BACKGROUND OF THE INVENTION

It is estimated that as many as 15,000,000 individuals in the United States suffer from stomach acid reflux into the lower esophageal region, commonly referred to as GERD (gastroesophageal reflux disorder). Although the illness may result from a wide variety of causes, it is ultimately the failure of the cardiac sphincter located above the stomach that enables a reflux event to occur. A surgical method developed to reduce reflux episodes involves forming tissue folds in the walls of the stomach to reduce the cross-sectional area of the gastroesophageal juncture to mimic the function of the cardiac sphincter. To perform these types of procedures, sewing devices used to suture the stomach wall into folds are used. The procedure typically involves a fiber optic endoscope introduced into the lower esophageal area. A sewing instrument is advanced down the working channel of the endoscope that has an aspiration port for generating negative pressure to suction stomach wall tissue into the sewing instrument where one or more sutures are implanted to hold the suctioned tissue in a folded condition known as a plication.

Sewing devices for this procedure are described in, for example, GB-A-2165559 and U.S. Pat. Ser. No. 5,080,663. According to these references, a sewing device is used for passing a thread through a tissue fold. The sewing device comprises a hollow needle movable between a first pre-tissue penetration position and a second position in which it passes through the tissue, with a thread carrier adapted to be attached to the thread and being receivable within the hollow needle.

Preferably, the sewing device comprises a body that defines a cavity within which the substrate portion can be held, for example, by means of suction. The hollow needle is mounted for movement in the body between the first and second positions. In some versions of the procedure, a suture is inserted into the tissue with a needle, the two ends of which are fed back out of the patient. Typically, a physician fashions a series of half hitches to secure the suture to the subject tissue.

In other embodiments of the procedure, a tag attached to a distal end of the suture and contained within a lumen of the needle is inserted into and past the tissue. With the needle in an advanced position, i.e., with the needle distal tip extending distally beyond the pierced tissue, a pusher forces the tag out of the needle. After retraction of the needle from the tissue, the suture is retracted so that the tag contacts the tissue. The tag functions as an anchor that enables the suture to be secured to the tissue from the proximal end and also disperses the force applied to the tissue by the suture to prevent tearing of the tissue. Such a device and procedure is described in U.S. Pat. Ser. No. 5,080,663 to Mills et al., the contents of which are incorporated herein by reference.

One of the significant problems associated with these procedures is the time and number of intubations needed to perform the various procedures endoscopically. Due to a number of concerns, a patient is typically anesthetized for no more than approximately 40 minutes. In this period of time, procedures such as the GERD procedure must be performed to completion. In the GERD procedure, several intubations are performed to create several plications. As many as nine intubations are required to create just one plication. This is the case when half hitches are used to secure the suture. Each half hitch requires the hitch to be made outside the endoscope and then advanced down the endoscope with a pusher. Typically, six half hitches are used per suture thus six intubations are needed to secure the half hitches. The time needed for each intubation substantially reduces the working time to complete a GERD procedure.

One approach to solving this problem is disclosed in U.S. Ser. Pat. No. 5,584,861 to Swain. The Swain patent discloses a suture clip and suture clip delivery device that is used in place of half hitch knots. The disclosed suture clip is a cylinder with a plug that can be releasably secured in the cylinder. The disclosed suture clip delivery device includes a tube, the distal end of which has a recess for receiving the suture clip. An axially movable stirrup is provided at the distal end that has the capacity to be moved from a first position that secures the suture clip to the tube and a second position that allows for the suture clip to be removed from the recess.

An aperture is provided in the cylinder to receive the suture. The cylinder is advanced over the suture that exits from a proximal end of the cylinder and enters the tube. An aperture in a sidewall of the tube provides egress for the suture. The plug is then advanced down the tube and into the cylinder. The interfacing walls of the cylinder and plug capture the suture. A pusher is used to force the plug into the cylinder while the stirrup maintains the suture clip in the recess. Following plug insertion, the stirrup, which is offset from the center axis of the tube, is advanced distally from the distal end of the tube to release the suture clip from the tube.

Although the Swain device solves the problem of multiple half hitches, the overall design of the device has certain drawbacks. First, to successfully join the cylinder to the plug to form the suture clip, the stirrup must be physically maintained in a retracted position while an opposing force is applied with a pusher to the plug. Second, the presence of the stirrup inevitably prevents the tube and therefore, the suture clip from being placed tight against the sutured tissue. This opens the possibility for slack to develop between the clip and the tissue, which can potentially lead to a relaxation of the desired tissue fold.

Suture anchors or clips and the means to deliver and secure them are quite common in the medical industry as they play a significant role in simplifying the tedious task of securing tissue previously accomplished by tying knots on sutures. Quite common are metallic twist tie, staples and various forms of plastic or metallic permanent or temporary mechanical means to prevent the suture from slipping through the tissue. As a result of their function, the clips are typically designed to be large to overcome the stresses expected of them. Disclosed are several single and multi-component suture clips as well as a variety of relatively simple compact suture clip delivery devices that can be inserted into a natural body orifice or through the working channel of an endoscope to cinch a suture clip into the desired position in close proximity to or against the plication.

It is to be appreciated that the suture clips and suture clip delivery devices disclosed herein have a potentially wide range of applications including, but not limited to, the attachment of devices, e.g., pH monitor to the gastrointestinal wall, the closure of perforations or ulcers and the creation of anastomoses. Another useful application involves the use of radiopaque clips as fluoroscopic markers.

It is an object of the invention to provide a variety of suture clip designs that effectively disburse the forces applied to sutured tissue to prevent tearing. It is a further object of the invention to provide a suture clip delivery device that eliminates the need to manually apply opposing forces to construct a suture clip. Another object of the invention is to provide a suture clip delivery device that enables the user to place the clip tight against the sutured tissue to eliminate or at least minimize any slack development in the suture. A further object is to provide a suture-severing device that severs suture ends proximal to the suture clip. A still further object is to reduce the number of steps needed to assemble and cinch a suture clip and sever the excess suture material. These and other objects of the invention will become apparent from a reading of the following sections.

SUMMARY OF THE INVENTION

One of the suture clip delivery and locking systems described herein includes a tool designed to be attached to the distal end of an endoscope or catheter among other possibilities. The tool has a body from which finger-like segments project distally. The finger-like projections are made of a material that allows the finger-like projections to flex or spring from a first closed position to a second open position and back to the first position. The finger-like projections define a chamber within which a suture clip is premounted or introduced by being advanced through the endoscope or catheter. The chamber is defined axially at a distal end by tangs extending radially inwardly from the distal ends of the finger-like projections and at a proximal end by proximal tangs or cam followers that extend radially inwardly from inner walls of the finger-like projections. A pusher, adapted to slide within the tool's body, is provided having a head that is adapted to mate with the cam follower to move the finger-like projections to the second open position when the pusher is advanced distally in and through the endoscope or catheter.

The suture clips described herein are designed to allow the suture to interwind through the clips in such a manner that the clips move with minimal friction while in an open position. In a closed position, the clip captures the suture, by the increased friction. The suture passes proximally through the chamber between the pusher head and mating tang and then outward through a lumen in the chamber and continues proximally outside the endoscope or catheter to the proximal end of the entire system. The user may thread a suture through a clip and then load the clip into the tooling. The clip may, in certain designs, already be premounted and then require the final advance by the physician to the site. At the site the physician activates the handle to apply a force to the clip, thereby locking it to the suture. The application of force first secures the clip and captures the suture material within the mating surfaces, and then expels the clip from the tool to remain within the patient.

Suture clips disclosed herein include friction fit embodiments where the components of the clips capture the suture with friction, alignable finger embodiments that involve unaligned rails with apertures formed in each rail that provide a tortuous path for suture engagement that captures the suture and cylinder embodiments including locking cap embodiments, locking inner rod embodiments, inner wedge embodiments, opposing eyelets embodiments and wrapped cylinder embodiments that capture the suture with a mating semicircular sleeve.

The present invention pertains to improvements to an endoscopic suturing device such as that disclosed in U.S. Pat. Ser. Nos. 5,792,153 and 5,080,663, the contents of which are incorporated by reference herein in their entirety. The improved suturing device and methods of the present application can be used to suture tissue internally via an endoscope for a wide variety of purposes such as: attaching a feeding tube to small intestine; closing intestinal openings in the case of a fistula, repairing esophageal tears and suturing tissue sites of localized bleeding. However, the invention is especially useful in the endoscopic suturing procedures to treat gastroesophageal reflex disease (GERD).

Another embodiment of the suture delivering, locking and severing systems described herein includes a multi-coaxial catheter with a three or four finger collet jaw affixed at a distal end. The catheter has a distal end from which the collect fingers distally project. The collet fingers are made of a material such as stainless steel or an engineering grade of plastic that allow the collet fingers to flex or spring from a pre-biased first open position to a second closed position and back to the first position. Alternatively, the collet fingers can be designed to flex or spring from a pre-biased first closed position to a second open position and back to the first position. The collet fingers define a cage within which a suture clip assembly is premounted. The cage is defined proximally by a distal end of the collet body and distally by flanges extending radially inwardly from the distal ends of the collet fingers. The cage is sized so that a plurality of suture clip plugs can be preloaded into the cage along with a single suture clip ring. By biasing the collet fingers in an open position, the need for cam surfaces and cam followers is eliminated.

In one embodiment, a single pusher, adapted to slide within the catheter body, is provided to engage loaded suture clip components and to disengage an outer sliding sleeve that is used to radially constrain the collet fingers into a closed position. In another embodiment, a separate control surface provided coaxially about the collet cage is employed to slide the outer sliding sleeve relative to the collet cage and the pusher.

With any of the embodiments, the outer sliding sleeve is provided to secure the collet fingers in a closed position when placed in a distally advanced position. The outer sliding sleeve performs the additional function of severing the suture at a point proximal to the suture clip after engagement of the suture upon proximal retraction. One or more suture slots are provided in the distal end of the outer sliding sleeve to provide suture exits. A distal end of the suture slots are sharpened to sever the suture. Upon proximal retraction of the outer sliding sleeve, the distal end of suture slot engages the suture and severs it when the distal end of the suture slot travels proximally to the proximal end of the collet fingers. Optionally, a fixed metallic ring can be affixed to the outer surface of the collet at a point proximal to the collet fingers and inside the outer sliding sleeve. The metallic ring is formed with a sharp proximal tip that engages and severs the suture when the outer sliding sleeve is proximally retracted. The design enables the suture clip to be cinched in close proximity to the sutured tissue as well as allow for the severing of the suture tails and release of the suture from the delivery device in one step.

The suture clips designed for use with the referenced suture clip delivery systems are comprised of a plug and a ring that are configured to allow a suture to interwind through the clip in such a manner that the clip components move with minimal friction while in an open position. The plug is a headless design that has features that allow for a positive lock with the ring. Channels are provided in the plug to provide access ways for the suture to lessen the effort needed to thread the suture into the plug. The locking features of the plug are compressible so that when in a locked state, the suture is captured via a combination of frictional engagement and the locking surfaces The plugs have features built into their proximal and distal ends to allow stacking of the plugs to enhance alignment for the delivery of axial forces to set the plugs in rings. Additionally, a diverter for channeling the suture into axial slots formed in the plug is provided in one embodiment to extend distally of the distal end of the ring, when assembled with the plug, to integrate the tissue and cause fibrosis. The fibrosis causes the tissue to become more bulky which is thought to enhance the therapeutic effect of this technique.

In another embodiment, the plug and ring are formed with inter-locking ribs or scales that enhance the advancement of the plug into the ring and prevent disengagement. The ribs are fashioned to allow one-way movement of the suture through the suture clip.

Once threaded into the ring and plug, the suture is passed through finger slots formed between adjacent collet fingers and out the suture slot of the outer sliding sleeve. This enables the suture tails to be channeled externally of the catheter for removal at the proximal end of the catheter outside the patient after the tails have been severed at a point proximal to the now assembled suture clip. The catheter operator may thread a suture through a clip and then load the clip into the tooling or thread the suture through a premounted clip. At the site the physician activates the handle to apply a force to the clip, thereby locking it to the suture. The application of force would first secure the clip components capturing the suture material within the mating surfaces, and then expel the clip from the tool to remain within the patient.

Suture clips disclosed herein include combination friction fit and positive locking embodiments where the components of the clips capture the suture with friction and lock the suture in place with inter-locking surfaces. It is to be appreciated that a wide variety of suture clip configurations can be formed from the basic ring/plug configuration that employs a friction fit/positive lock securing means.

A yet further suture locking and severing system described herein includes, in one general embodiment, a multi-coaxial catheter, and in a second general embodiment, a system dimensioned for use in the working channel of an endoscope. Each general embodiment has a two, three or four finger collet jaw affixed at a distal end. The collet jaw has a collet body from which the collet fingers distally project. The collet fingers are made of a material such as stainless steel or high modulus plastics that allow the collet fingers to flex or spring from a first closed position to a second open position and back to the first position. Alternatively, the collet fingers can be designed to flex or spring from a first open position to a second closed position and back to the first position. This is accomplished by providing a radial bias in either the open or closed position. The collet fingers define a cage within which a suture clip assembly is premounted. The cage is defined proximally by a distal end of the collet body or by ramps formed on the inside walls of the collet fingers distal to the collet body and distally by flanges extending radially inwardly from the distal ends of the collet fingers. A further spatial restriction is provided toward the proximal end of the cage by the ramps that extend radially inwardly from the inner walls of the collet fingers and that additionally function as cams to open the collet fingers.

In one embodiment, a single pusher, adapted to slide within the catheter body, is provided to engage loaded suture clip components. In this embodiment, the collet fingers are biased in an open position. In another embodiment, a two-pusher system is employed that utilizes an inner pusher to secure a plug to a ring that together comprise the suture clip. A second pusher provided coaxially about, and in sliding engagement with, the inner pusher has a tapered distal end that interacts with the proximal ramps when advanced distally to cause the collet fingers to move from a closed position to an open position.

With any of the single or double pusher embodiments, an outer sliding sleeve can be provided to secure the collet fingers in a closed position when placed in a distally advanced position. The outer sliding sleeve performs the additional function of severing the suture at a point proximal to the suture clip after engagement of the suture. A suture slot is provided in the distal end of the outer sliding sleeve to provide a suture exit. Upon proximal retraction of the outer sliding sleeve, the distal end of the suture slot engages the suture and severs it when the distal end of the suture slot travels proximal to the proximal end of the collet fingers. Optionally, a fixed metallic ring can be affixed to the outer surface of the collet at a point proximal to the collet fingers and inside the outer sliding sleeve. The metallic ring is formed with a sharp proximal tip that engages and severs the suture when the outer sliding sleeve is proximally retracted. The design enables the suture clip to be cinched in close proximity to the sutured tissue as well as allow for the severing of the suture tails and release of the suture from the delivery device in one step.

In yet a further embodiment, a head of the plug portion of the suture clip can be chamfered to engage the aforementioned ramps or ramps formed on the inner surfaces of the distal ends of the collet fingers to open the collet segments when a single pusher is distally advanced. This allows for the engagement of the plug and ring and release of the joined plug and ring in one step. The dimensions of the suture clip and collet segments are optimized to allow for full engagement of the plug and ring prior to clip release from the delivery device.

The suture clips designed for use with the suture clip delivery system are comprised of a plug and a ring that are configured to allow a suture to inter-wind through the clip in such a manner that the clips move with minimal friction while in an open position. In a closed position, the clip captures the suture by frictional engagement. Once threaded into the ring and plug, the suture is passed through finger slots formed between adjacent collet fingers and out the suture slot of the outer sliding sleeve. This enables the suture tails to be channeled externally of the catheter for removal at the proximal end of the catheter outside the patient after the tails have been severed at a point proximal to the now assembled suture clip. The catheter operator may thread a suture through a clip and then load the clip into the tooling or thread the suture through a premounted clip. After positioning the delivery system at the sutured tissue site, the device operator activates the handle to apply a force to the clip, thereby locking it to the suture. The application of force first secures the clip components thus capturing the suture material within the mating surfaces, and second expels the clip from the delivery system tool to remain within the patient.

Suture clips disclosed herein include friction fit embodiments where the components of the clips capture the suture with friction. It is to be appreciated that a wide variety of suture clip configurations can be formed from the basic ring/ plug configuration that employs a friction fit securing means. Of course, the ring and plug components of the clip can be provided with interlocking features for enhancing the suture capturing effect.

In a still further embodiment, a suture clip delivery device having pivoting collet fingers is disclosed. The collet fingers rotate about a pin secured to a collet cage body. A pusher, suture clip component or other component radially restrains the pivoting collet fingers from pivoting radially outwardly at a distal end when proximal to a cinched position. Another embodiment employs a ring secured about the collet cage body. A distal edge of the ring provides a pivot point and eliminates the need to secure the pivoting collet fingers to the collet cage with pins.

Also disclosed is a suture clip loader used to deliver the suture clip components into the collet cage. The suture clip loader has two main components, a main body through which a hypotube is secured and a plunger comprising a plunger head and a plunder rod. The plunger rod is dimensioned to slide freely within the hypotube. A suture clip ring is placed over a first end of the hypotube that is situated within a cavity formed in the loader main body. The distal end of a suture clip plug is loosely fit within the lumen of the first end for delivery into a collet cage. A collet cage with the collet fingers in an open position is advanced over the plug, hypotube and ring. Advancement of the plunger into the hypotube from a second hypotube end causes disengagement of the suture clip plug into the collet cage. The collet cage fingers are then moved into a closed position by advancing the outer sliding sleeve so as to grasp the suture clip ring that is retained in the collect cage when the collet cage is removed from the hypotube

BRIEF DESCRIPTION OF THE DRAWINGS

FIG. 1b is a perspective view of a suture clip delivery/locking device and suture clip in an intermediate position according to another embodiment of the invention.

FIG. 1c is a perspective view of a suture clip delivery/locking device and suture clip in an advanced intermediate position according to another embodiment of the invention.

FIG. 17 is a side elevational view of a suture clip assembly in a closed position according to another embodiment of the invention.

FIG. 18 is a perspective view of a suture clip assembly in a closed initial position according to another embodiment of the invention.

FIG. 19 is an end elevational view of a suture clip assembly in a closed initial position according to one embodiment of the invention.

FIG. 20 is an end elevational view of a suture clip assembly in a closed initial position according to a further embodiment of the invention.

FIG. 21 is an end elevational view of a suture clip assembly in a closed initial position according to one embodiment of the invention.

FIG. 111 is a side view of a ribbon plug suture clip component according to a yet another embodiment of the invention.

FIG. 112 is a side sectional view of a partially assembled ribbon plug/rigid ring suture clip assembly according to a yet another embodiment of the invention.

FIG. 113 is a side sectional view of an assembled mesh plug/rigid ring suture clip assembly according to a yet another embodiment of the invention.

FIG. 114 is a side sectional view of an assembled channeled plug/ribbon ring suture clip assembly according to a further embodiment of the invention.

FIG. 115 is a side view of a ribbon ring suture clip component according to a further embodiment of the invention.

FIG. 116 is a side view of a ribbon ring suture clip component in a relaxed reduced diameter state according to a further embodiment of the invention.

FIG. 117 is a side view of a ribbon ring suture clip component in a stretched state according to a further embodiment of the invention.

FIG. 118 is a side elevational view of a channeled plug suture clip component according to a further embodiment of the invention.

FIG. 119 is a side elevational view of an assembled channeled plug/ribbon ring suture clip assembly according to a further embodiment of the invention.

FIG. 120 is a side view of an assembled barbell plug/mesh ring suture clip assembly according to a yet further embodiment of the invention.

FIG. 121 is a partial cutaway side perspective view of a single pusher suture clip delivering, locking and severing catheter distal end with a pre-mounted suture clip ring and three stacked suture clip plugs according to one embodiment of the invention.

FIG. 122 is a side perspective view of a single pusher suture clip delivering, locking and severing catheter distal end according to one embodiment of the invention.

Figure 123:
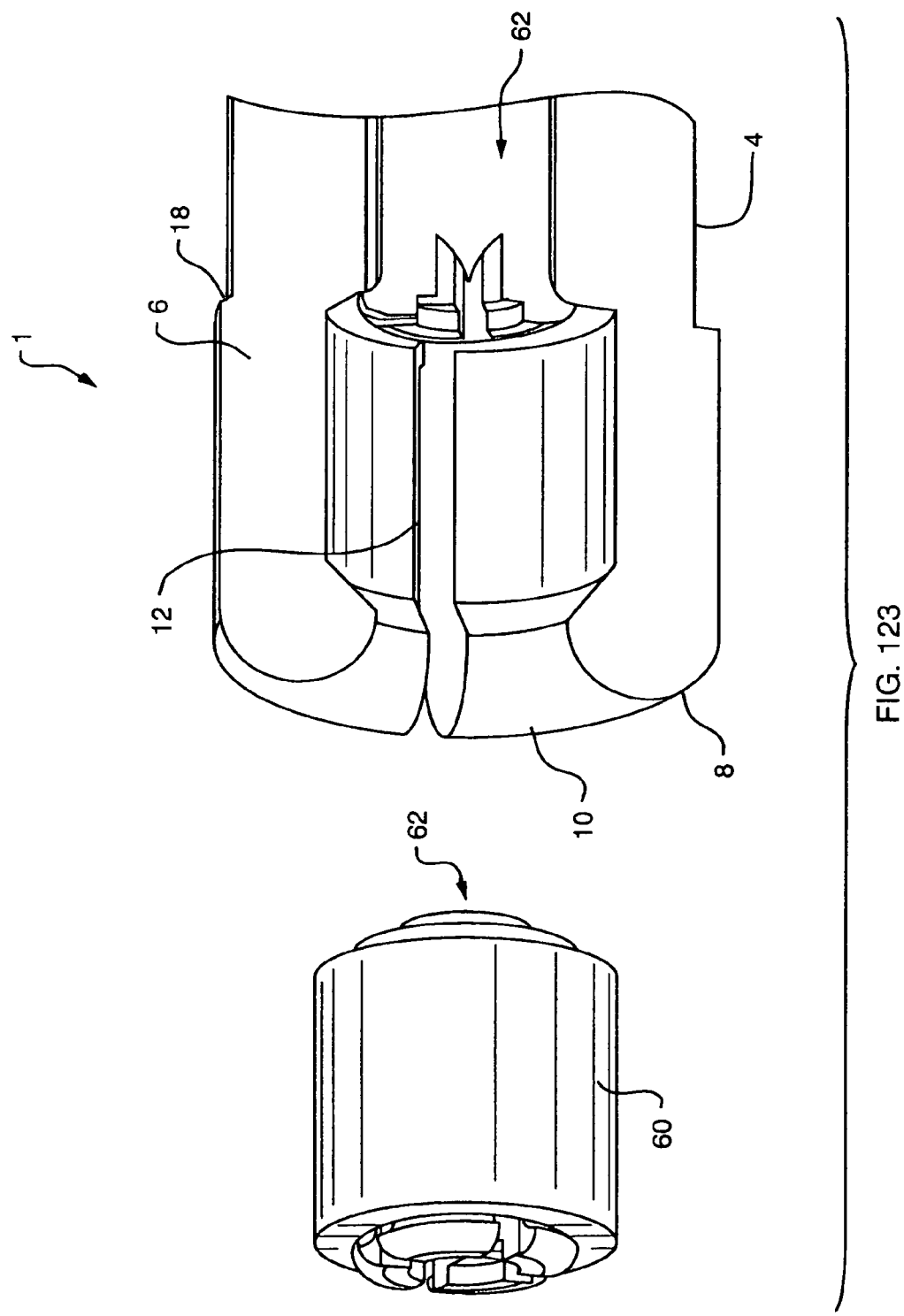

FIG. 123 is a fragmentary partial sectional side perspective view of a single suture clip delivering, locking and severing catheter distal end with a single suture clip plug and without a loaded suture clip ring according to one embodiment of the invention.

Figure 124:
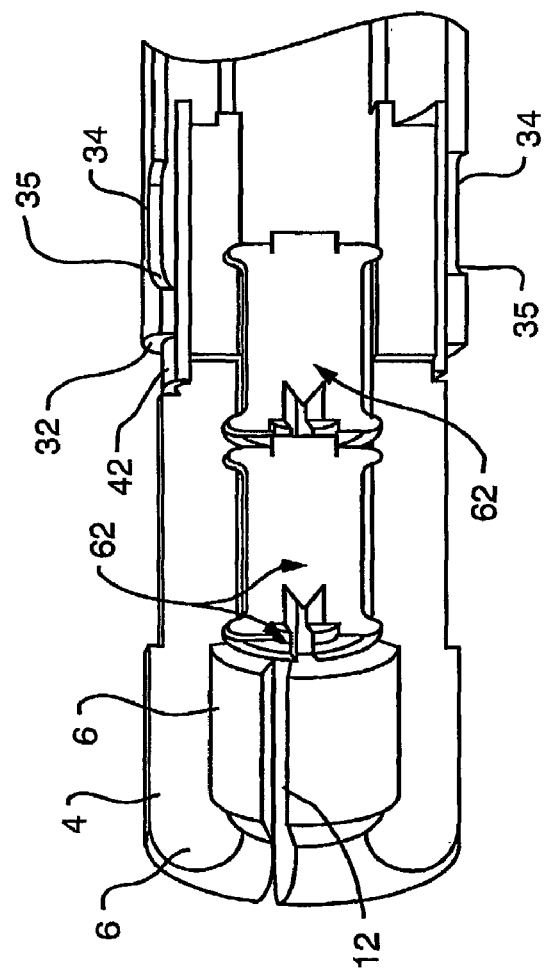

FIG. 124 is a partial sectional side perspective view of a single pusher suture clip locking and severing catheter distal end with an assembled suture clip and two stacked suture clip plugs according another embodiment of the invention.

Figure 125:
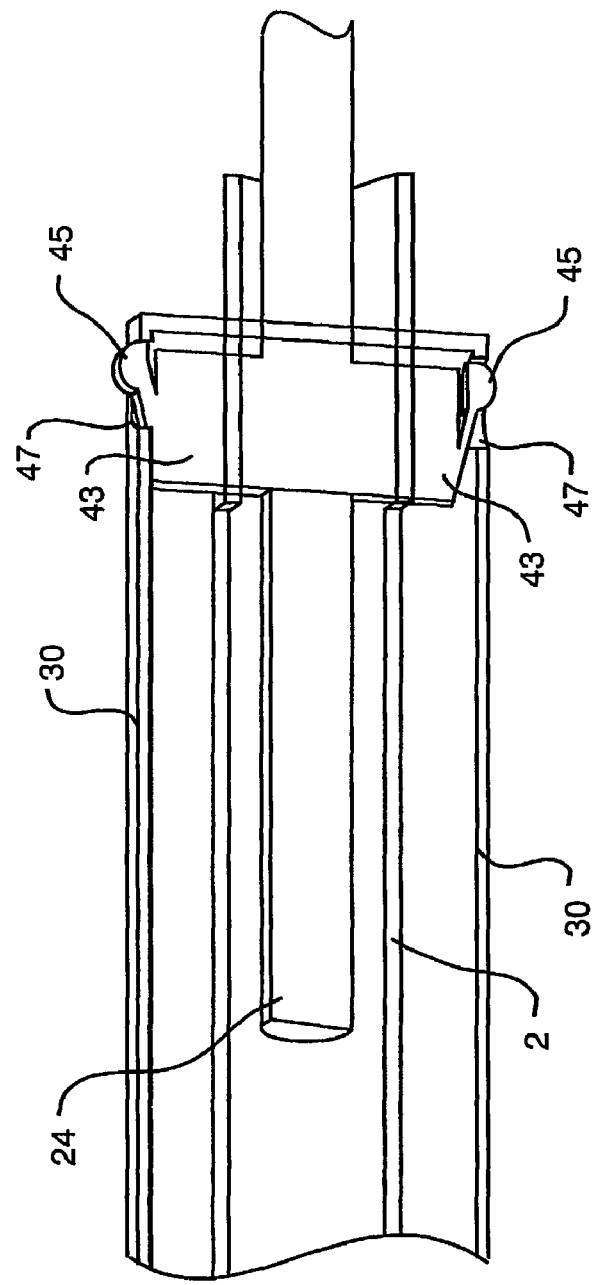

FIG. 125 is fragmentary side perspective view of a single pusher suture clip locking and severing catheter distal end showing a pusher and sliding sleeve locking features according to one embodiment of the invention.

Figure 126:
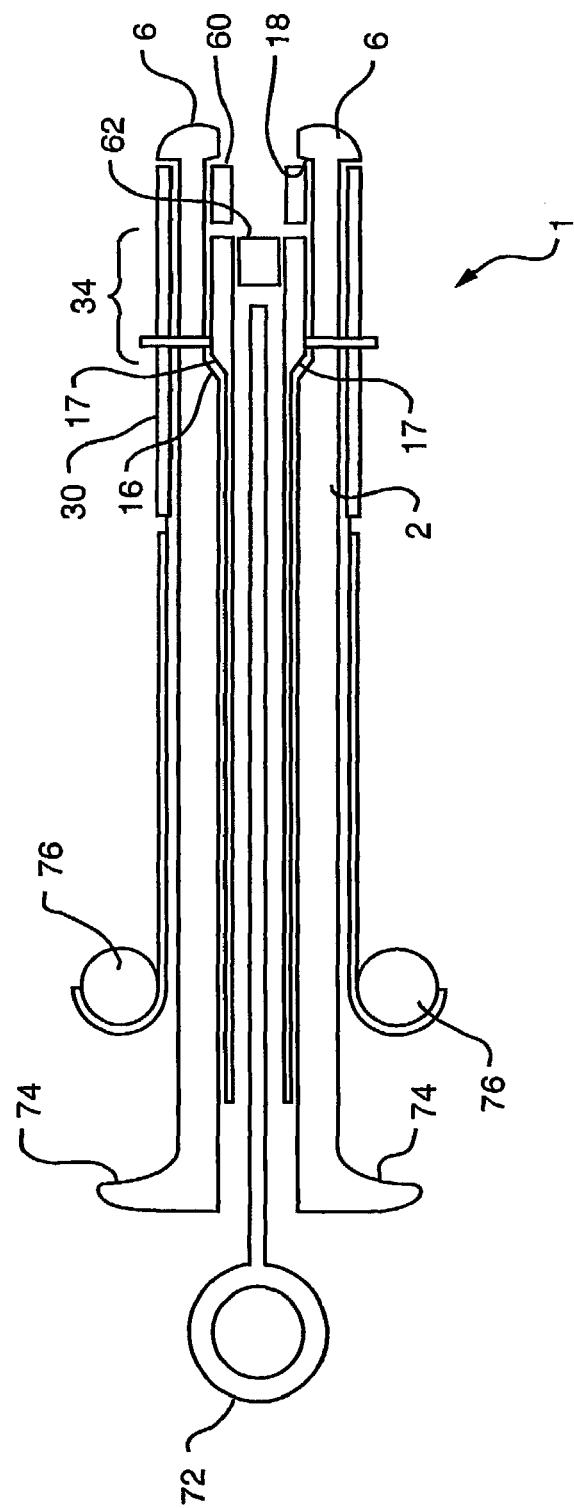

FIG. 126 is a side sectional view of a single pusher suture clip delivering, locking and severing catheter with a sliding sleeve finger pull according to one embodiment of the invention.

Figure 127:
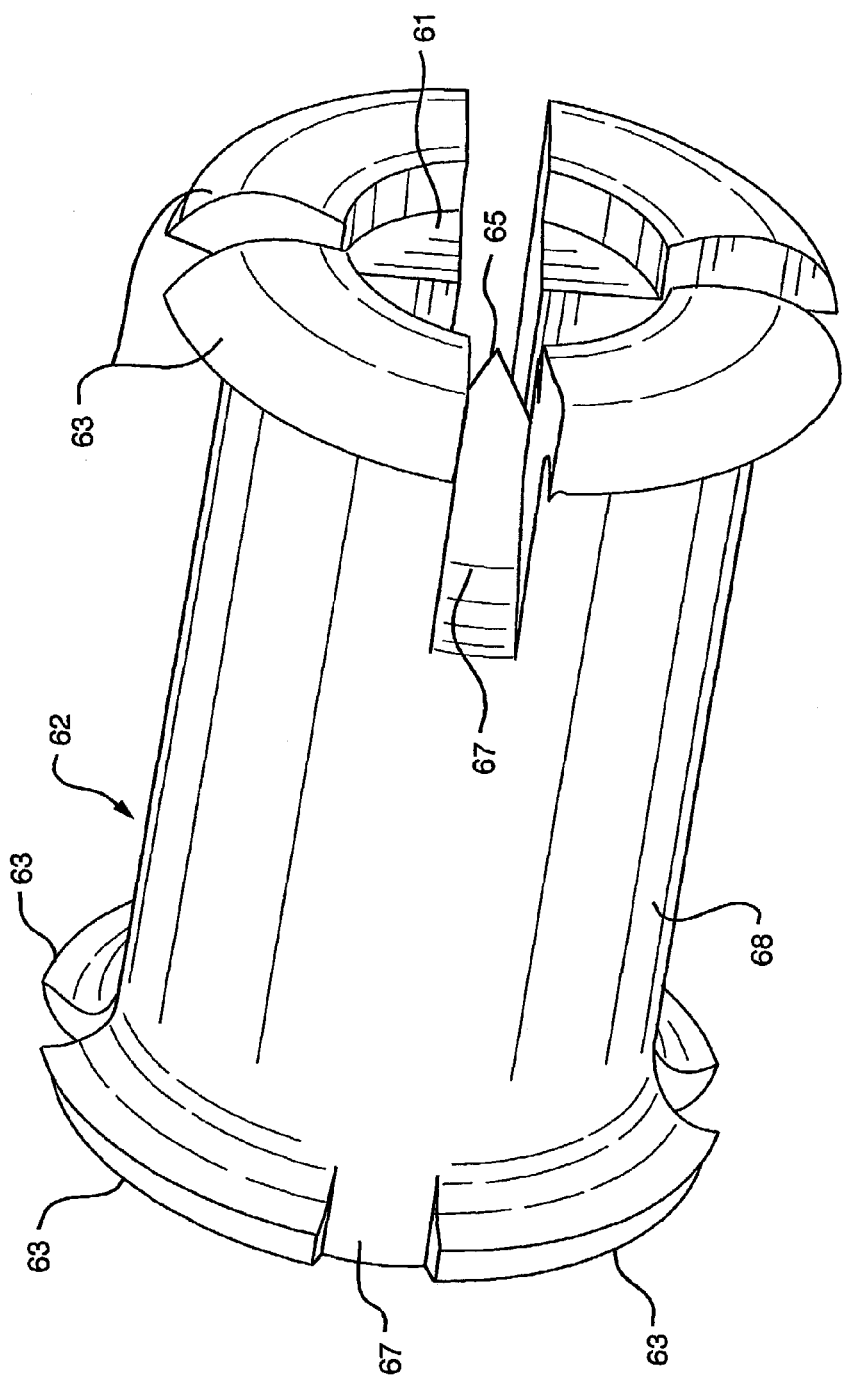

FIG. 127 is a side perspective view of a suture clip plug according to one embodiment of the invention.

Figure 128:
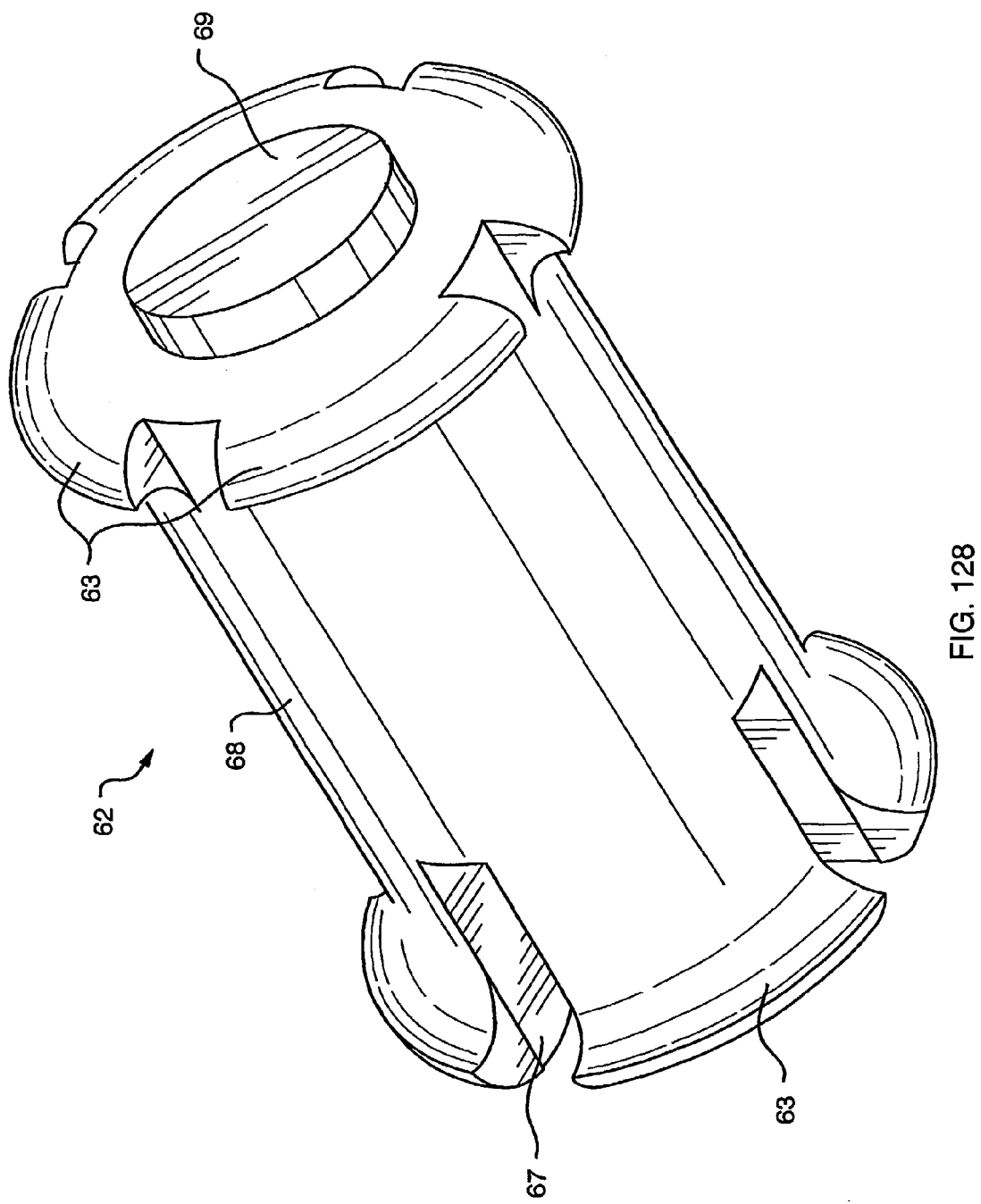

FIG. 128 is a bottom perspective view of a suture clip plug according to one embodiment of the invention.

Figure 129:
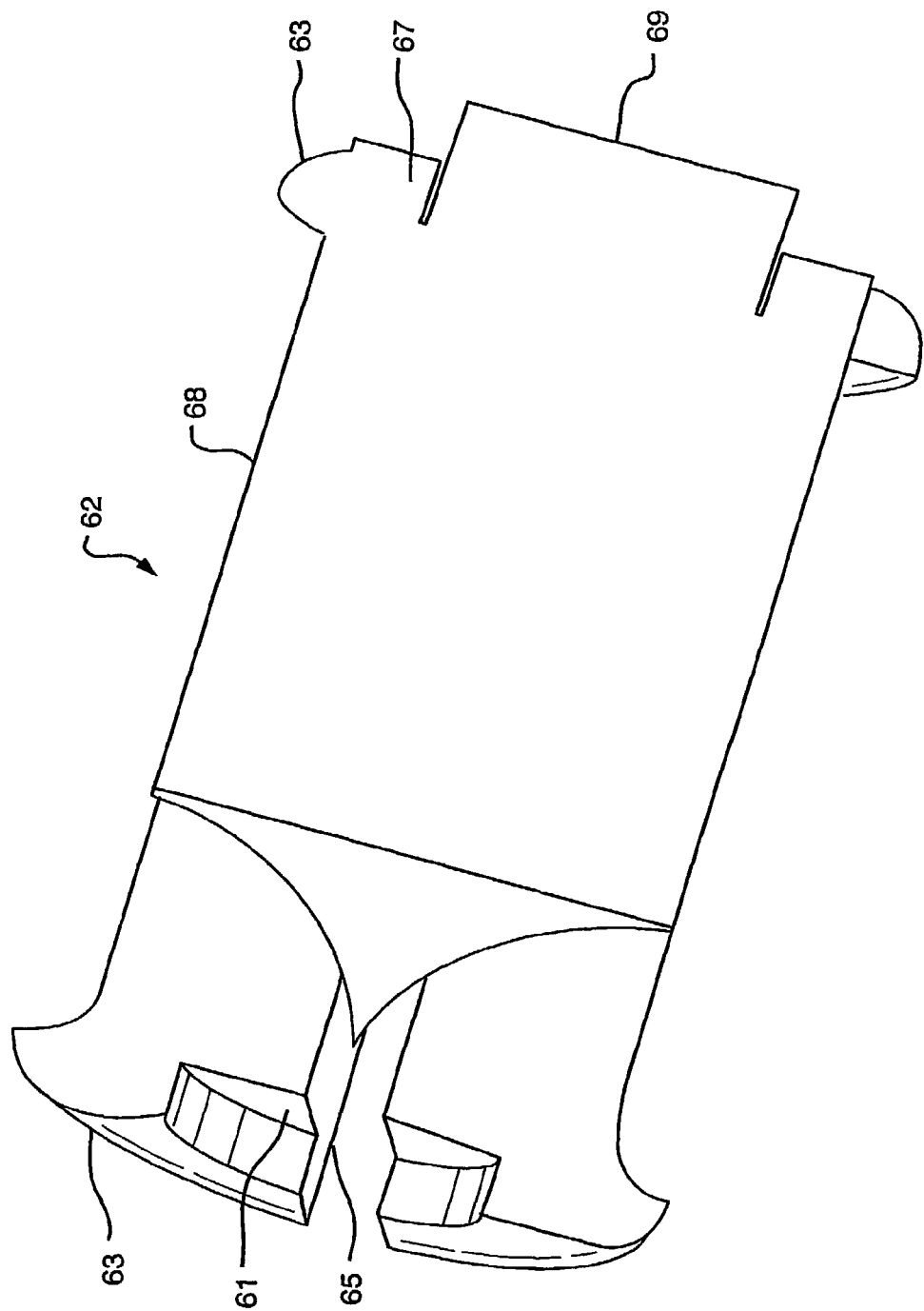

FIG. 129 is a side sectional perspective view of a suture clip plug according to one embodiment of the invention.

Figure 130:
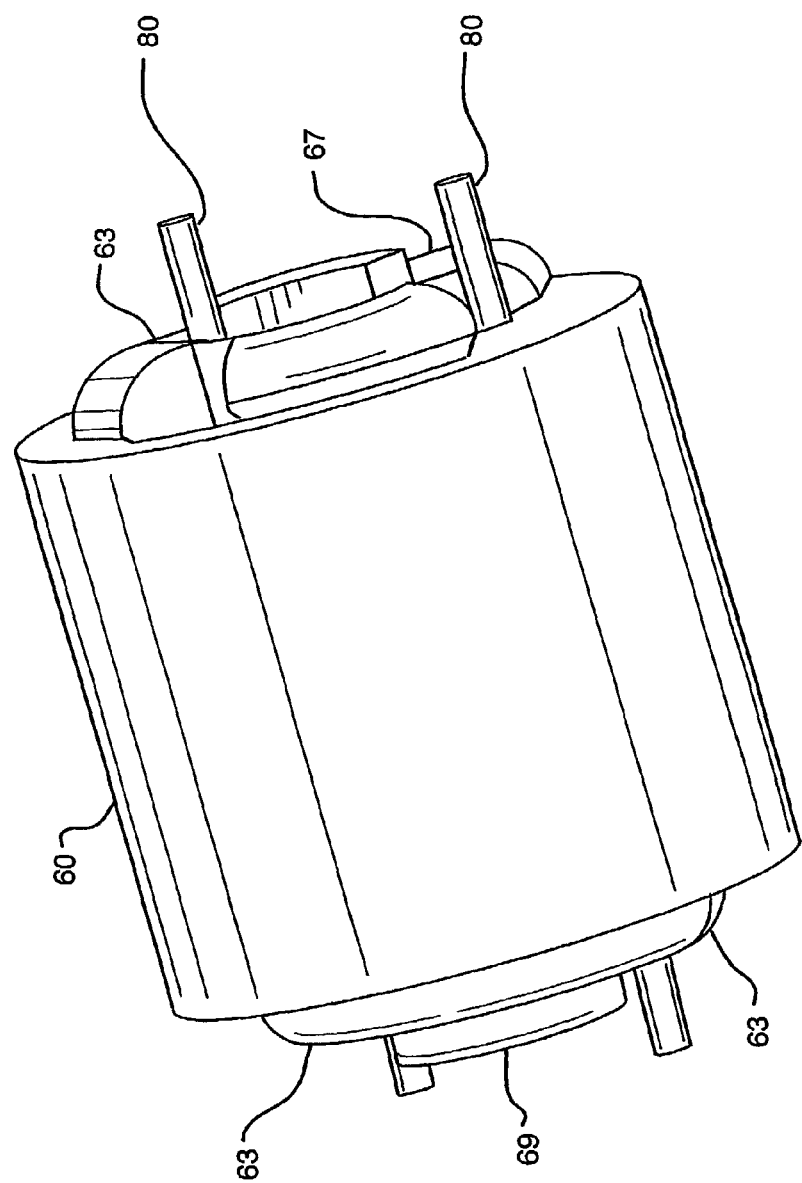

FIG. 130 is a side perspective view of a suture clip assembled to a suture according to one embodiment of the invention.

Figure 131:
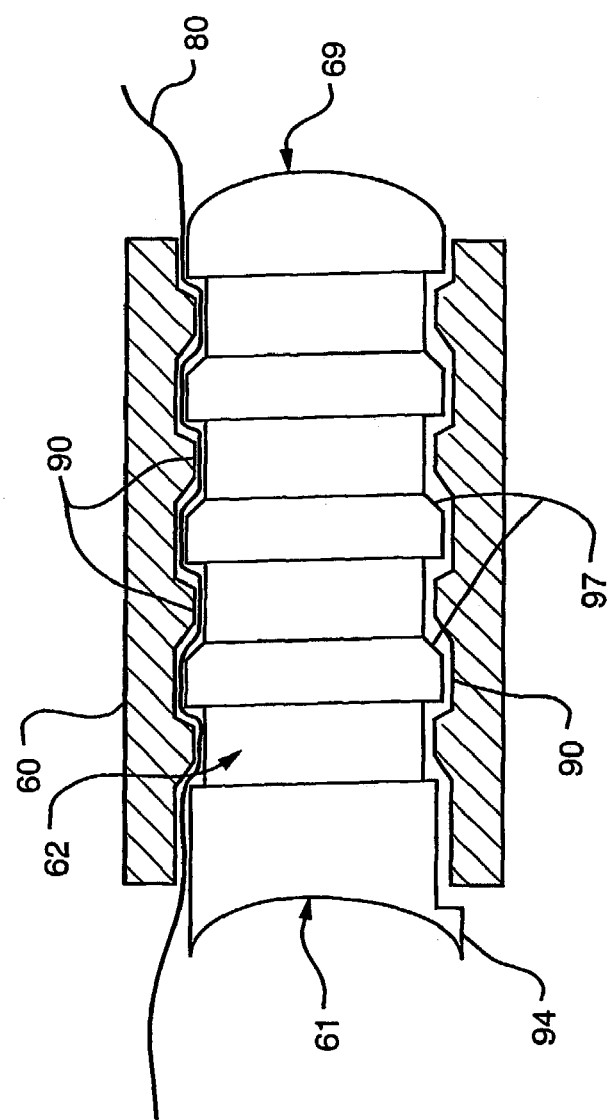

FIG. 131 is a side sectional view of a suture clip assembly with rib formations according to one embodiment of the invention.

Figure 132:
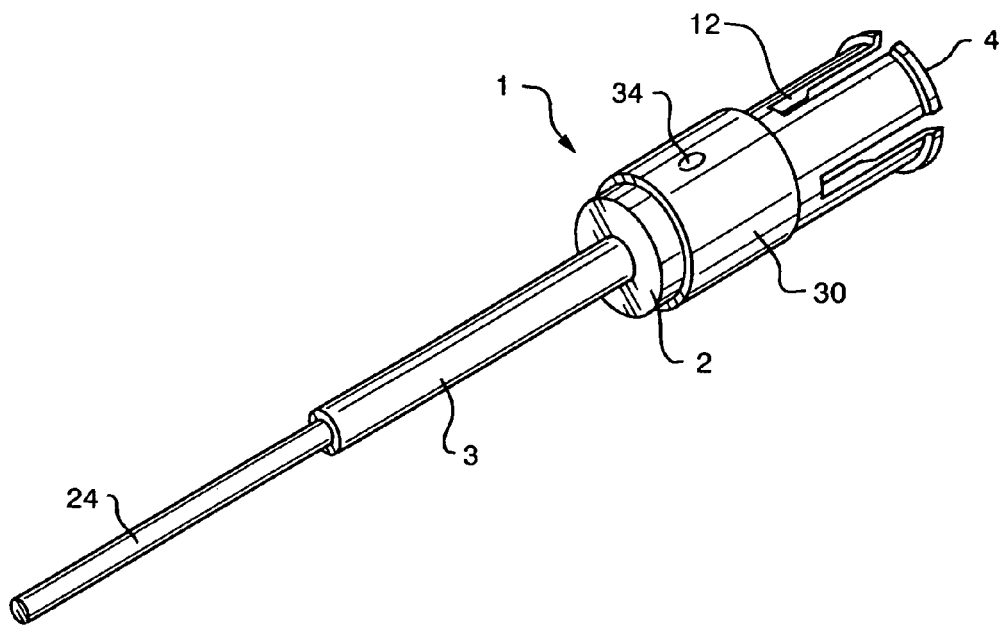

FIG. 132 is a perspective view of a collet cage assembly according to another embodiment of the invention.

Figure 133:
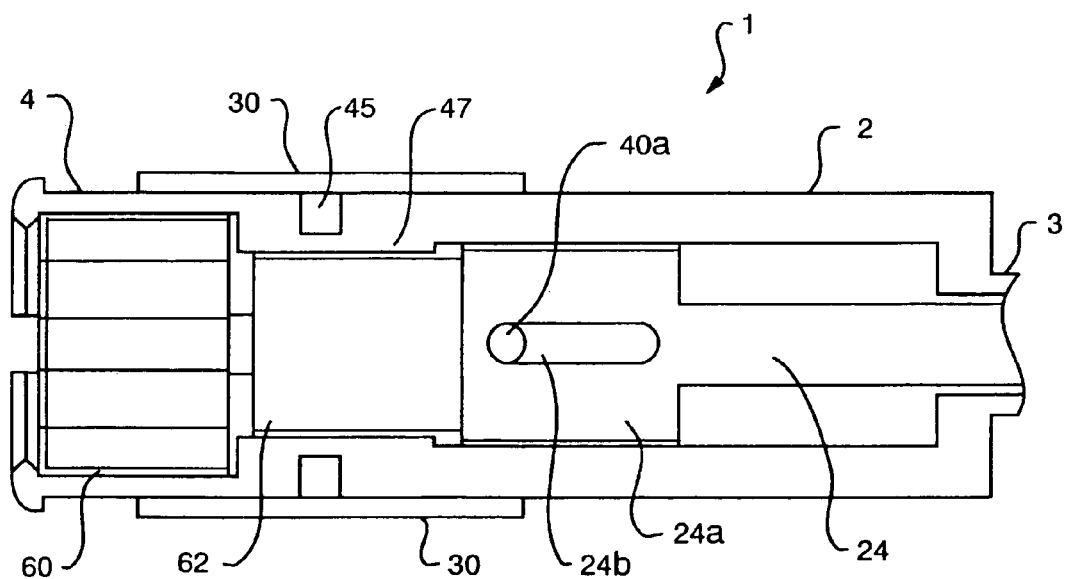

FIG. 133 is a side sectional view of a collet cage assembly according to another embodiment of the invention.

Figure 134:
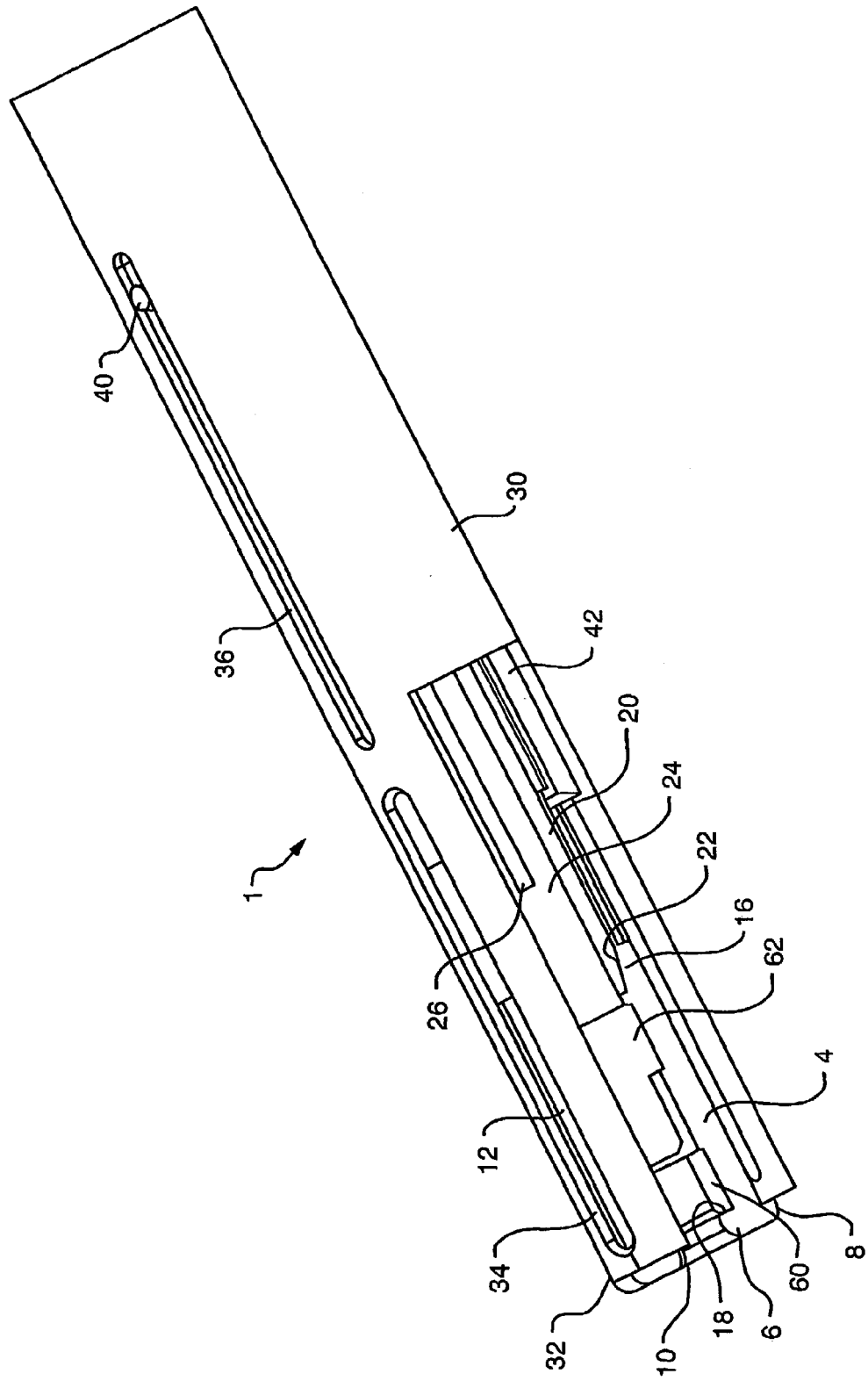

FIG. 134 is a partial cutaway side perspective view of a double pusher suture clip locking and severing catheter distal end with a pre-mounted suture clip assembly according to one embodiment of the invention.

Figure 135:
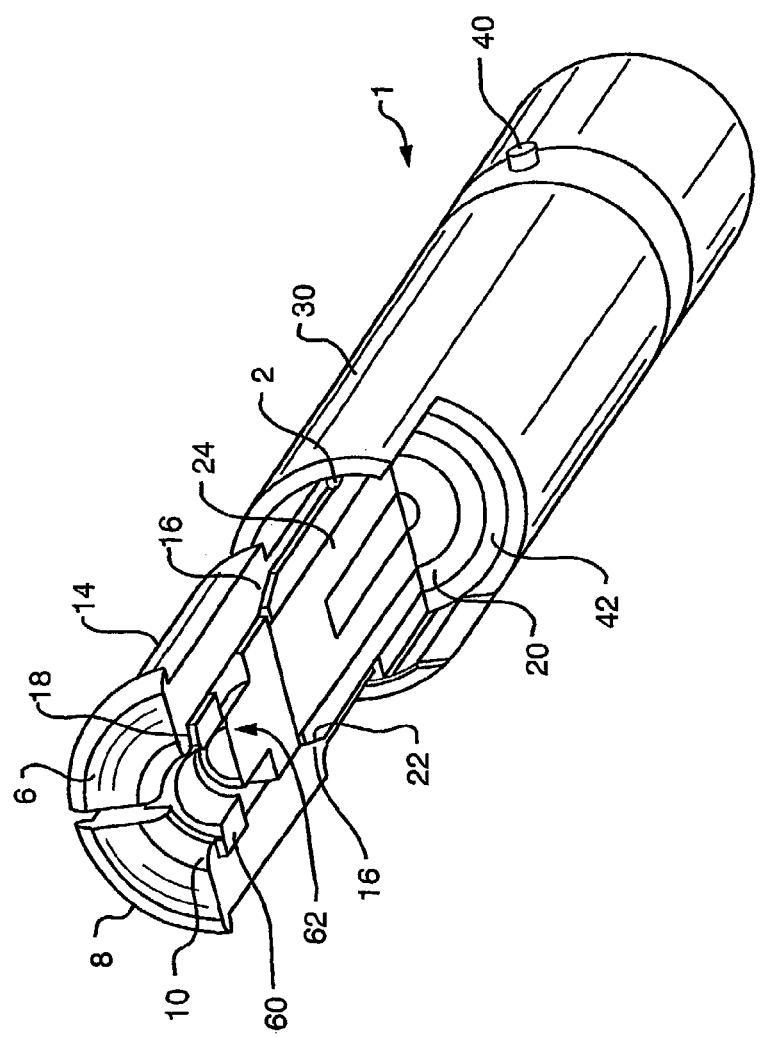

FIG. 135 is a partial sectional front perspective view of a double pusher suture clip locking and severing catheter distal end with a pre-mounted suture clip assembly according to one embodiment of the invention.

Figure 136:
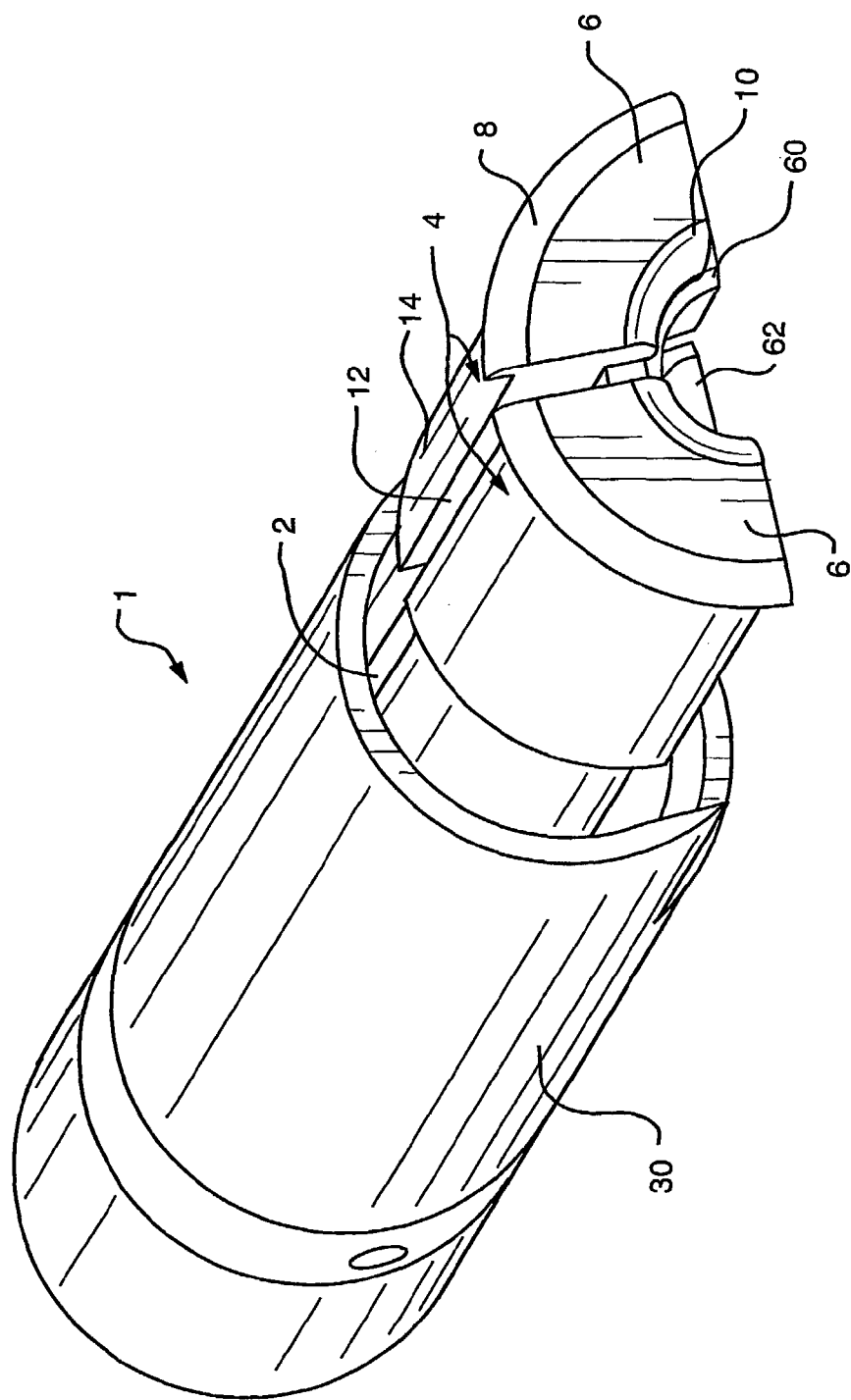

FIG. 136 is a partial sectional top perspective view of a double pusher suture clip locking and severing catheter distal end with an outer sliding sleeve partially retracted according to one embodiment of the invention.

Figure 137:
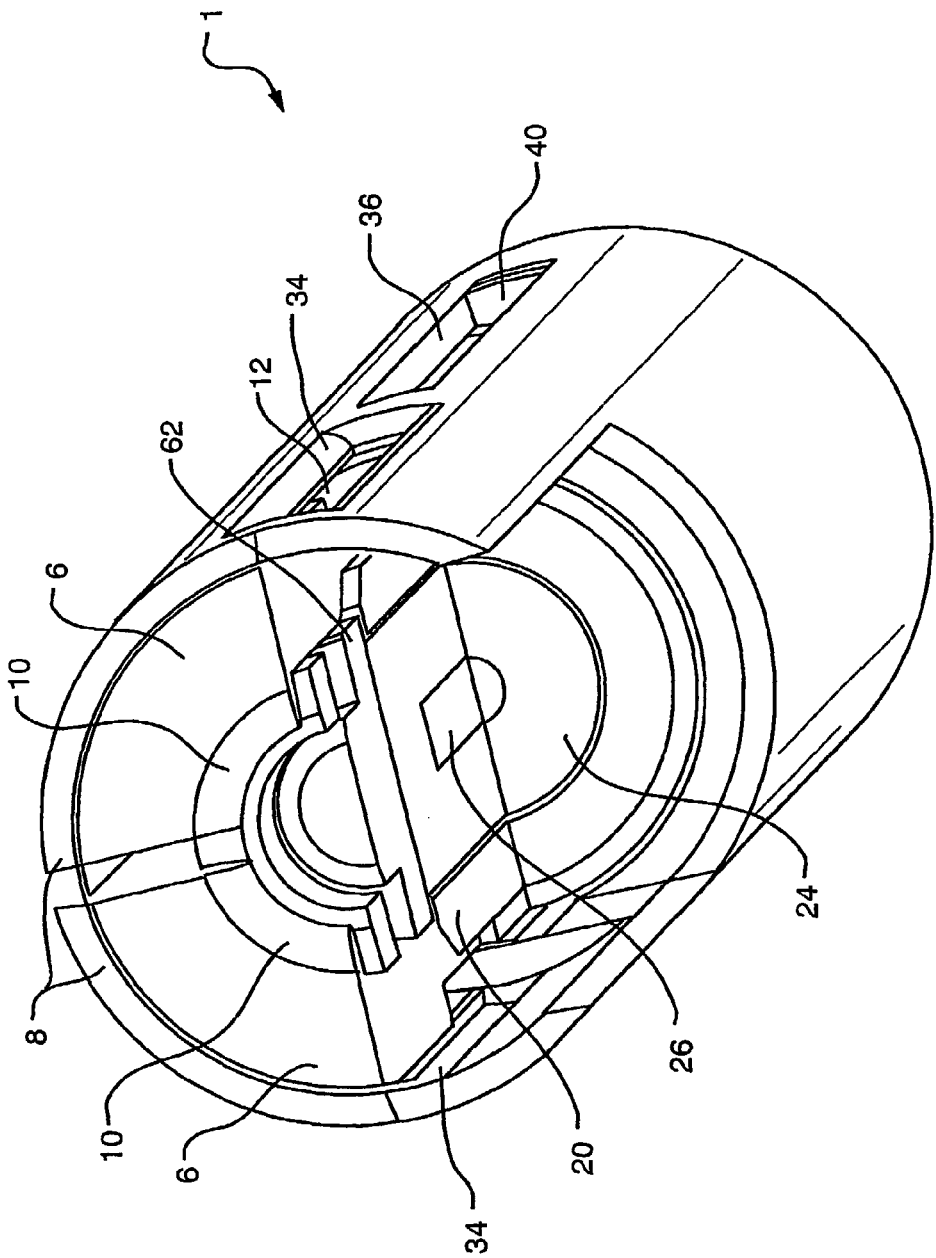

FIG. 137 is a partial sectional front perspective view of a double pusher suture clip locking and severing catheter distal end according another embodiment of the invention.

Figure 138:
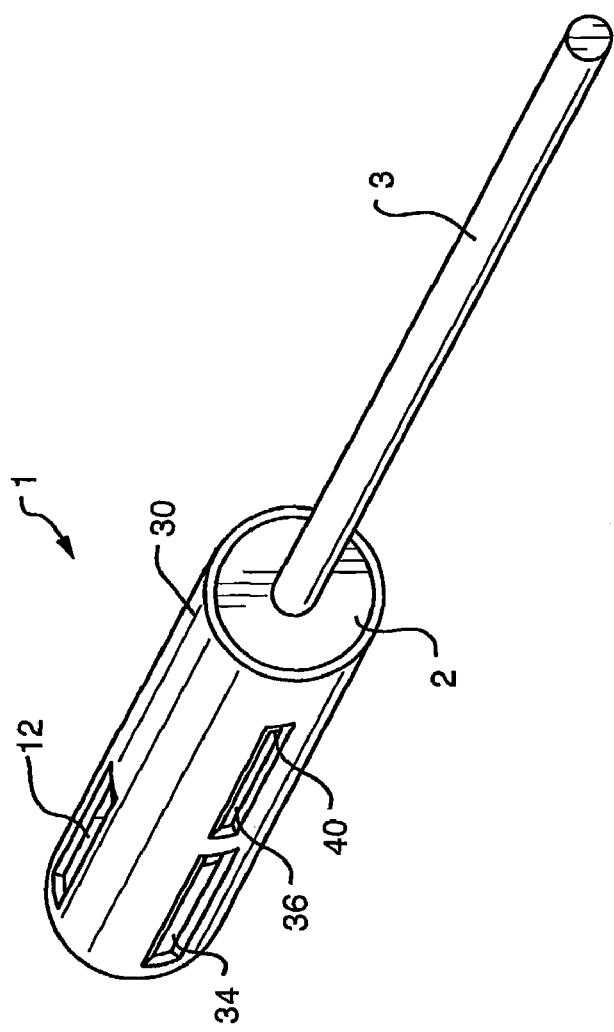

FIG. 138 is back perspective view of a double pusher suture clip locking and severing catheter distal end and partial hypotube body according to one embodiment of the invention.

Figure 139:
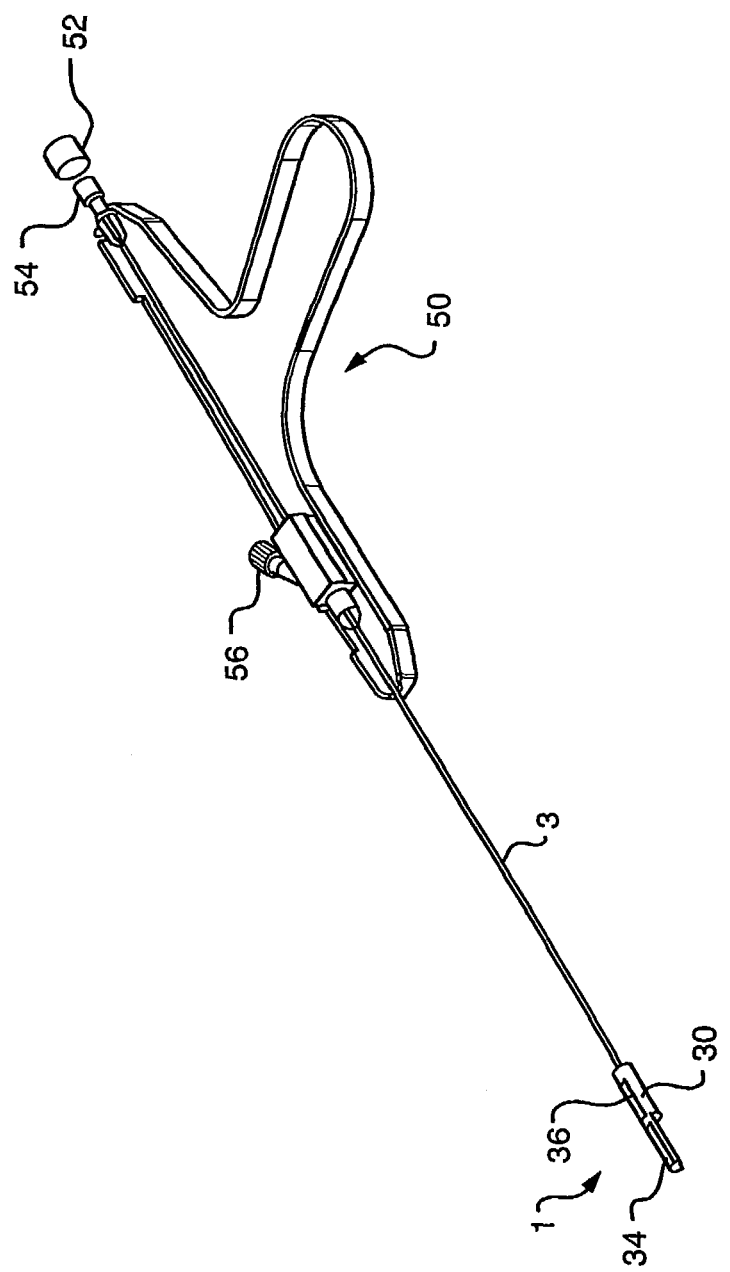

FIG. 139 is a side perspective view of a double pusher suture clip locking and severing catheter according to one embodiment of the invention.

Figure 140:
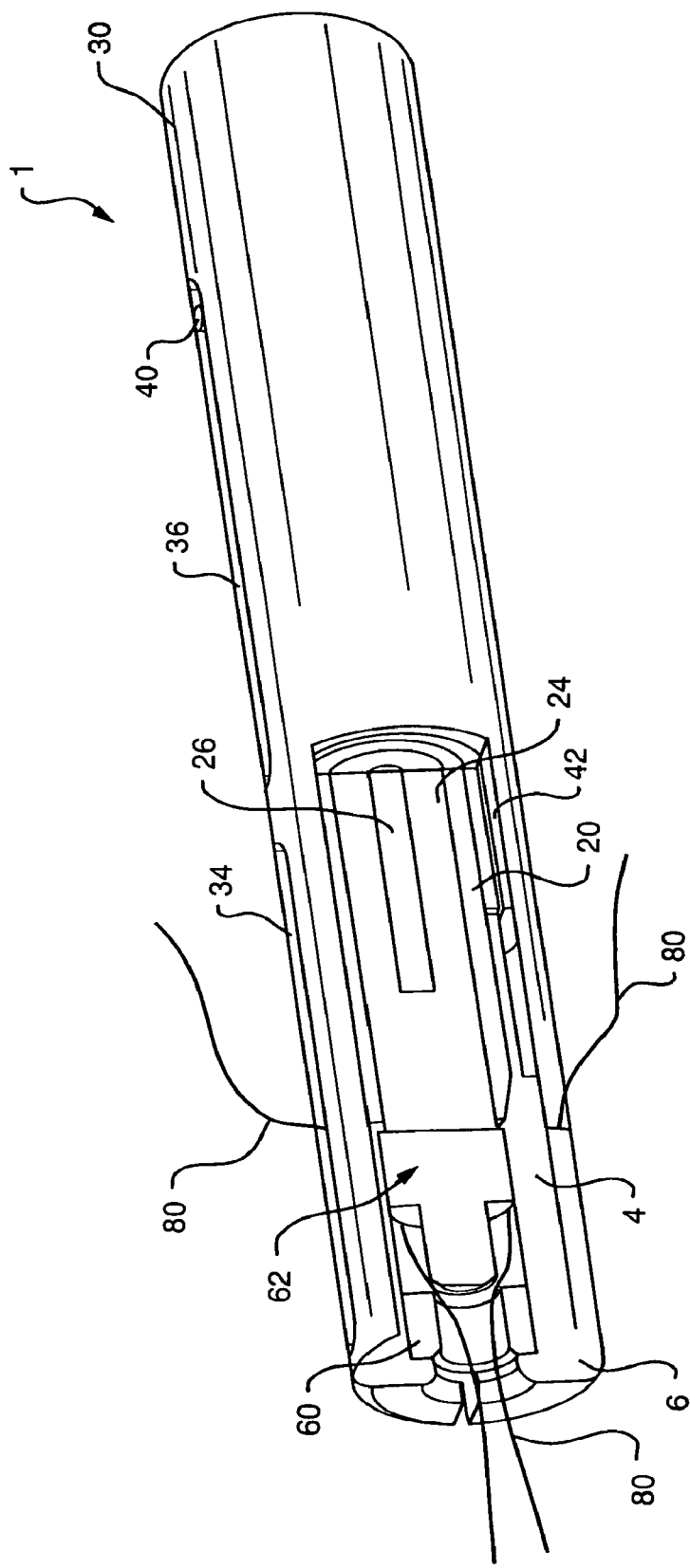

FIG. 140 is a partial cutaway side perspective view of a double pusher suture clip locking and severing catheter distal end with loaded and threaded suture clip components according to one embodiment of the invention.

Figure 141:
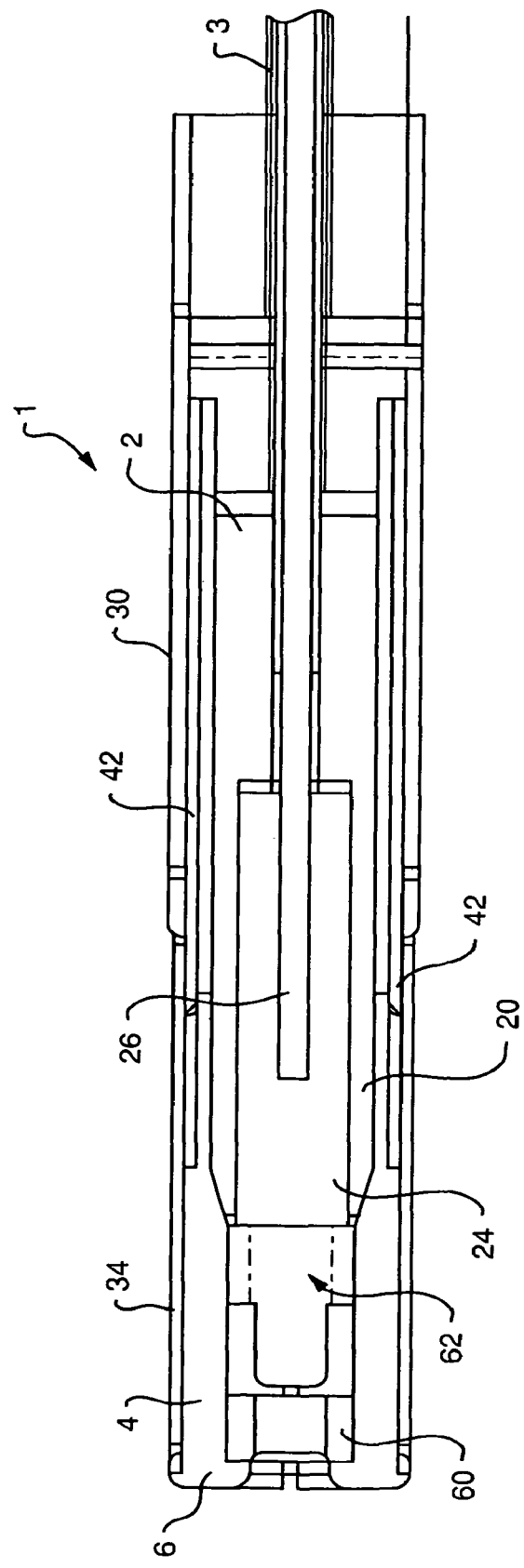

FIG. 141 is a side sectional view of a double pusher suture clip locking and severing catheter distal end with pre-loaded suture clip components according to one embodiment of the invention.

Figure 142:
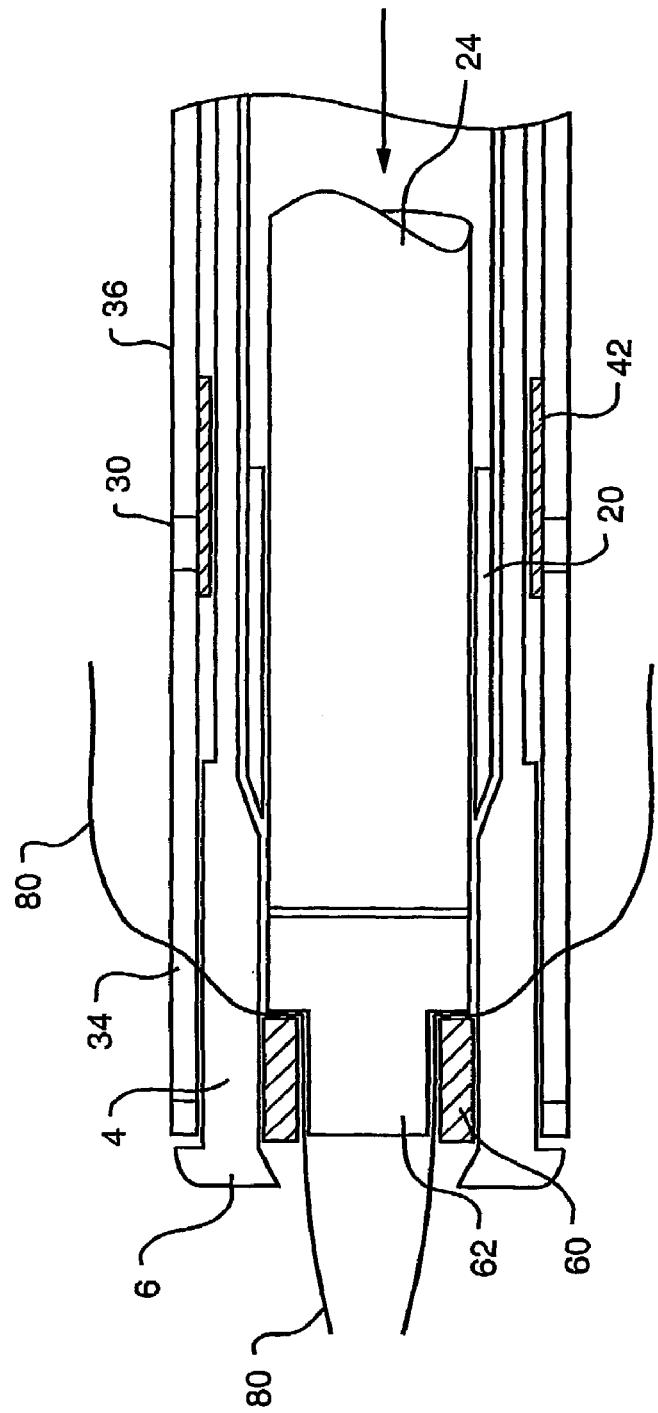

FIG. 142 is a side sectional view of a double pusher suture clip locking and severing catheter distal end with an inner pusher in an advanced position and a suture clip in a cinched condition according to one embodiment of the invention.

Figure 143:
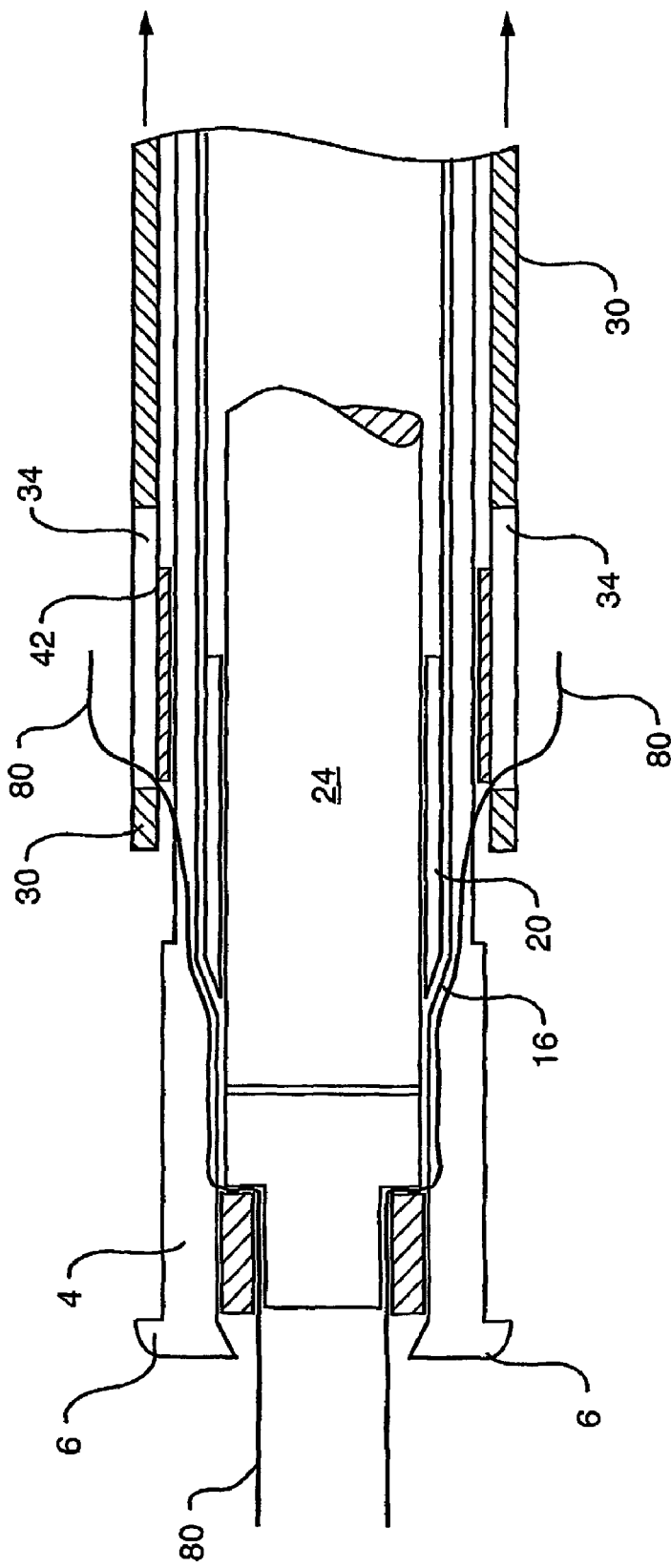

FIG. 143 is a side sectional view of a double pusher suture clip locking and severing catheter distal end with an outer sliding sleeve in a partially retracted position according to one embodiment of the invention.

Figure 144:
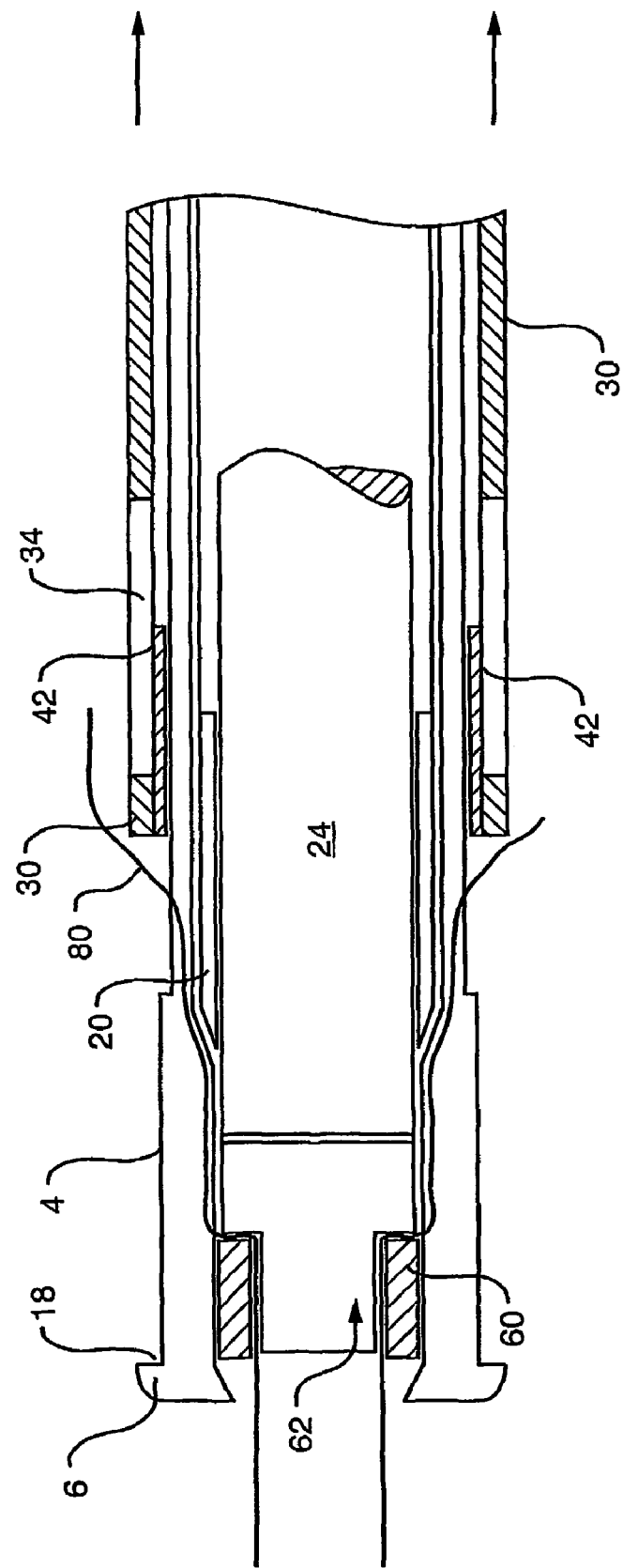

FIG. 144 is a side sectional view of a double pusher suture clip locking and severing catheter distal end with an outer sliding sleeve in a fully retracted position according to one embodiment of the invention.

Figure 145:
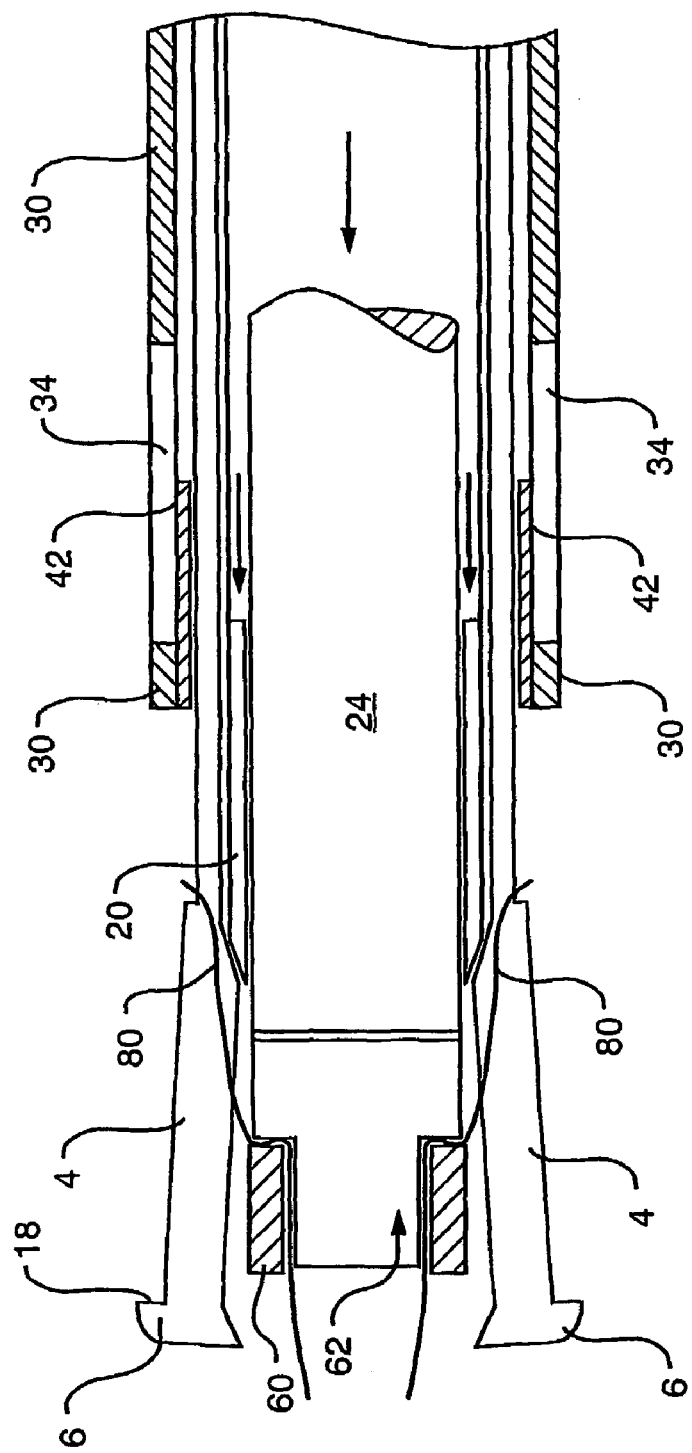

FIG. 145 is a side sectional view of a double pusher suture clip locking and severing catheter distal end with an outer pusher in an advanced position engaging and opening collet fingers according to one embodiment of the invention.

Figure 146:
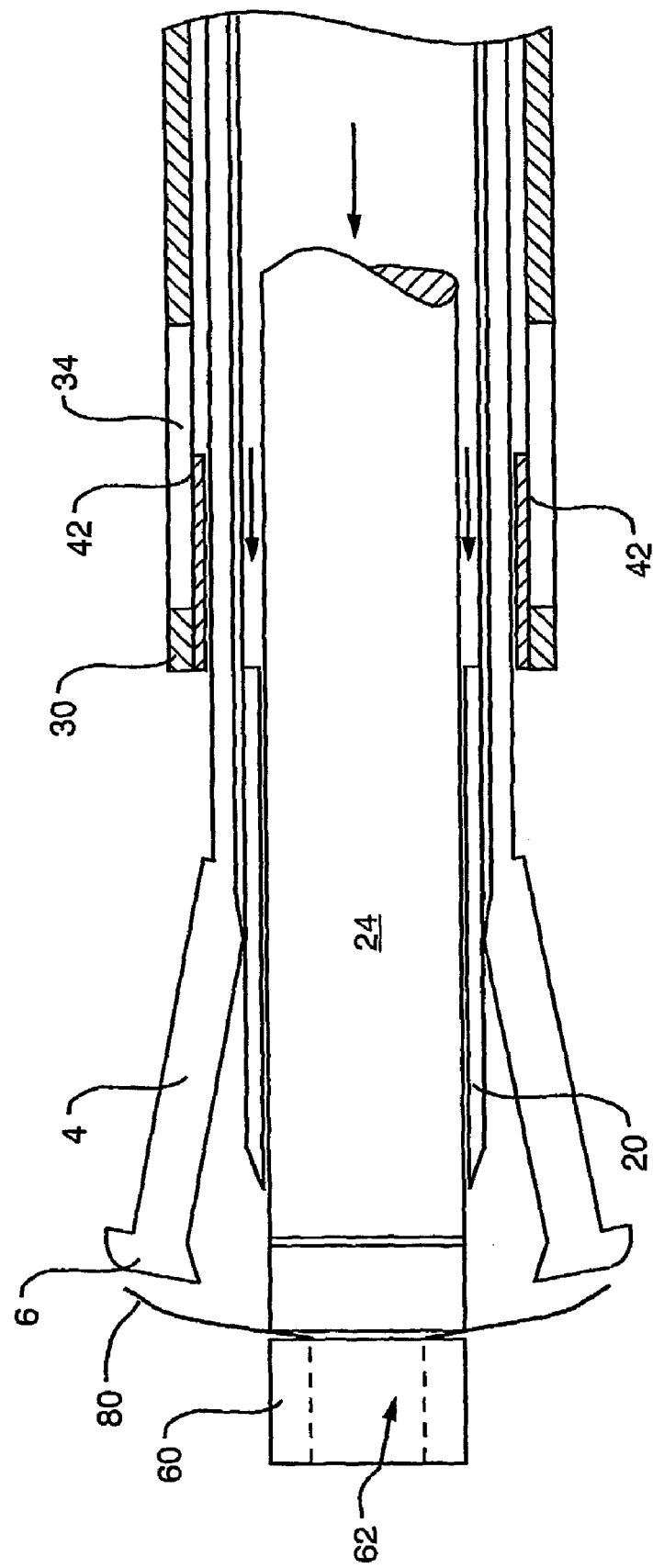

FIG. 146 is a side sectional view of a double pusher suture clip locking and severing catheter distal end with a suture clip being released from a collet cage according to one embodiment of the invention.

Figure 147:
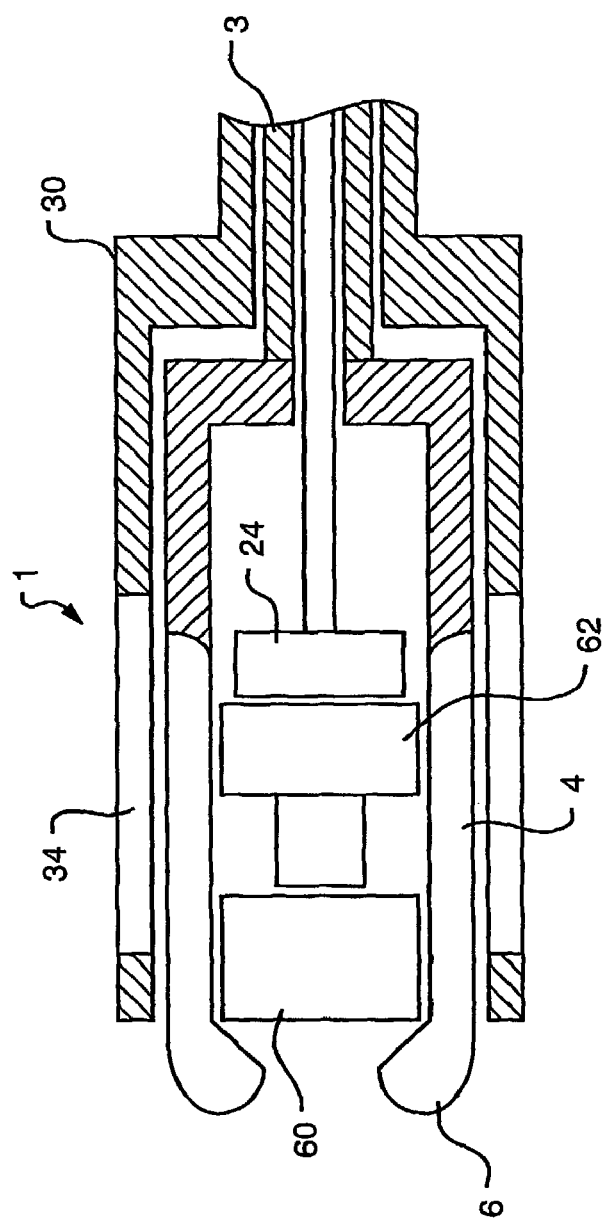

FIG. 147 is an side sectional view of a single pusher suture clip locking and severing catheter distal end loaded with a suture clip plug and suture clip ring according to another embodiment of the invention.

Figure 148:
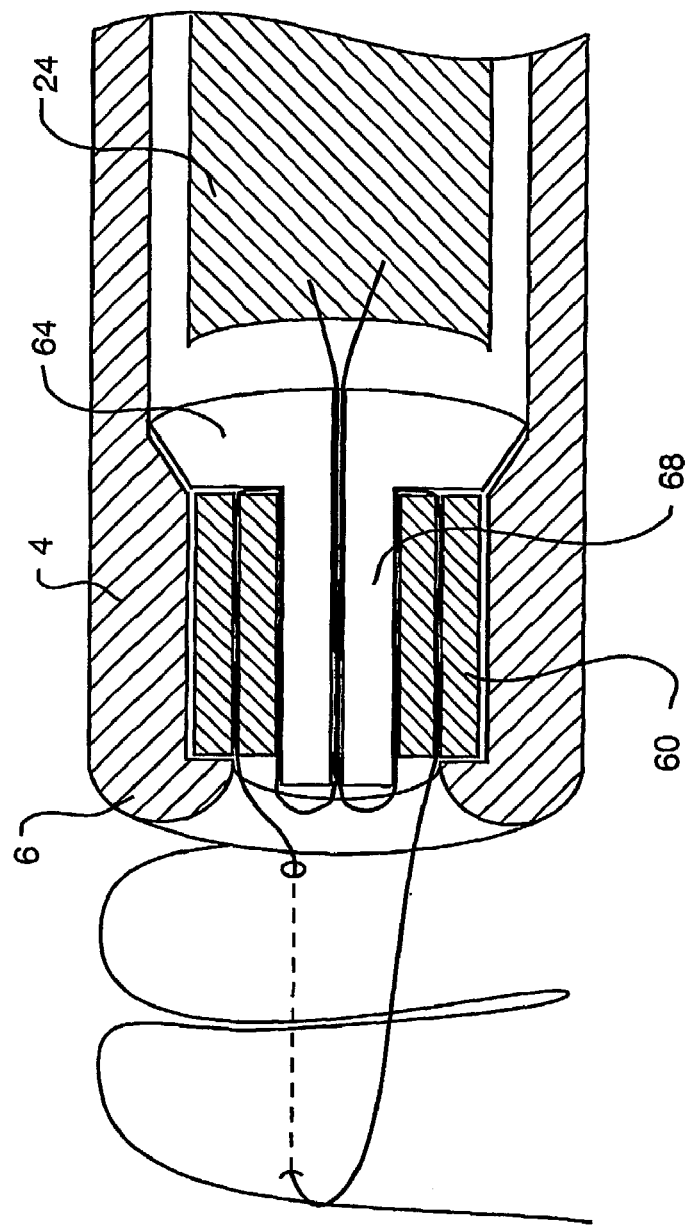

FIG. 148 is a side sectional view of a single pusher suture clip locking and severing catheter distal end loaded with a convex head suture clip plug and suture clip ring according to one embodiment of the invention.

Figure 149:
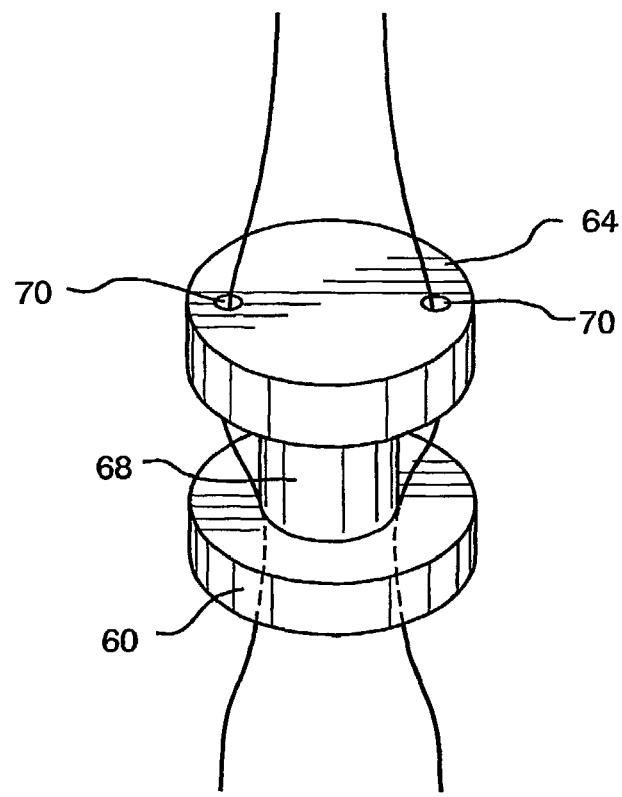

FIG. 149. is a top perspective view of an assembled suture lock plug and suture lock ring according to another embodiment of the invention.

Figure 150:
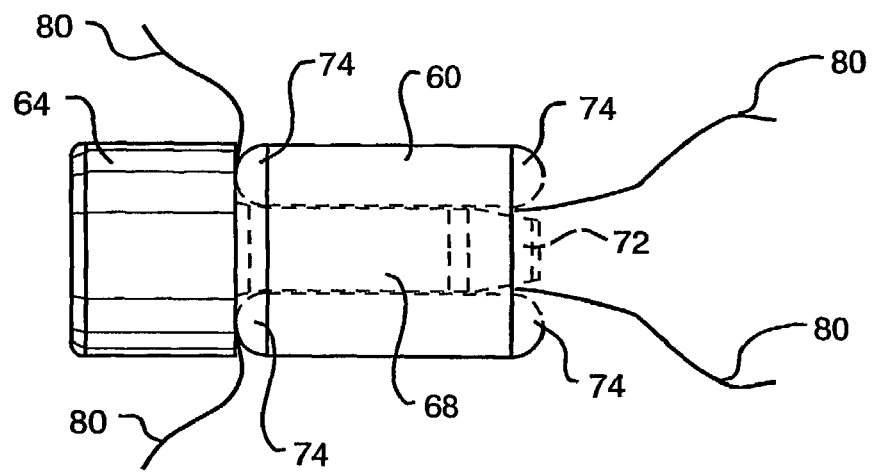

FIG. 150 is a sectional view of an assembled suture lock plug and suture lock ring according to a further embodiment of the invention.

Figure 151:
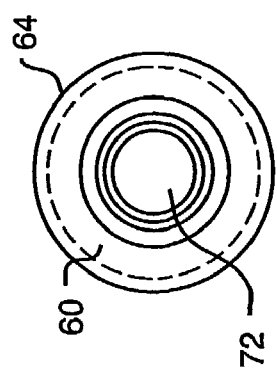

FIG. 151 is an end view of an assembled suture lock plug and suture lock ring according to a further embodiment of the invention.

Figure 152:
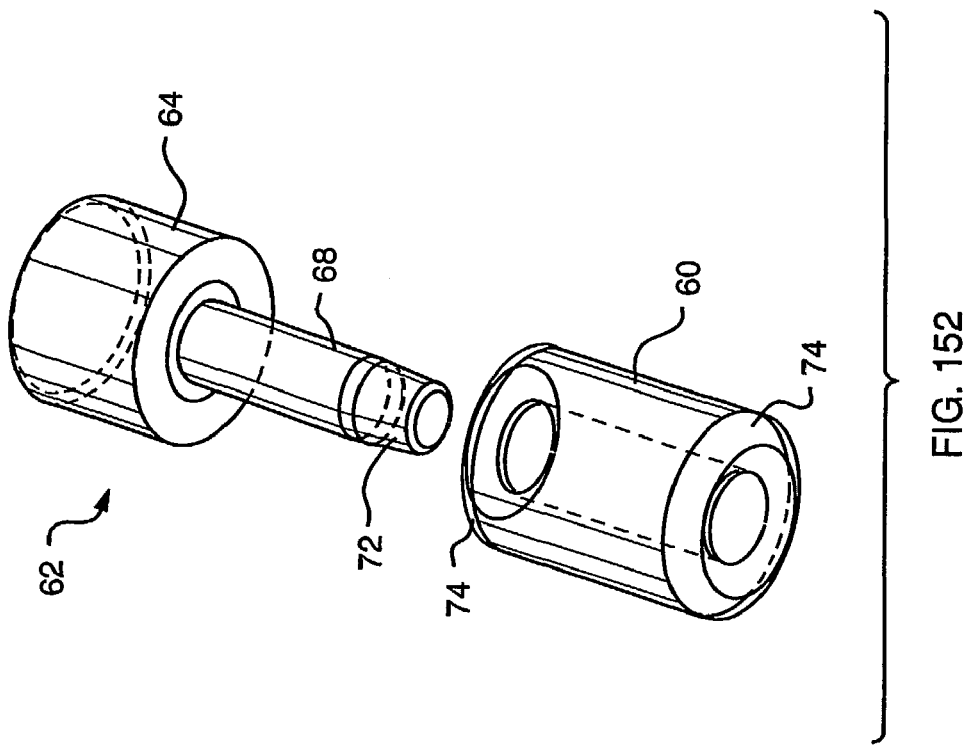

FIG. 152 is a perspective view of an unassembled suture lock plug and suture lock ring according to a further embodiment of the invention.

Figure 153:
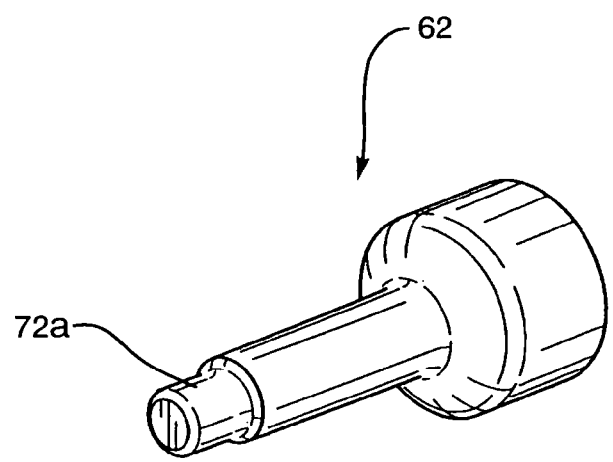

FIG. 153 is a perspective view of a suture lock plug according to a yet further embodiment of the invention.

FIG. 154 is a side sectional view of a suture clip loading device according to one embodiment of the invention.

FIG. 155 is an end view of a suture clip loading device according to one embodiment of the invention.

FIG. 156 is a perspective view of an unassembled suture clip loading device according to one embodiment of the invention.

Figure 157:
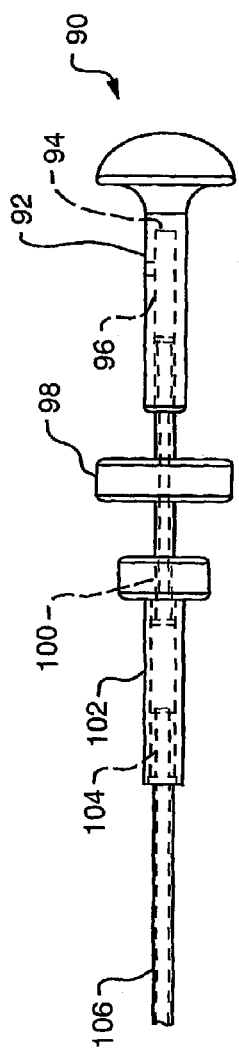

FIG. 157 is a side sectional view of a control handle according to a further embodiment of the invention.

Figure 158:
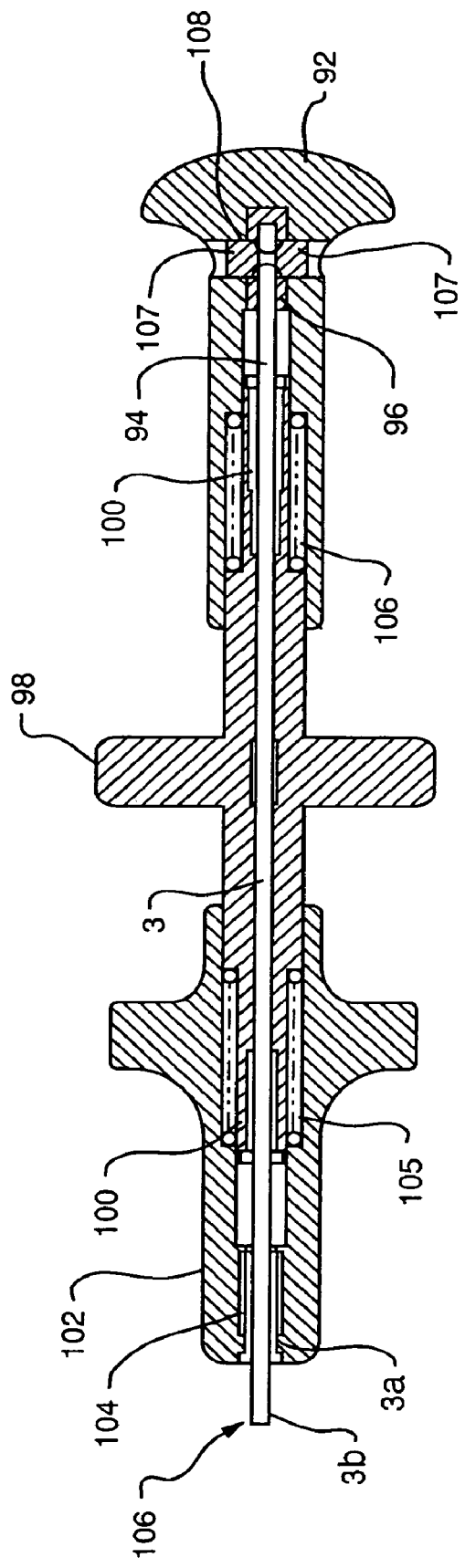

FIG. 158 is a side sectional view of a control handle according to a yet further embodiment of the invention.

Figure 159:
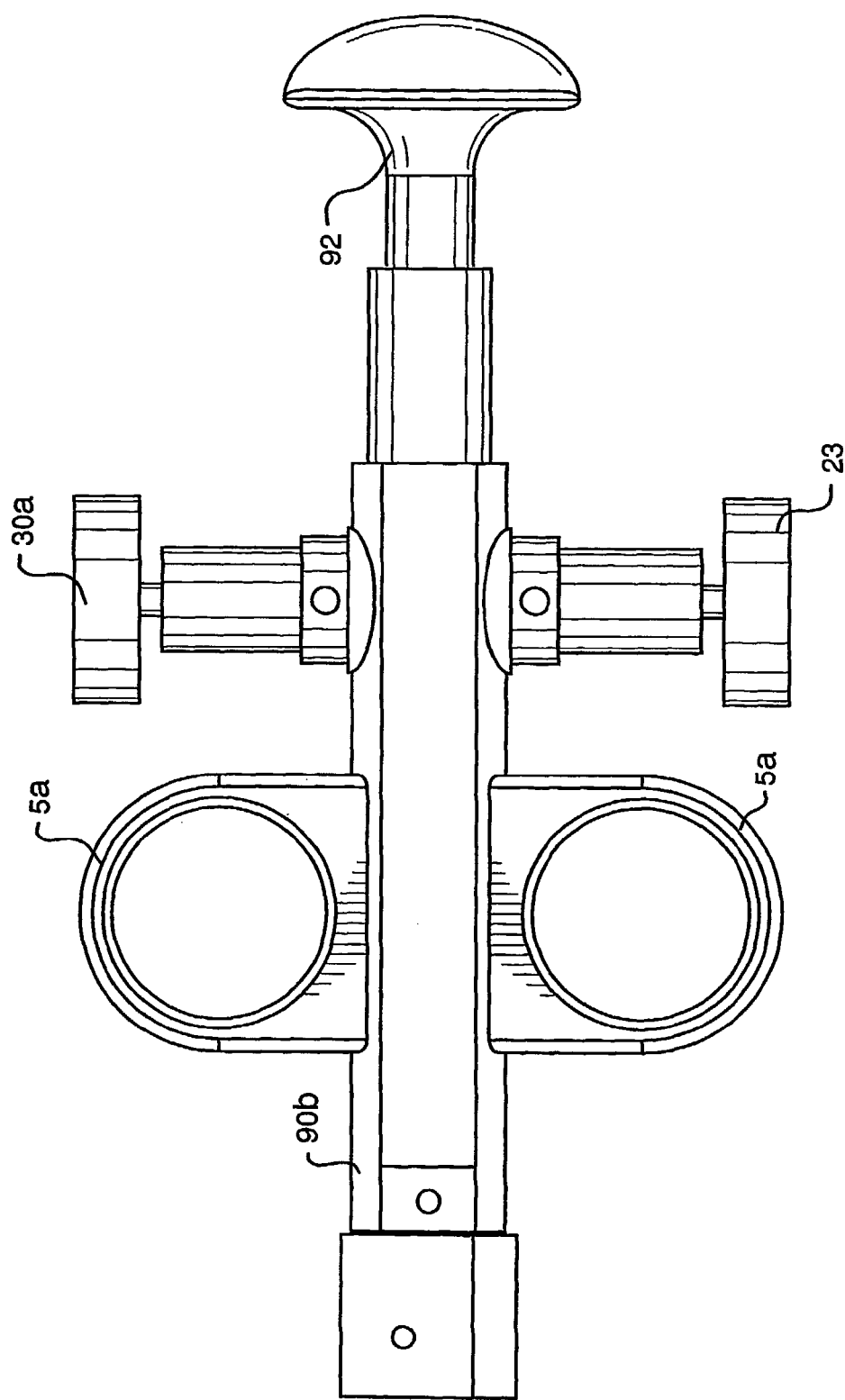

FIG. 159 is a plan view of a single action control handle according to a still further embodiment of the invention.

Figure 160:
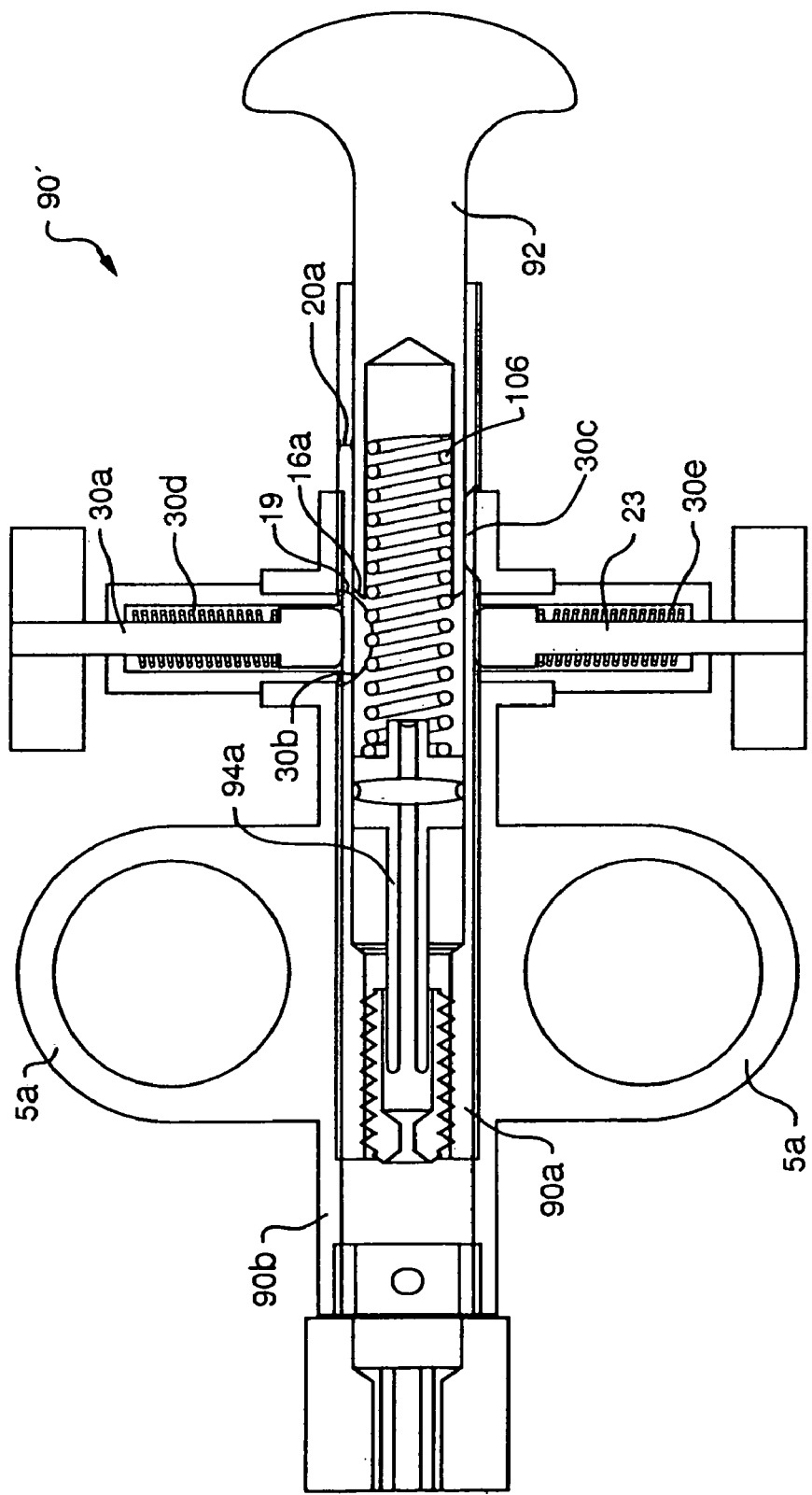

FIG. 160 is a sectional view of a single action control handle according to a still further embodiment of the invention.

Figure 161:
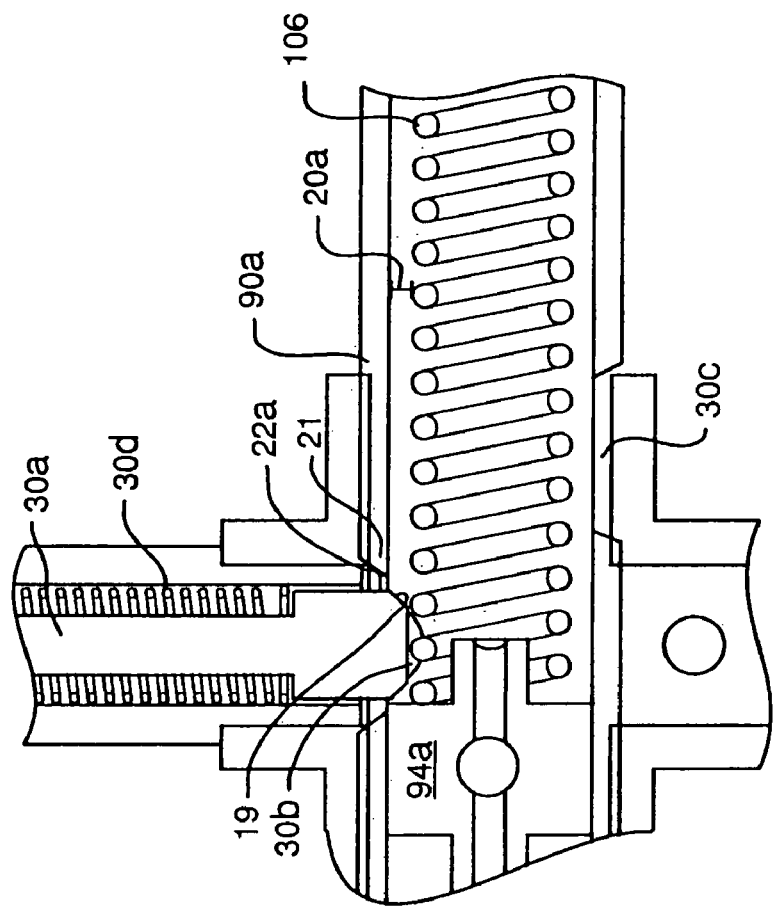

FIG. 161 is a partial sectional view of a single action control handle according to a still further embodiment of the invention.

Figure 162:
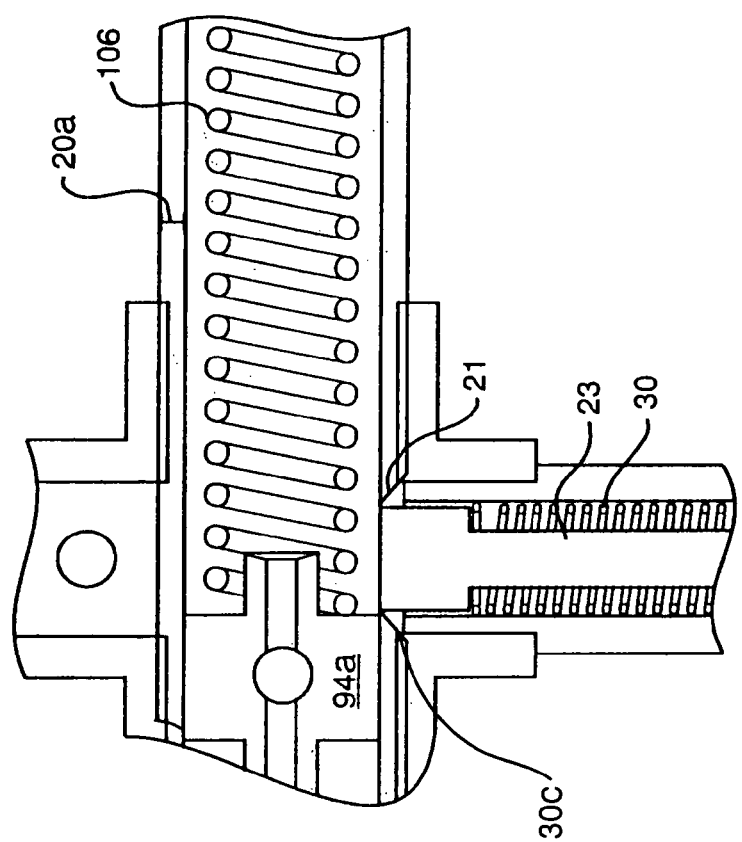

FIG. 162 is a partial sectional view of a single action control handle according to a still further embodiment of the invention.

Figure 163:
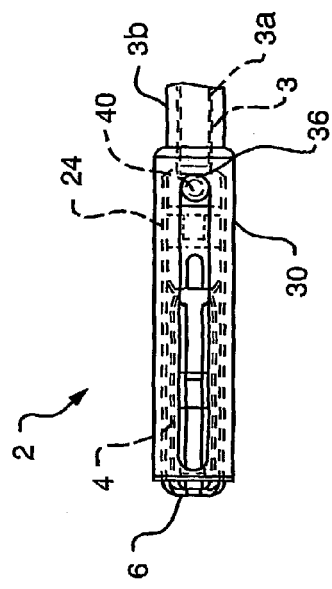

FIG. 163 is a side sectional view of a single pusher suture clip locking and severing collet cage according to a further embodiment of the invention.

Figure 164:
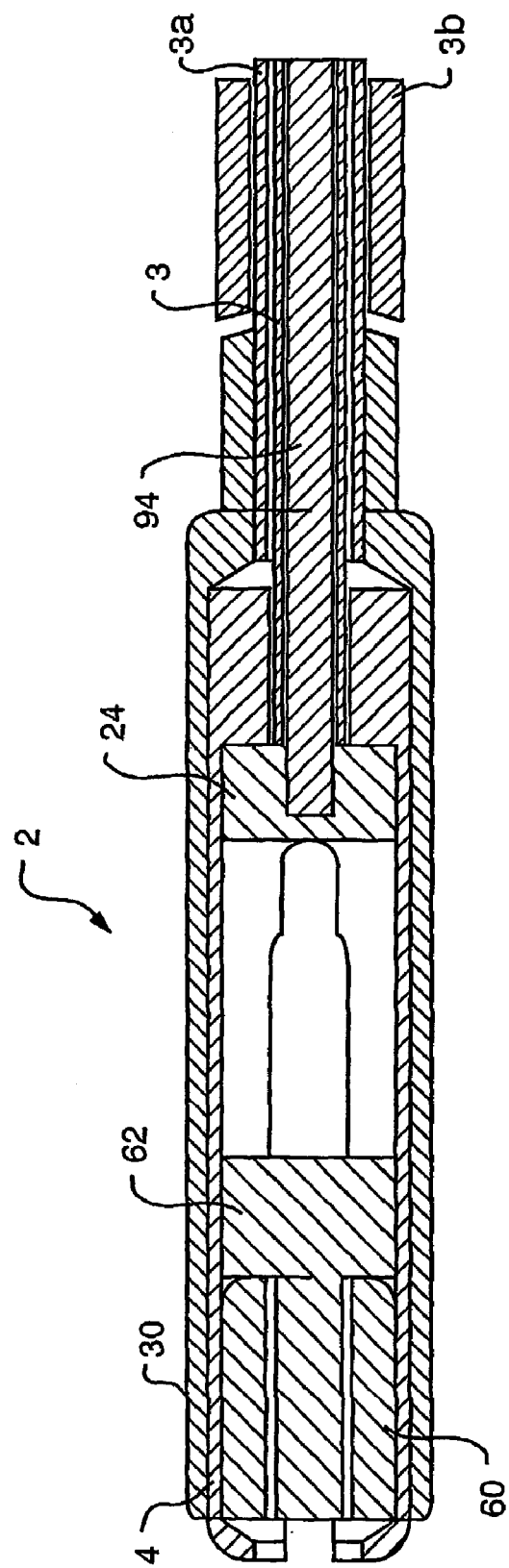

FIG. 164 is a side sectional view of a single pusher suture clip locking and severing collet cage according to a yet further embodiment of the invention.

Figure 165:
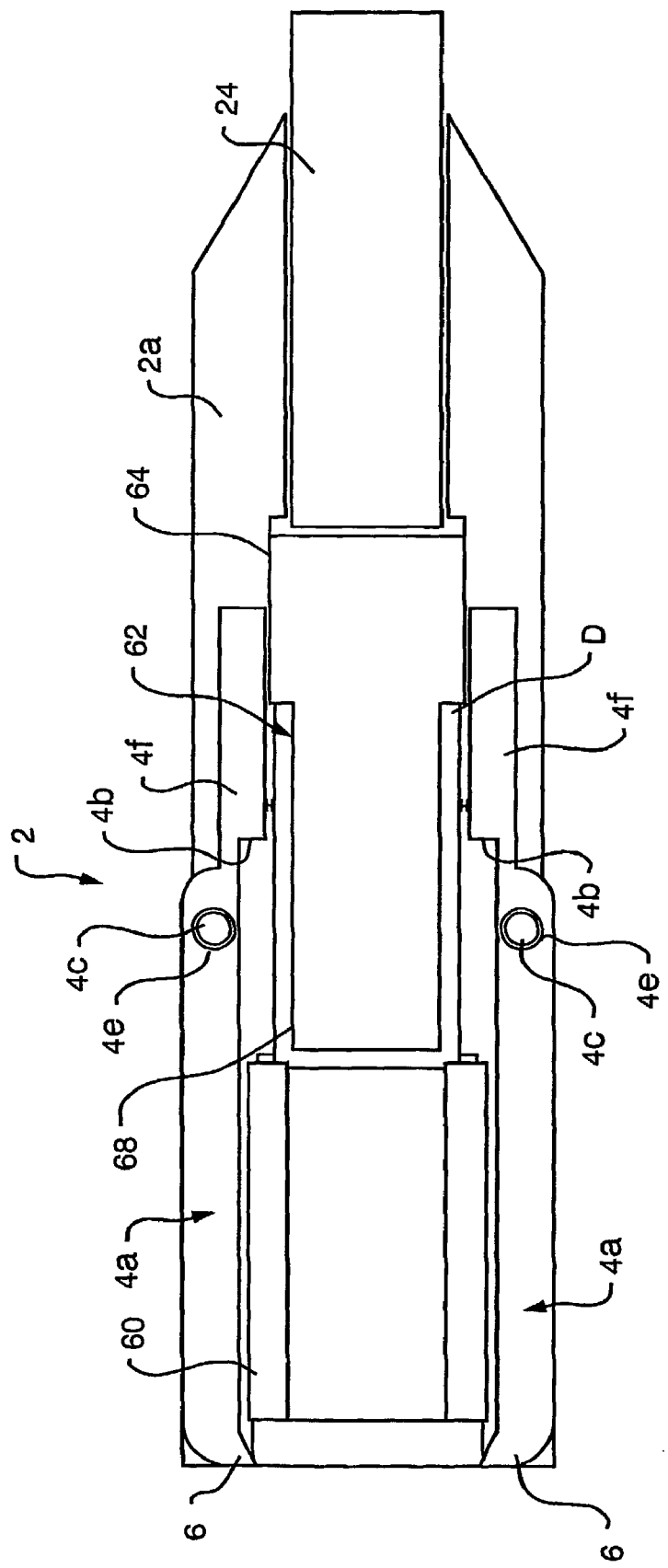

FIG. 165 is a side sectional view of a single pusher suture clip locking and severing collet cage with a pre-cinched suture clip assembly according to a still further embodiment of the invention.

Figure 166:
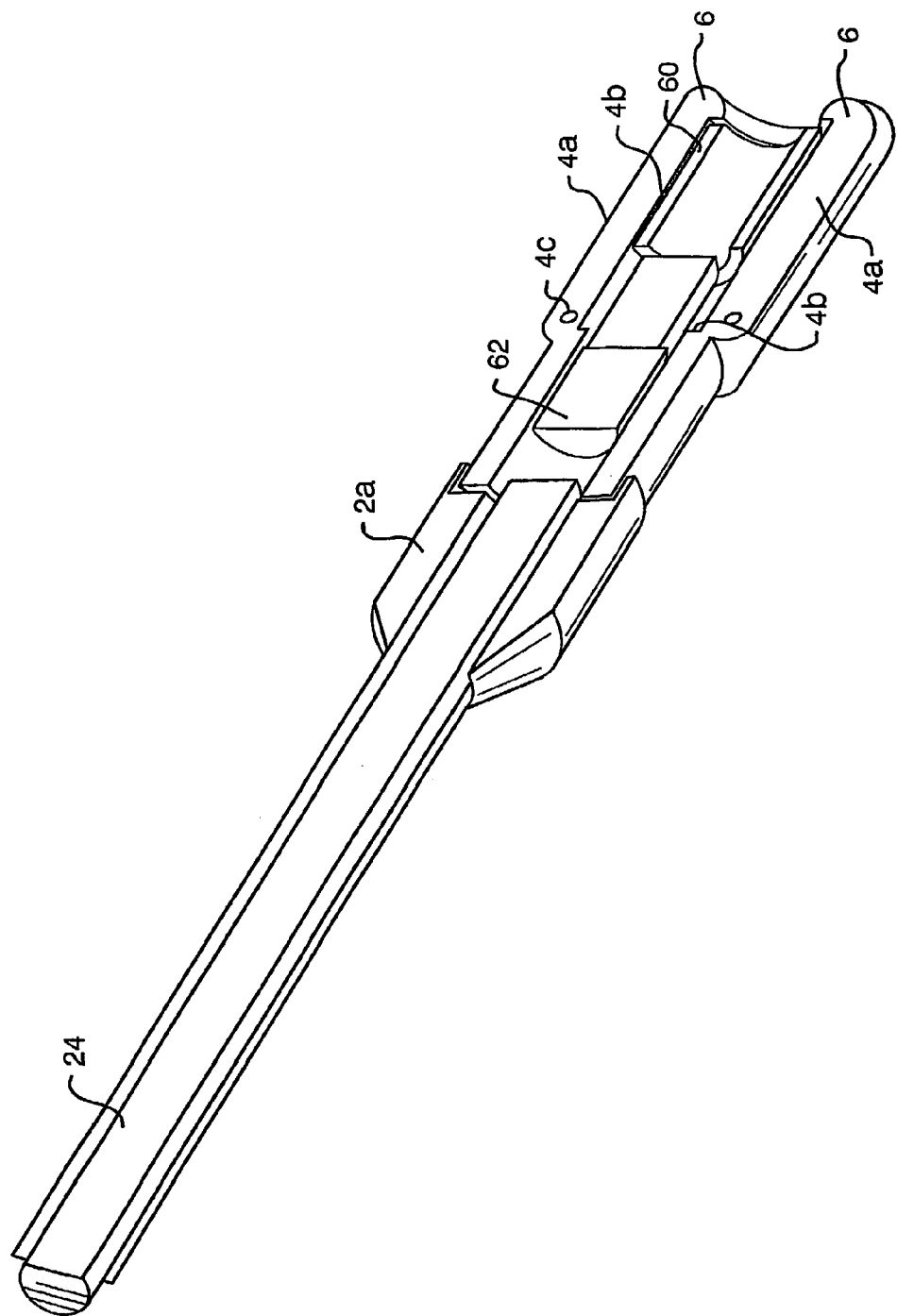

FIG. 166 is a top perspective sectional view of a single pusher suture clip locking and severing device according to a still further embodiment of the invention.

Figure 167:
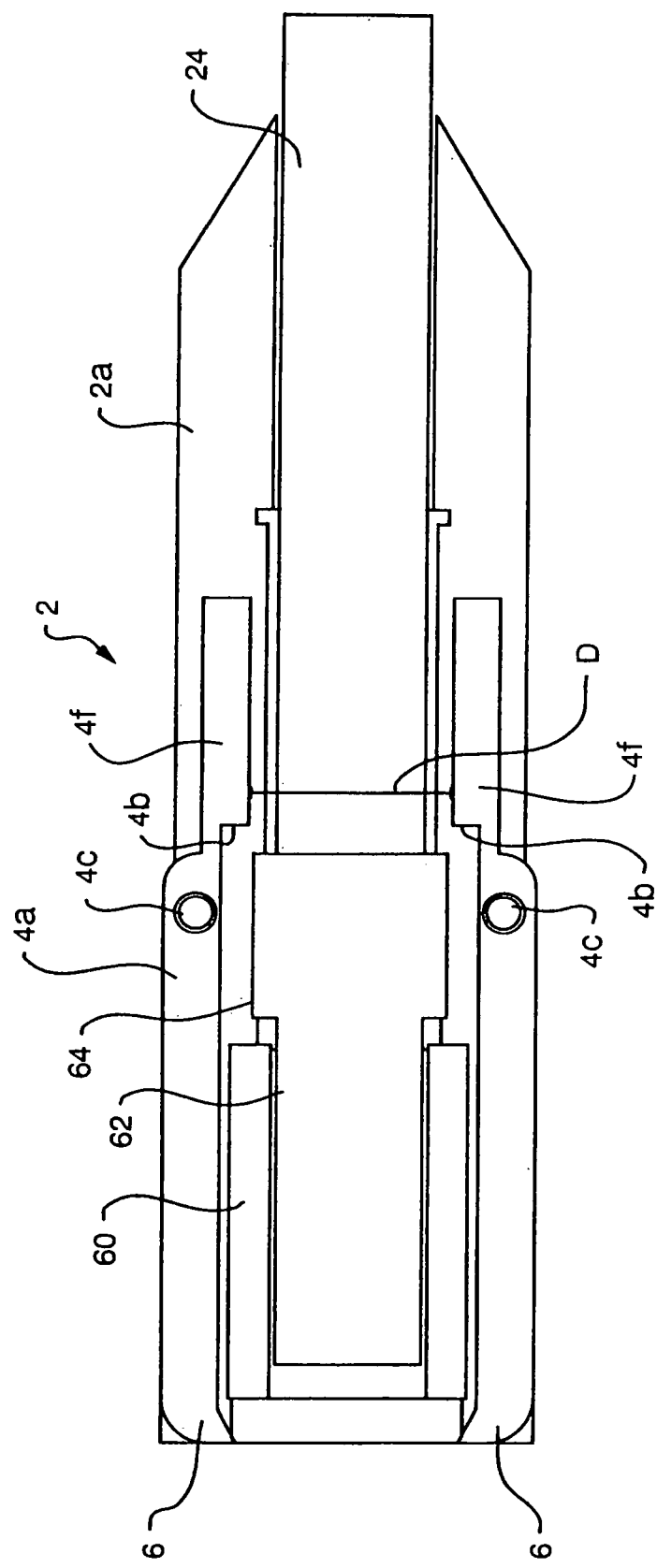

FIG. 167 is a side sectional view of a single pusher suture clip locking and severing collet cage with a cinched suture clip assembly according to a still further embodiment of the invention.

Figure 168:
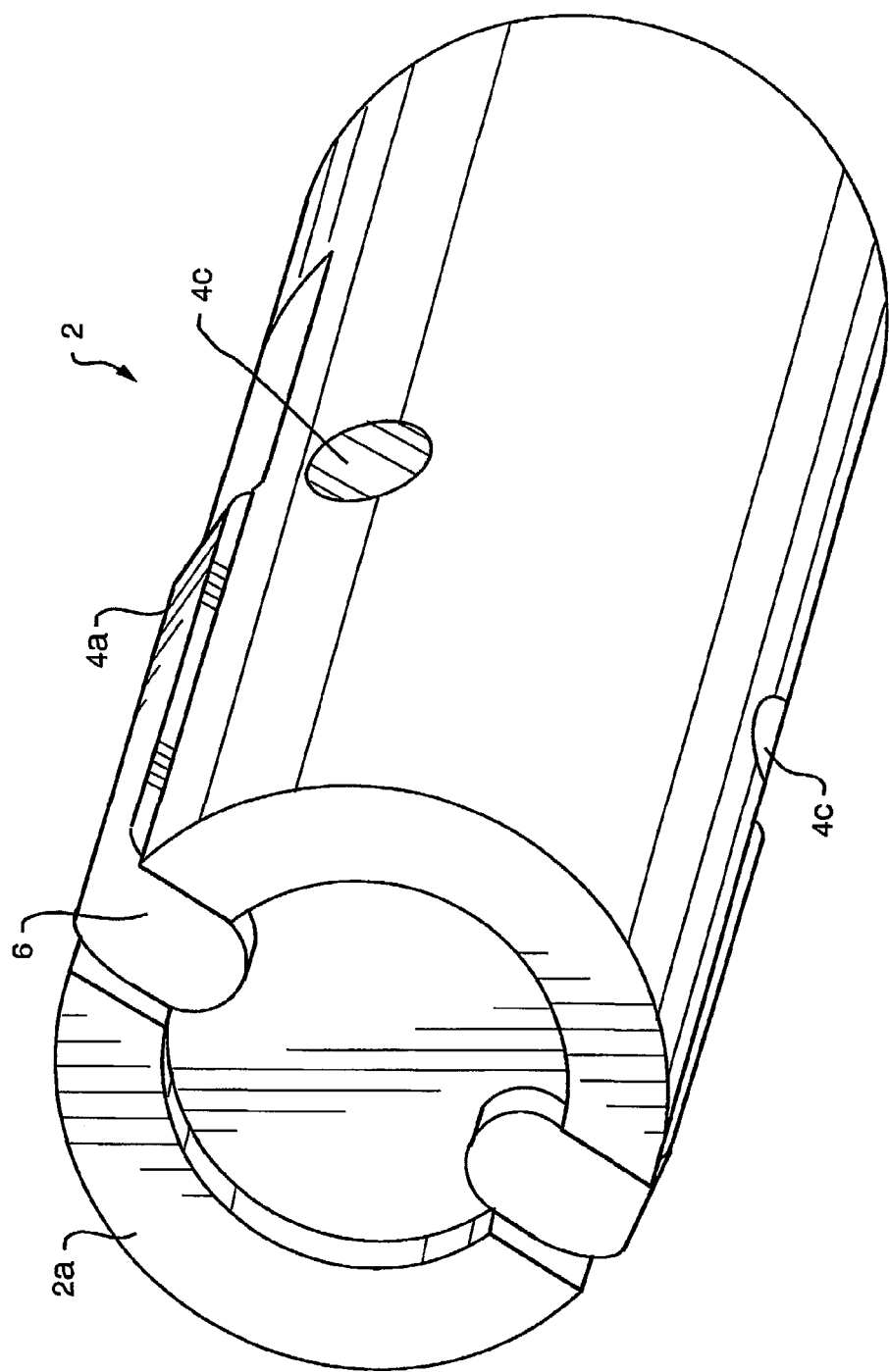

FIG. 168 is a front perspective view of a single pusher suture clip locking and severing device according to a still further embodiment of the invention.

Figure 169:
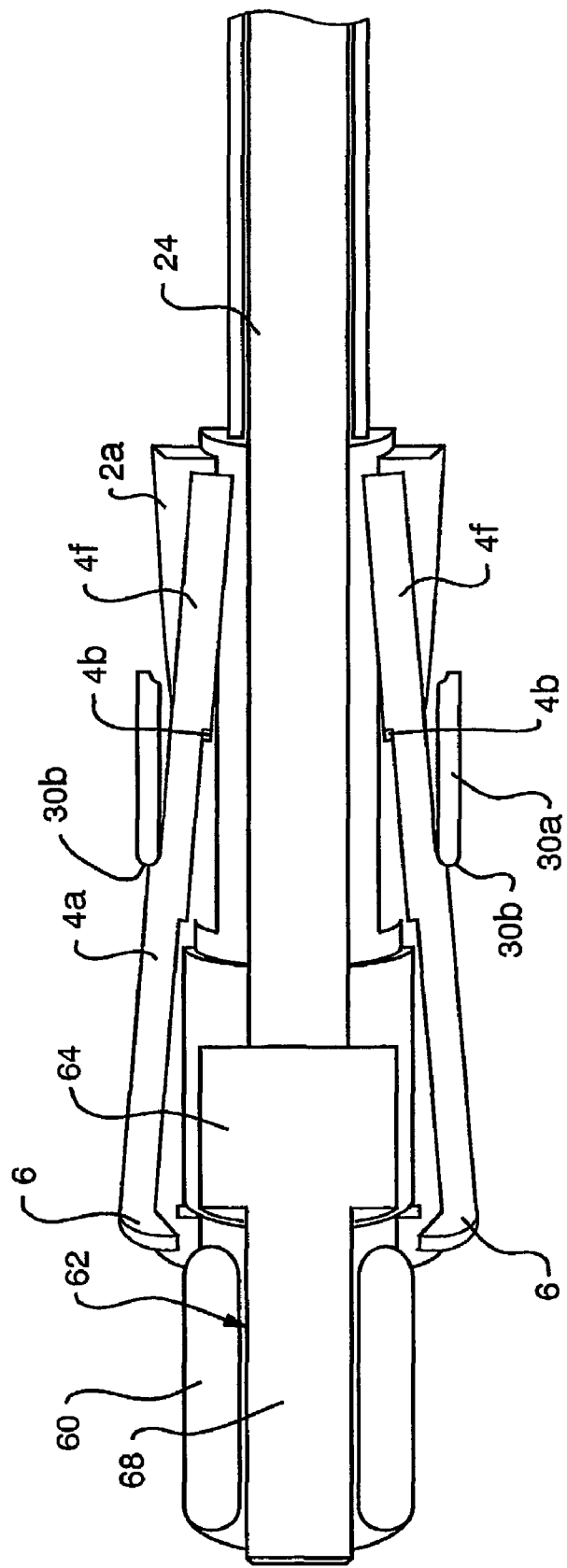

FIG. 169 is a side sectional view of a single pusher suture clip locking and severing device with a cinched suture clip assembly and a pivot ring according to yet another embodiment of the invention.

Figure 170:
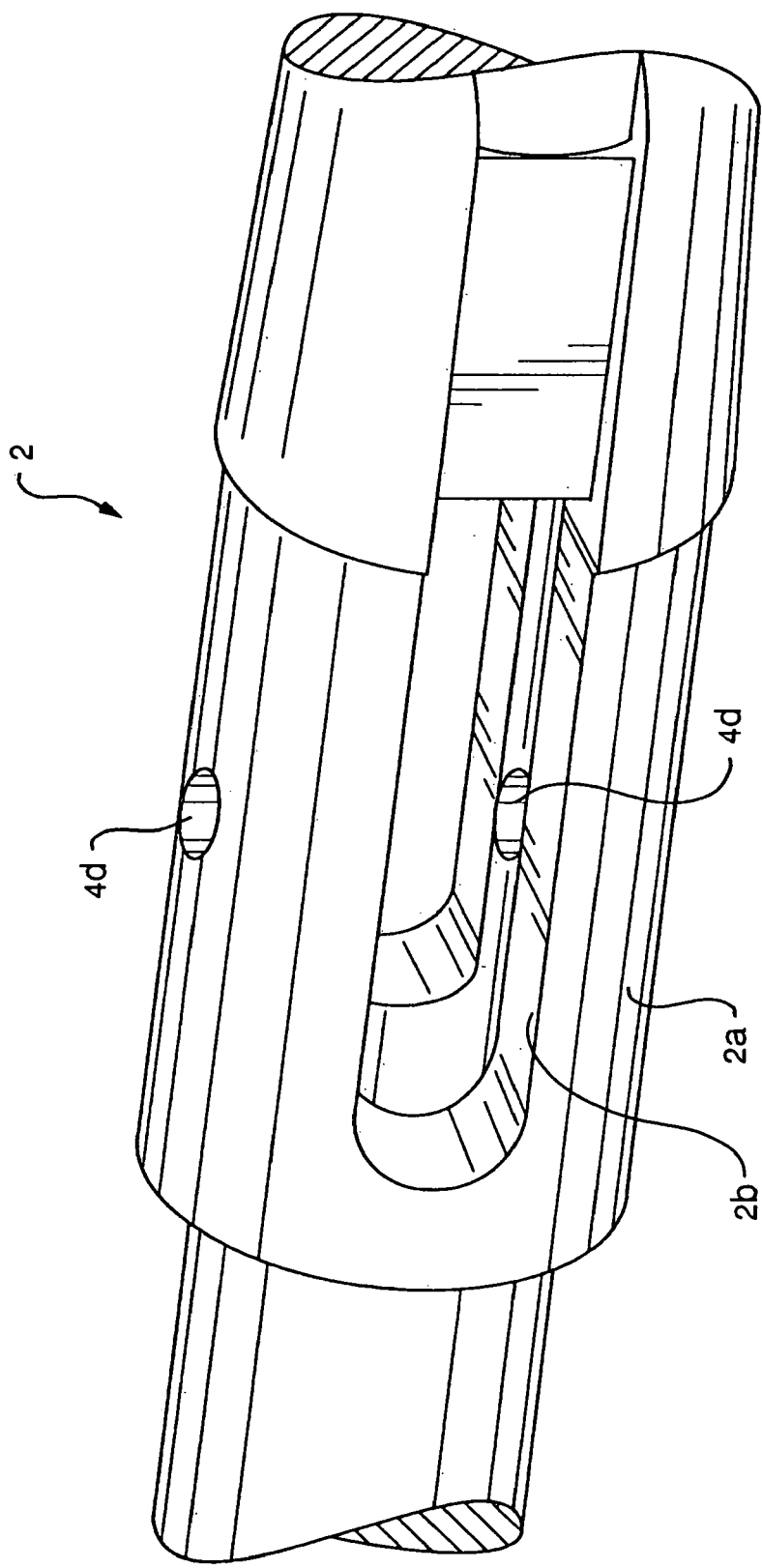

FIG. 170 is a side perspective view of a collet cage body according to a still further embodiment of the invention.

Figure 171:
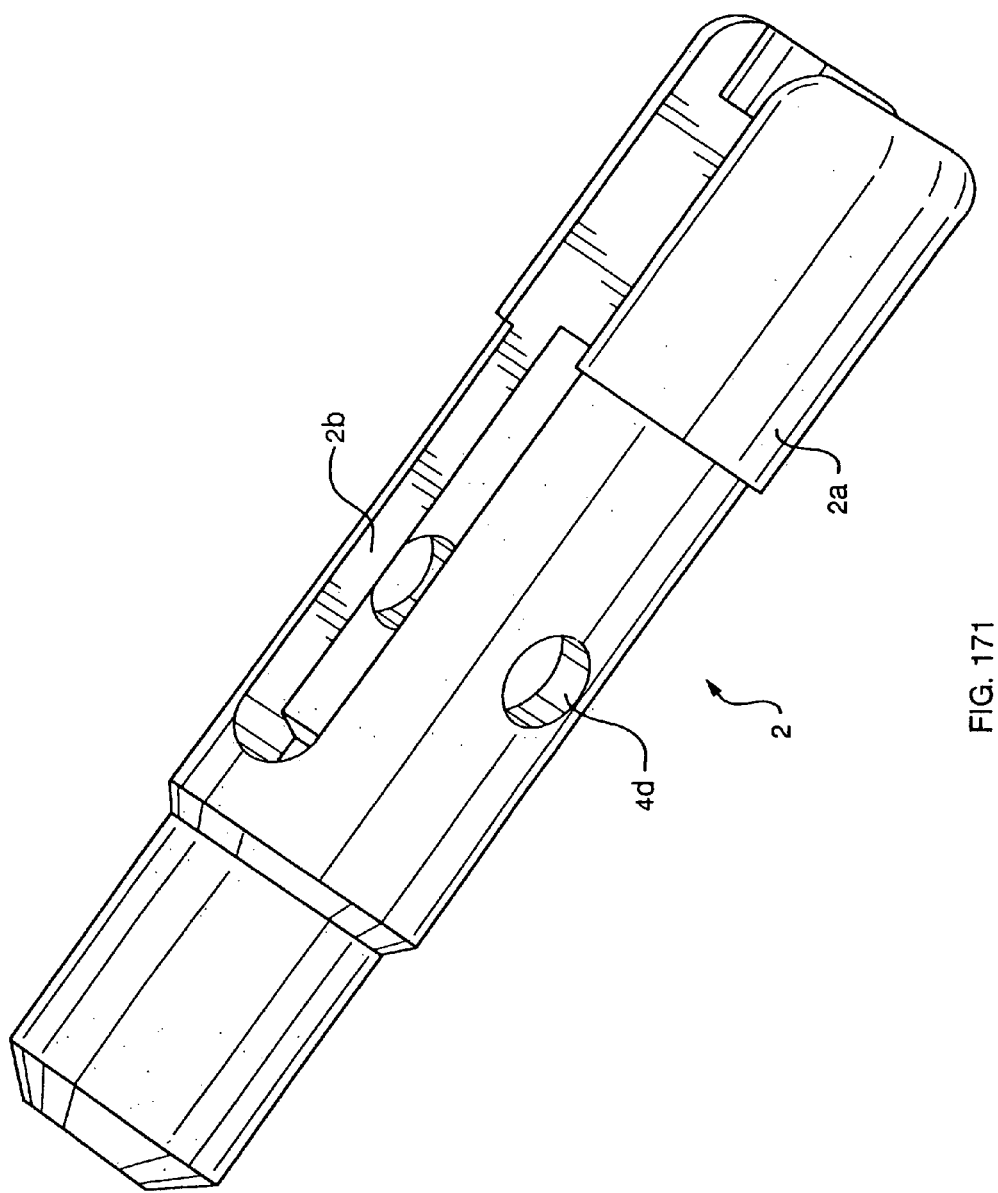

FIG. 171 is a top perspective view of a collet cage body according to a still further embodiment of the invention.

FIG. 172 is an end view of a collet cage body according to a still further embodiment of the invention.

FIG. 173 is a side sectional view of a threader according to one embodiment of the invention.

FIG. 174 is an end view of a threader according to one embodiment of the invention.

FIG. 175 is a perspective view of a threader according to one embodiment of the invention.

FIG. 176 is a side sectional view of a vacuum-actuated threader according to another embodiment of the invention.

FIG. 177 is a front elevational view of a vacuum-actuated threader according to another embodiment of the invention.

FIG. 178 is a side sectional view of a vacuum-actuated threader according to a further embodiment of the invention.

FIG. 179 is a front elevational view of a vacuum-actuated threader according to a further embodiment of the invention.

DETAILED DESCRIPTION OF THE PREFERRED EMBODIMENT

Figure 1:
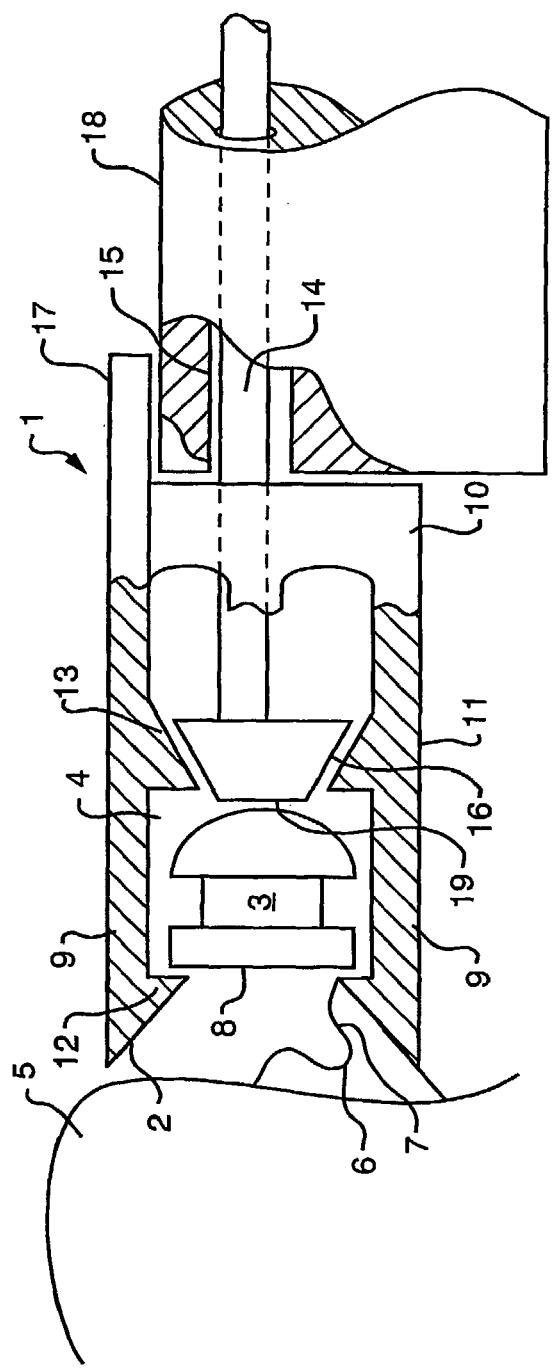
FIG. 1 is a side partial cutaway sectional view of an endoscope with an attached suture clip delivery/locking device and suture clip in a first position according to one embodiment of the invention.
Figure 1A:
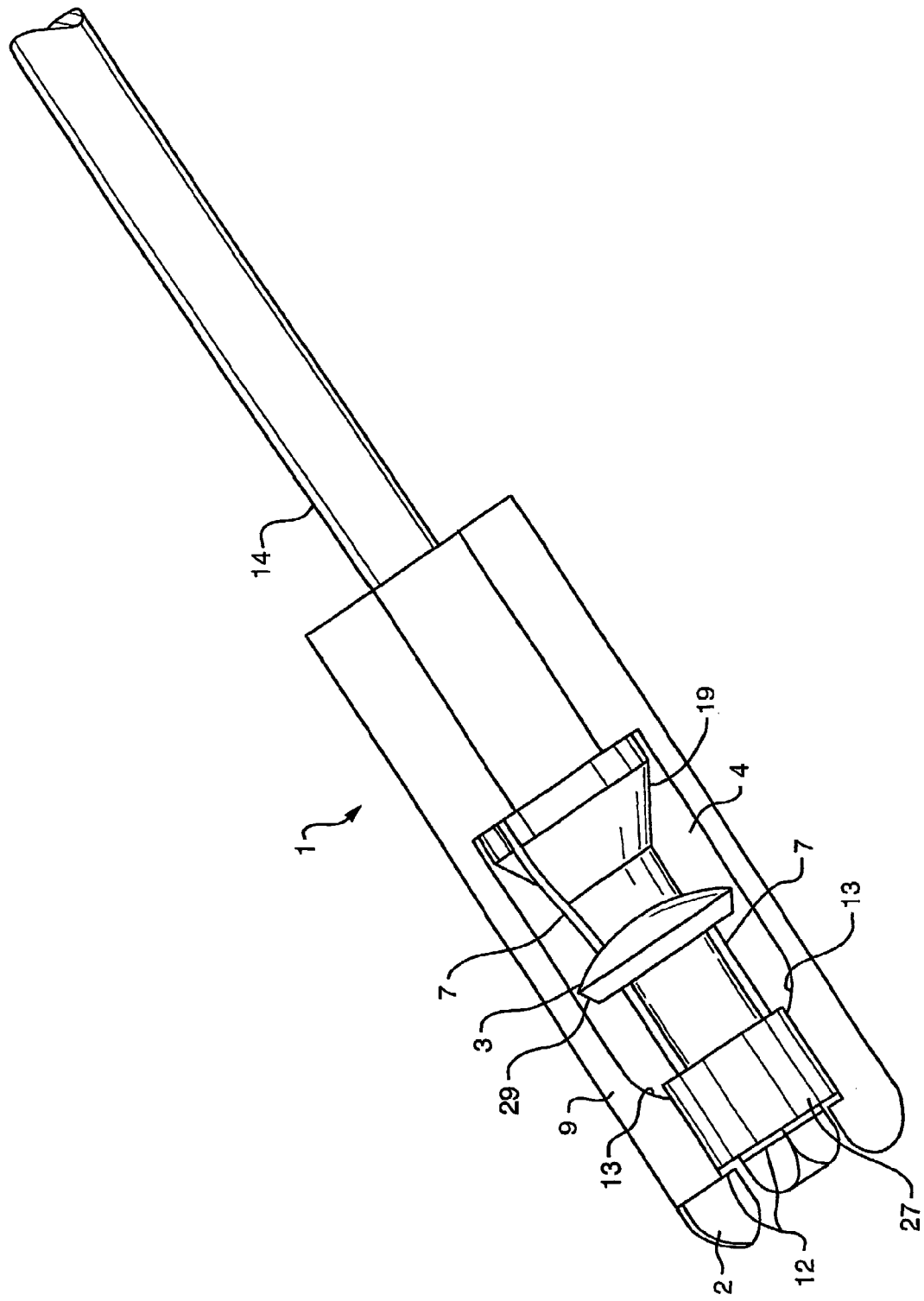
FIG. 1a is a perspective view of a suture clip delivery/locking device and suture clip in a first position according to another embodiment of the invention.
Figure 1D:
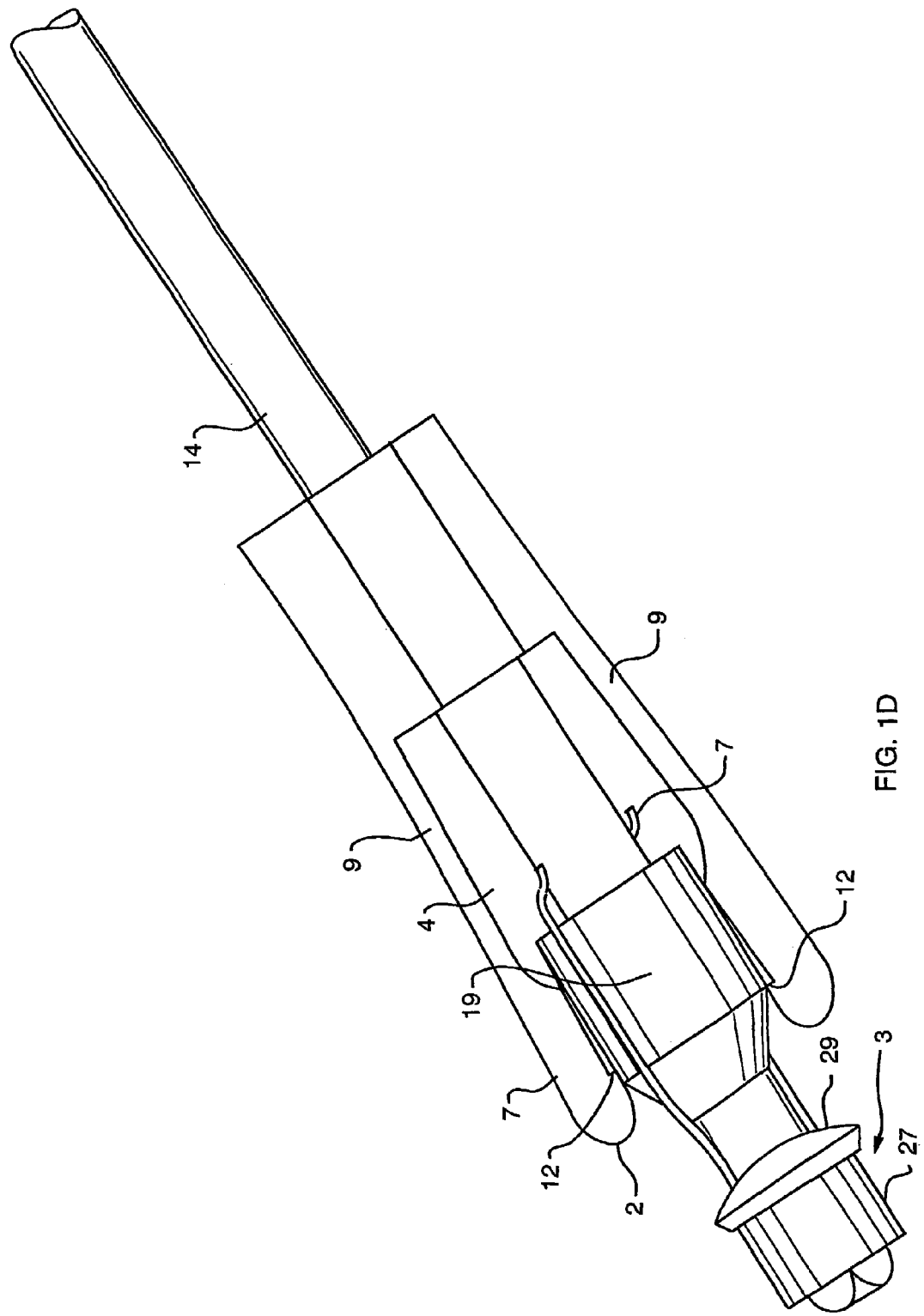
FIG. 1d is a perspective view of a suture clip delivery/locking device and suture clip in an second open position according to another embodiment of the invention.
Figure 2A:
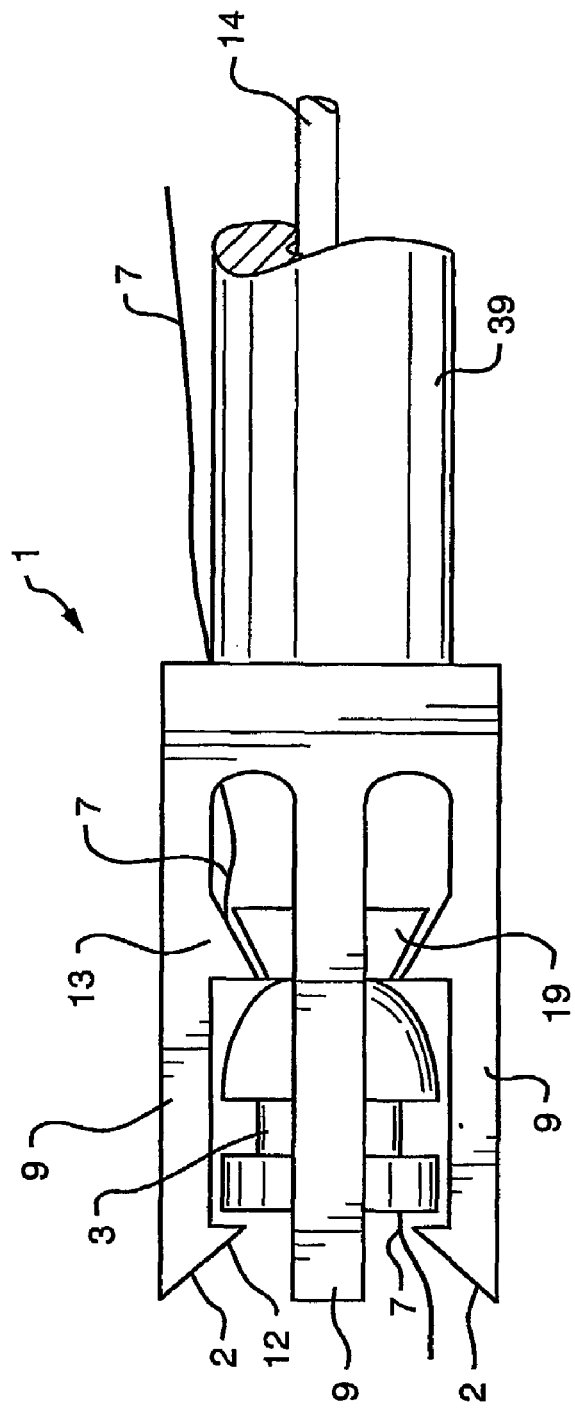
FIG. 2a is a side elevational view of a catheter with an attached suture clip delivery device and suture clip according to one embodiment of the invention.
Figure 2B:
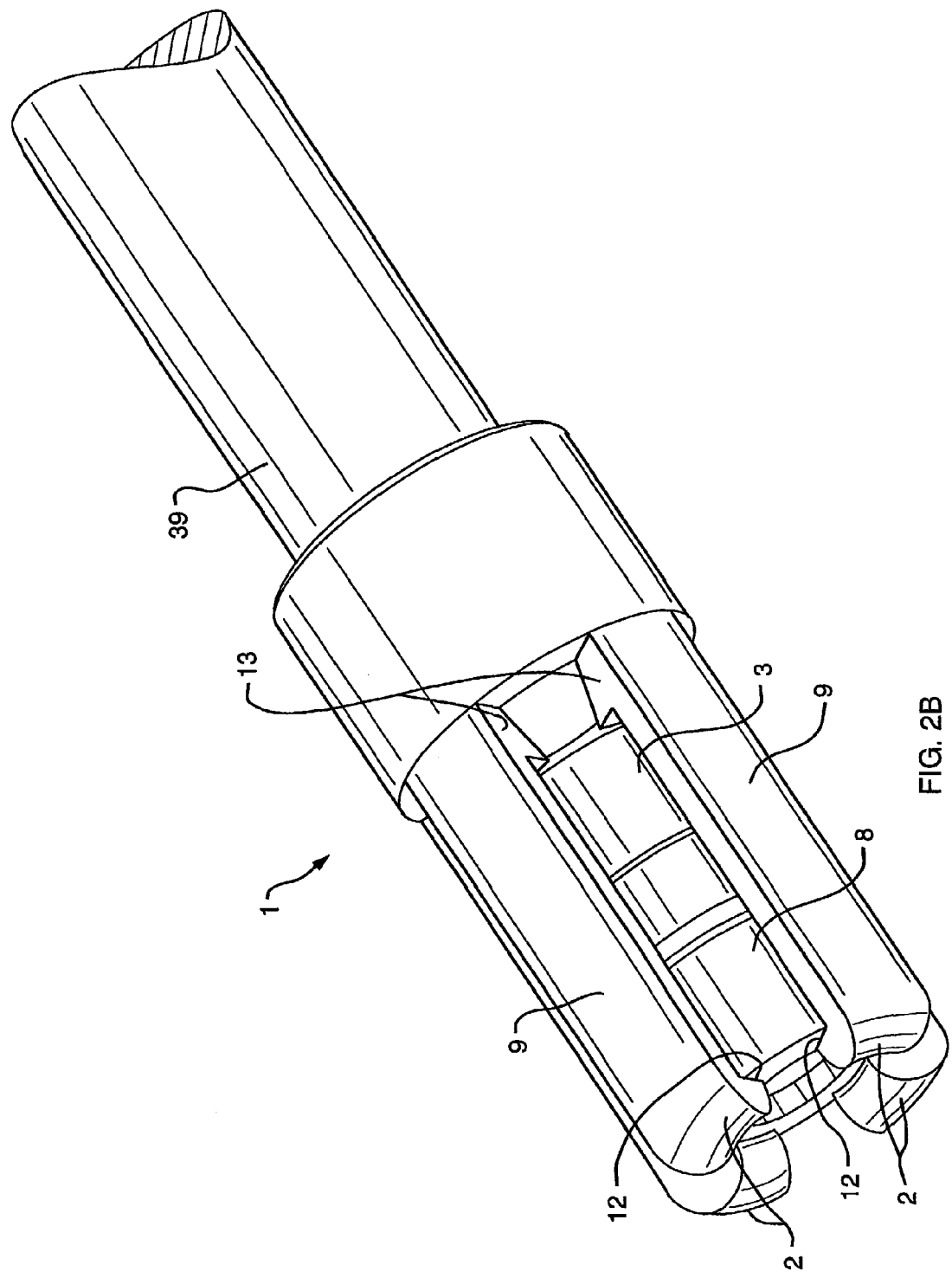
FIG. 2b is a perspective view of a suture clip delivery/locking device and suture clip components in a pre-cinched state according to one embodiment of the invention.
Figure 2C:
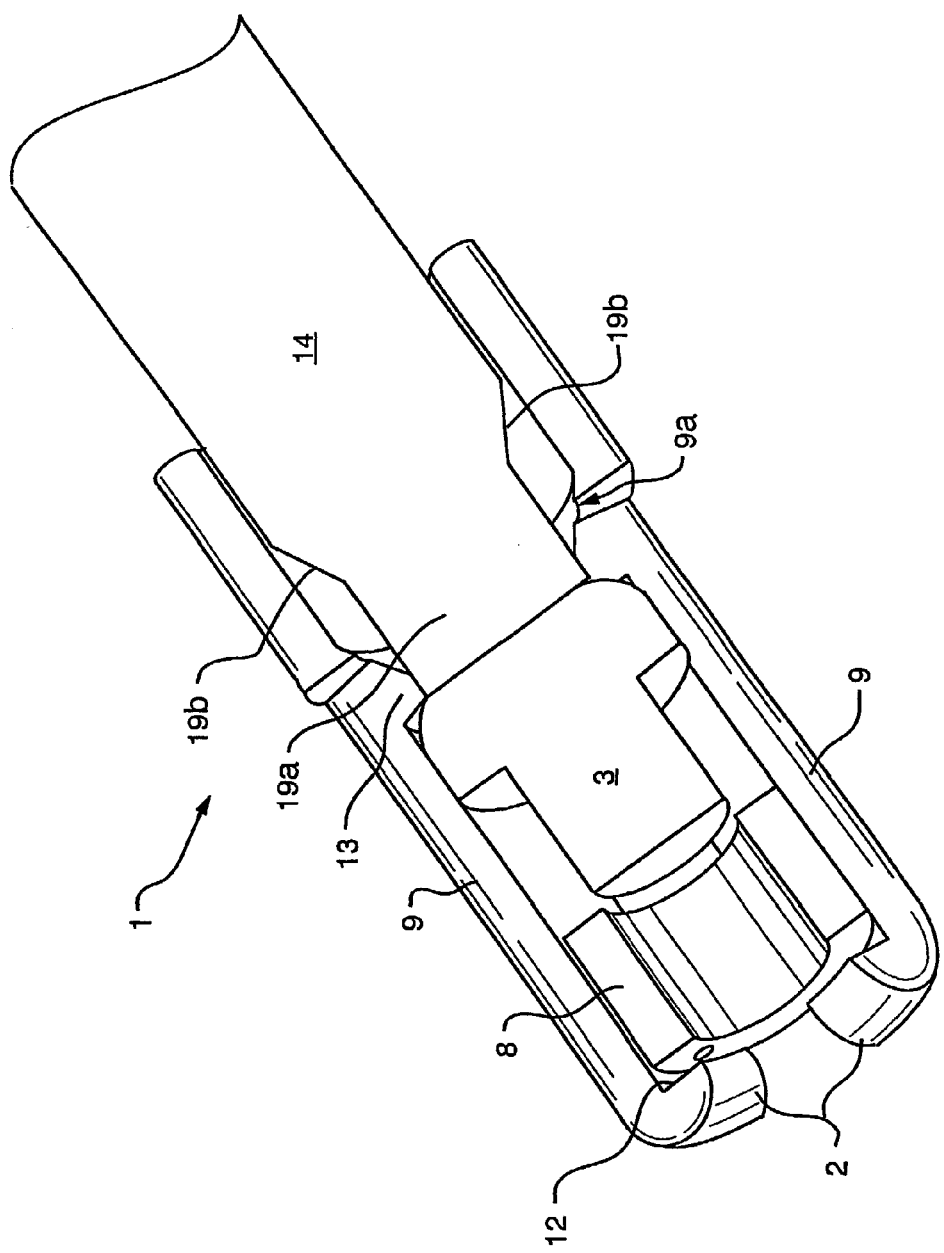
FIG. 2c is a partial sectional view of a suture clip delivery/locking device and suture clip components in a pre-cinched state according to one embodiment of the invention.
Figure 2D:
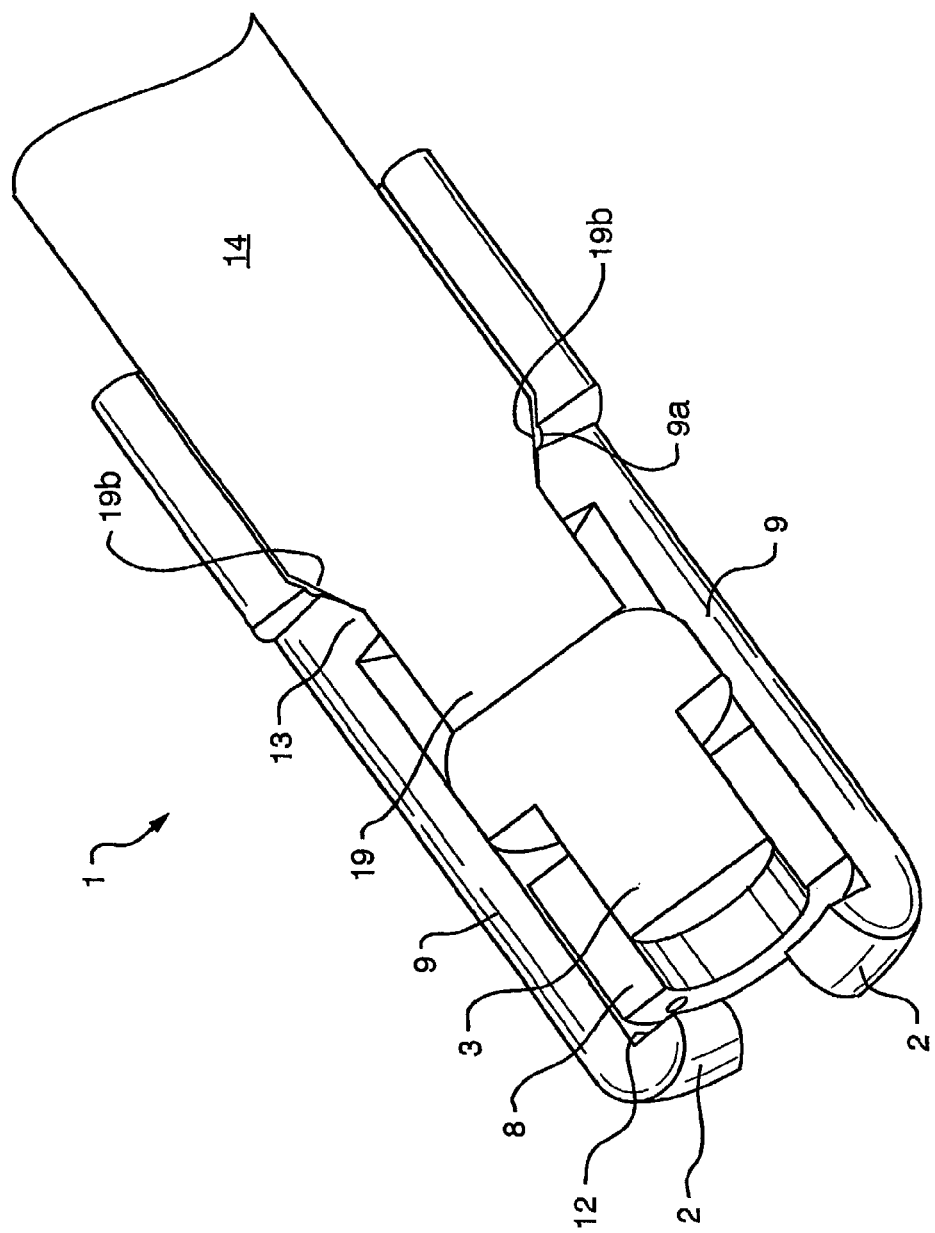
FIG. 2d is a partial sectional view of a suture clip delivery/locking device and suture clip components in a partially cinched state according to one embodiment of the invention.
Figure 2E:
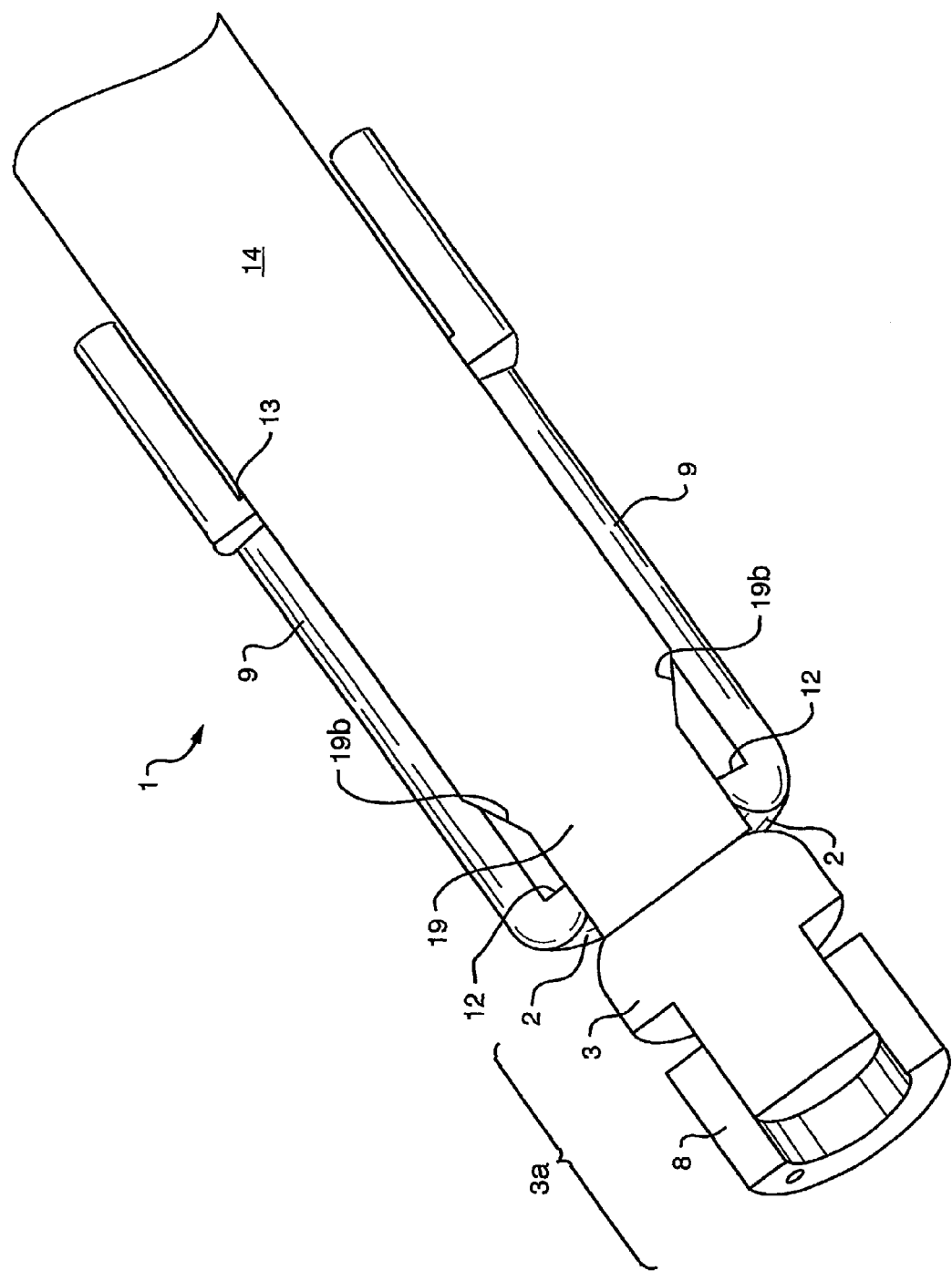
FIG. 2e is a partial sectional view of a suture clip delivery/locking device and suture clip components in a cinched, delivered state according to one embodiment of the invention.
Figure 3:
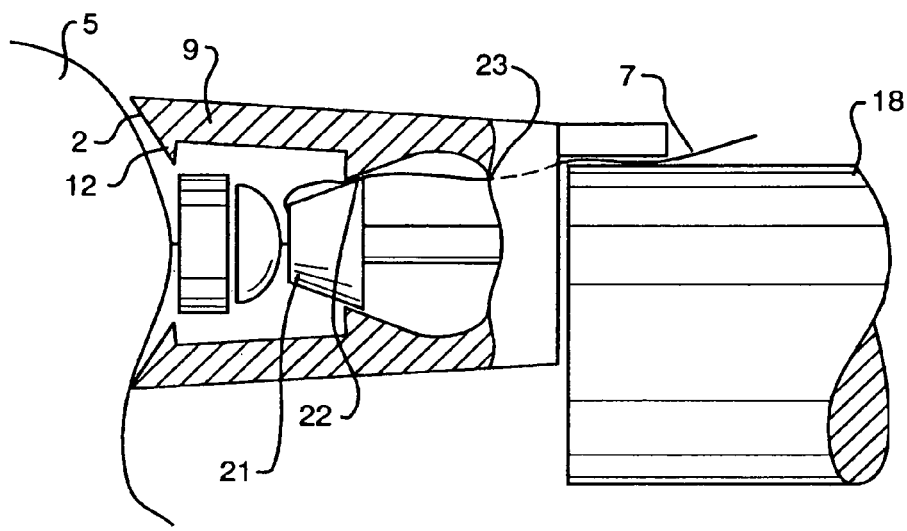
FIG. 3 is a side partial cutaway view of an endoscope with an attached suture clip delivery/locking device and suture clip in a second position according to one embodiment of the invention.

Referring to FIGS. 1-3, a clip delivery/locking device is shown generally as 1. Device 1 is shown in an embodiment designed for mounting to the distal end of an endoscope 18. Device 1 is generally cylindrical in shape and has a flange 17 extending proximally from a proximal end of device 1. Flange 17 is adapted to conform to the contours of the exterior surface of endoscope 18. The combination of the proximal end of device 1 interfacing with the distal end of endoscope 18 and flange 17 interfacing with the exterior surface of endoscope 18 effectively locks device 1 to endoscope 18. Alternatively, device 1 can be secured to endoscope 18 with mechanical fasteners.

Figure 4:
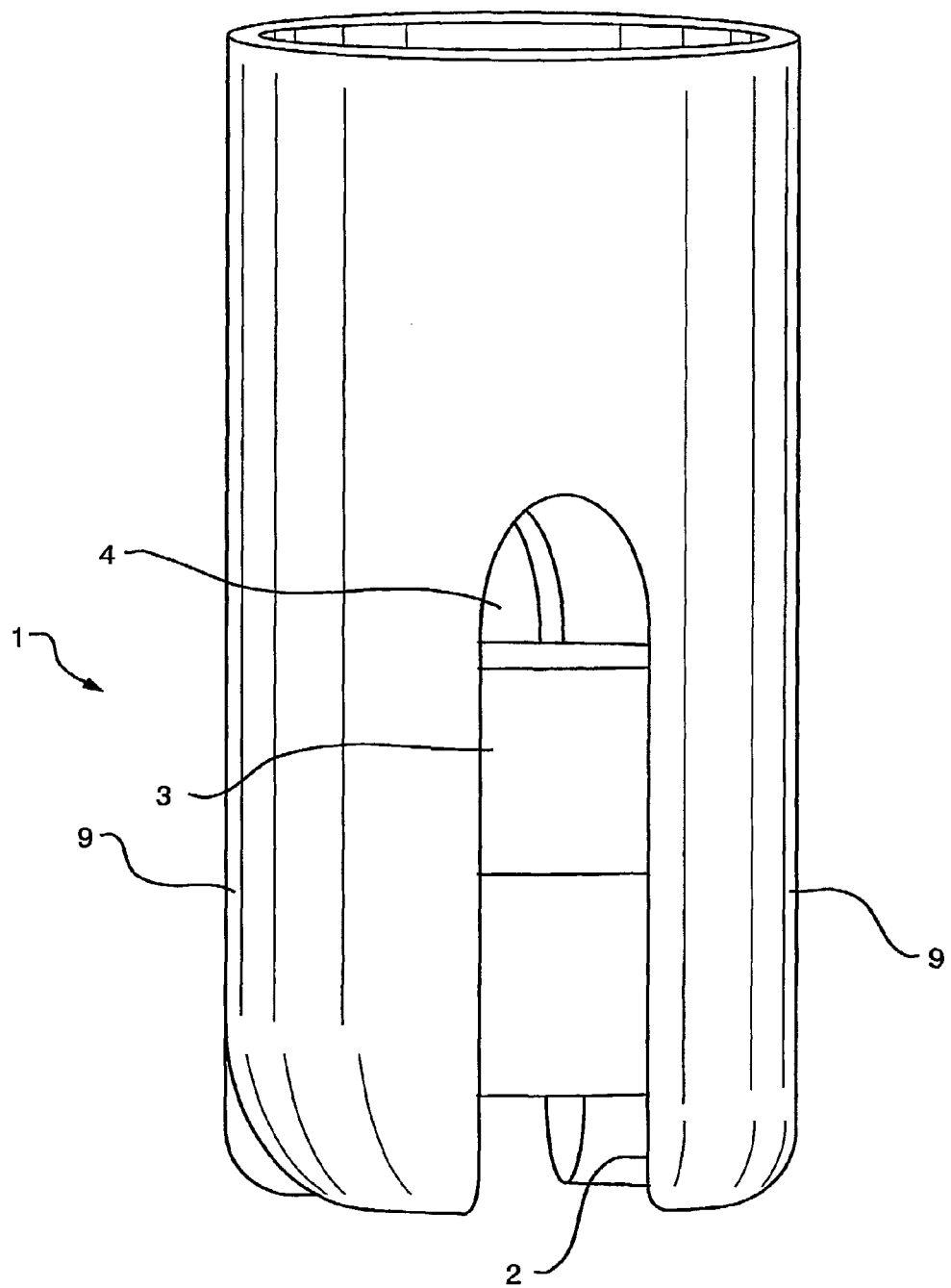
FIG. 4 is a perspective view of a suture clip delivery/locking device and suture clip according to one embodiment of the invention.
Figure 4A:
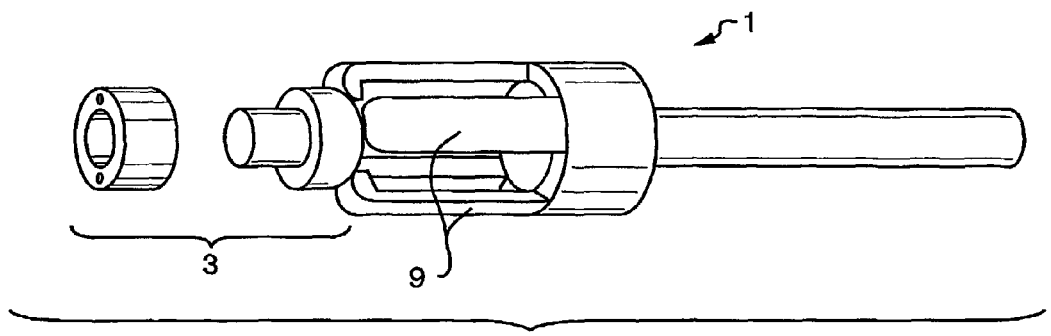
FIG. 4a is a perspective view of a suture clip delivery/locking device and suture clip according to one embodiment of the invention.

Device 1 has portions defining a clip holding chamber 4. A proximal end 4a of holding chamber 4 (shown in FIG. 4) formed on the proximal end of device 1 communicates with holding chamber 4 and a working channel 15 of endoscope 18. Extending distally from a distal end of device 1 are fingers 9 that are oriented on opposite sides of, and partially define, holding chamber 4. Fingers 9 are designed to flex or spring from a first position (shown in FIG. 1) to a second position (shown in FIG. 3) to deliver a suture clip assembly comprising in the illustrated embodiment, a plug 3 and a ring 8. After delivery, fingers 9 spring back to the first position to receive another suture clip assembly. Preferably four fingers 9 are provided (as shown in FIG. 4a) although as little as two fingers 9 are needed. When viewing the distal end of device 1, the distal ends of fingers 9 preferably form a segmented 360° ring.

Fingers 9, in a preferred embodiment, have tapered finger ends 2 with the taper preferably increasing radially outwardly from a proximal end to a distal end of finger ends 2. The proximal ends of finger ends 2 extend radially inwardly of the inner walls of fingers 9 to form distal tangs 12. Distal tangs 12 provide a stop surface against which suture clip 3 can be compressed for manipulation as described in detail below and by which premature release of suture clip 3 is prevented.

Extending radially inwardly from fingers 9 from a point proximal to distal tangs 12 are proximal tangs 13. Proximal tangs 13 are preferably tapered with the taper increasing radially inwardly from a proximal end to a distal end of proximal tangs 13. In an alternate embodiment shown in FIGS. 1a-1d, proximal tangs 13 are radiused portions of the inner walls of fingers 9 that merge into finger ends 2. As described in more detail below, proximal tangs 13 facilitate the movement of fingers 9 from the first position to the second position and act as a cam follower to distal tangs 12.

A pusher 14 is dimensioned and adapted to move freely in an axial direction with the working channel of endoscope 18 and within delivery device 1. Pusher 14 preferably has a frusto-conically shaped distal end 19, the tapered sides of which are dimensioned to contact proximal tangs 13 and translate distal axial movement into radial outward movement of fingers 9.

An alternative to the delivery device shown in FIGS. 1 and 2a is shown in FIGS. 2b-2e. This alternate embodiment can be used with an endoscope or independently as a catheter. In this embodiment, pusher 14 has a reduced diameter, substantially cylindrical distal end 19a. The transition from the diameter of a main body of pusher 14 and distal end 19 forms tapered pusher surface 19b dimensioned to contact proximal tangs 13 to affect the translation of distal axial motion of pusher 14 into radial outward motion of fingers 9. With this embodiment, sutures 7 are severed at shoulder 9a formed at the transition of the main body of delivery device 1 and proximal tangs 13 when tapered pusher surface 19b contacts and slides along proximal tangs 13.

To operate device 1, a suture clip assembly 3a (plug 3 and ring 8), is advanced down endoscope working channel 15 in an open position with pusher 14. Depending on the particular embodiment of suture clip assembly 3a used, any sutures placed inside the subject patient are threaded into any of a variety of apertures in suture clip assembly 3a before suture clip assembly 3a descends down working channel 15.

With suture clip assembly 3a in an open position, sutures 7 ride through ring 8 and plug 3 without becoming locked, The specific procedure used for each embodiment of suture clip assembly 3a described herein will be provided below. Alternatively, the procedure can be initiated with suture clip assembly 3a being premounted in holding chamber 4 before intubation of endoscope 18.

Pusher 14 preferably runs axially along the entire axial length of endoscope 18 so that it can be manipulated from the proximal end of endoscope 18. For the embodiment of device 1 described above and illustrated in FIG. 1, pusher 14 preferably has a frusto-conically shaped pusher distal end 19 the taper of which preferably conforms to the taper of proximal tangs 13. It is to be understood that pusher distal end 19 need not be given any particular shape. For example, a cylindrically shaped pusher distal end 19 can also be used provided that the cross-sectional diameter is sufficiently large to contact with proximal tangs 13 to spread fingers 9.

It is important to the function of device 1 that suture clip 3 have a sufficient diameter, if circular in cross-section, or width, if square or rectangular in cross-section, to contact proximal tangs 13. It is equally important that suture clip 3 has an axial length, in an open position that is no greater than the distance between the opposing surfaces of distal tangs 12 and proximal tangs 13.

Suture clip 3 is urged into device 1 until contact is made with proximal tangs 13. Force is then applied to pusher 14 to force suture clip 3 against proximal flanges 13. Sufficient force is applied so that fingers 9 spread radially outwardly as a result of the sliding contact of proximal tangs 13 with the outer surface of suture clip 3. Once suture clip 3 is advanced past proximal tangs 13, fingers 9 spring back into the first position. When in the first position, distal tangs 12 contact suture clip 3 and stop the advancement of suture clip 3.

To advance suture clip 3 past device 1, additional force is applied to pusher 14 so that pusher distal end 19 contacts and advances along proximal tangs 13 which causes fingers 9 to flex radially outwardly into the second position. Pusher distal end 19 simultaneously pushes suture clip 3, now disengaged with distal tangs 12, out of the distal end of device 1 against application 5.

Figure 5:
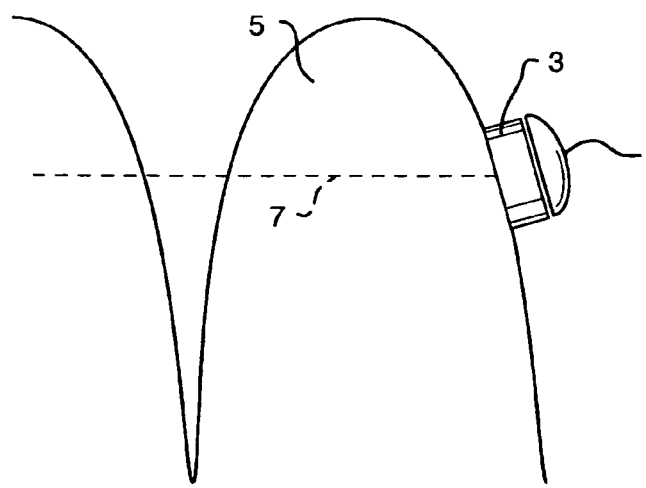
FIG. 5 is a side elevational view of a placation with a suture clip attached to a suture according to one embodiment of the invention.

Unlike other prior art designs, the design of device 1 allows for direct contact between plication 5 and device 1 so that the placement of a suture clip can be compressed against the plication with minimal or no slack in the suture as shown in FIGS. 3 and 5. This ensures the suture will properly maintain the plication in the desired bound state.

Referring to FIGS. 2A-2B, another embodiment of device 1 is shown attached to a distal end of a catheter 39. The procedure described above with respect to an endoscope also applies to a catheter-based version of device 1 except that in this embodiment, pusher 14 is preferably run through a central lumen of catheter 39.

Figure 10:
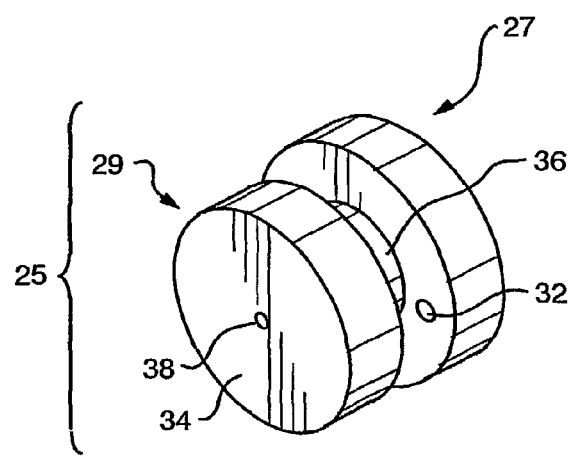
FIG. 10 is a perspective view of a suture clip assembly in a partially closed position according to one embodiment of the invention.
Figure 6:
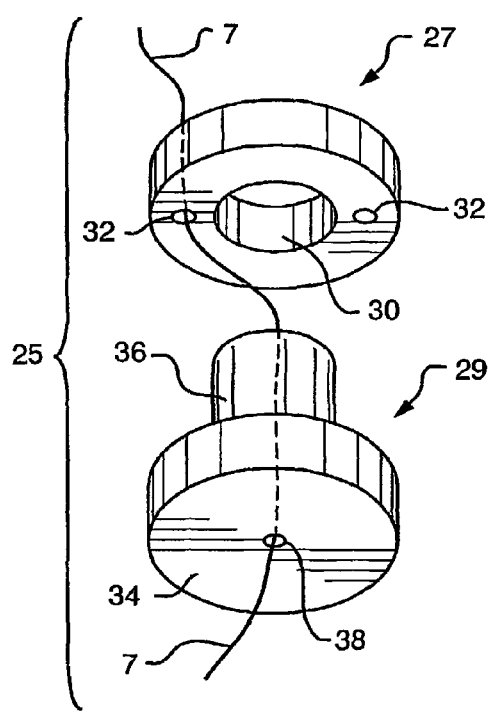
FIG. 6 is a perspective view of a suture clip assembly in an open position according to one embodiment of the invention.
Figure 7:
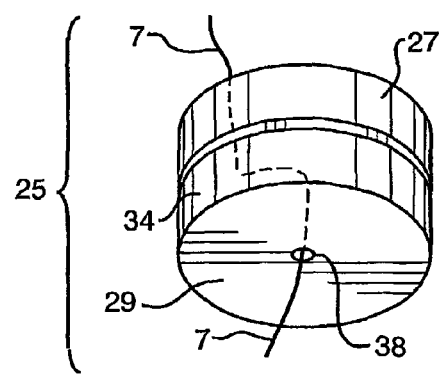
FIG. 7 is a perspective view of a suture clip assembly in a closed position according to one embodiment of the invention.
Figure 8:
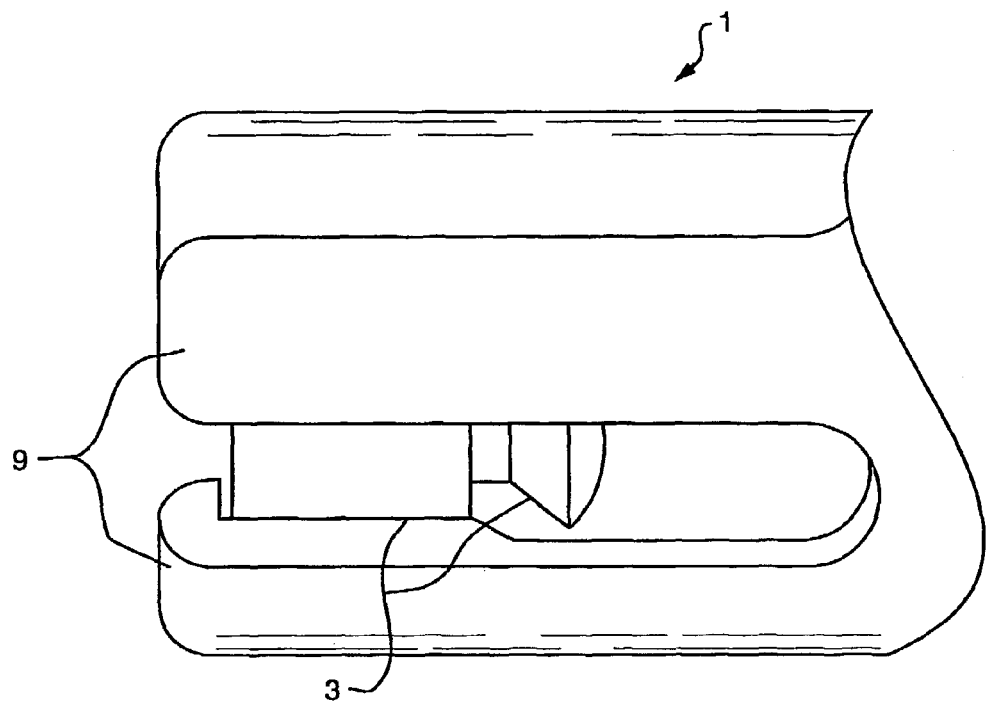
FIG. 8 is a perspective view of a suture clip assembly in an open position according to another embodiment of the invention.

Referring to FIGS. 6-16, a variety of suture clip embodiments are shown that employ a friction fit means to secure one or more sutures. As shown in FIGS. 6, 7 and 10, a suture clip assembly 25 is shown comprised of a suture disk 27 and a disk post 29. In this embodiment, suture disk 27 has portions defining a central disk aperture 30 that is preferably located in the radial center of suture disk 27. Suture apertures 32 are formed in suture disk 27 radially outwardly from disk aperture 30. Suture apertures 32 are adapted to receive sutures 7. One or more suture apertures 32 can be formed in suture disk 27.

Disk post 29 has a disk post main body 34 that is preferably circular with a diameter that matches the diameter of suture disk 27. A locking post 36 extends axially from a face of disk post 29 and is preferably an integral part of disk post 29. Locking post 36 has a cross-sectional diameter that is sized to fit tightly within disk aperture 30. A post aperture 38 runs axially through disk post 29 and locking post 36. Post aperture 38 is adapted to receive sutures 7 and is preferably located in the radial center of disk post 29.

Figure 9:
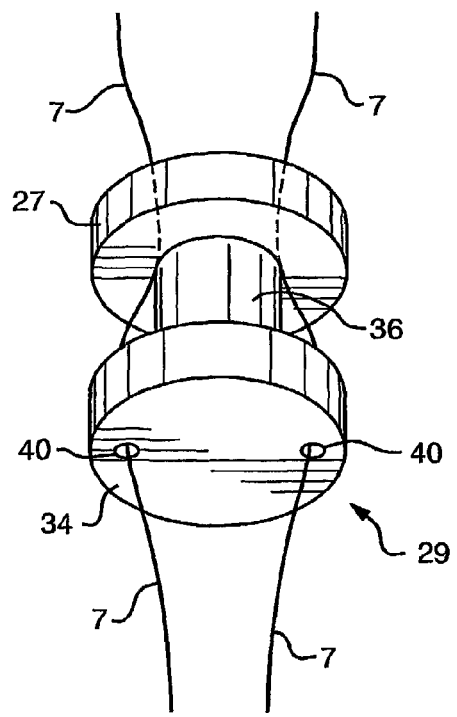
FIG. 9 is a perspective view of a suture clip assembly in a partially closed position according to a further embodiment of the invention.
Figure 11:
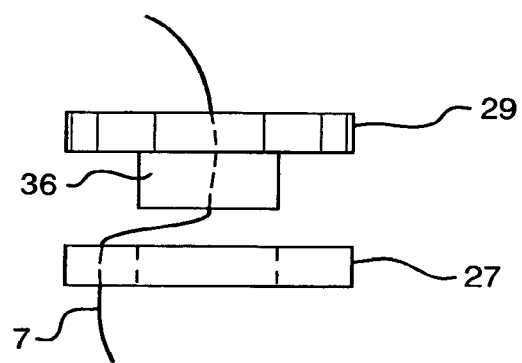
FIG. 11 is a side elevational view of a suture clip assembly in an open position according to another embodiment of the invention.
Figure 12:
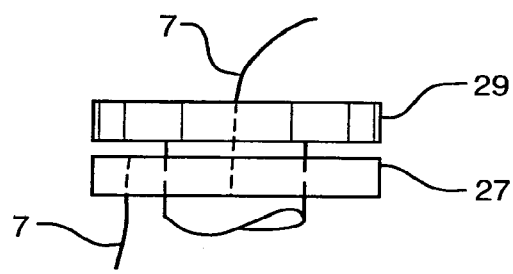
FIG. 12 is a side elevational view of a suture clip assembly in a closed position according to one embodiment of the invention.
Figure 13:
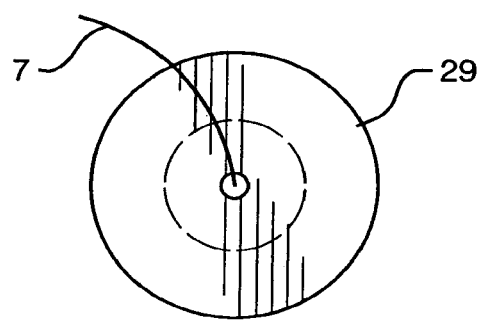
FIG. 13 is a top view of a suture clip assembly according to one embodiment of the invention.
Figure 14:
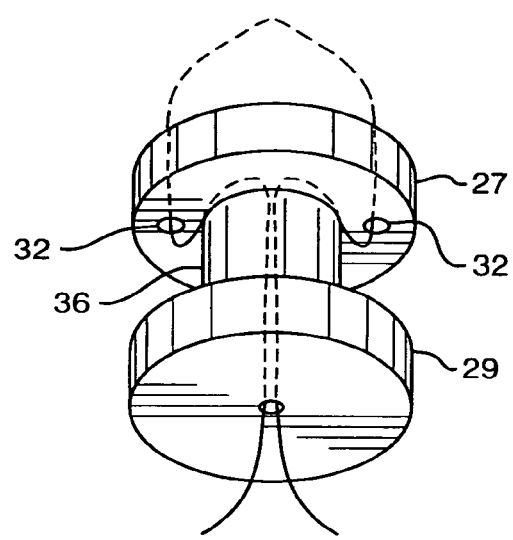
FIG. 14 is a perspective view of a suture clip assembly according to a further embodiment of the invention.
Figure 15:
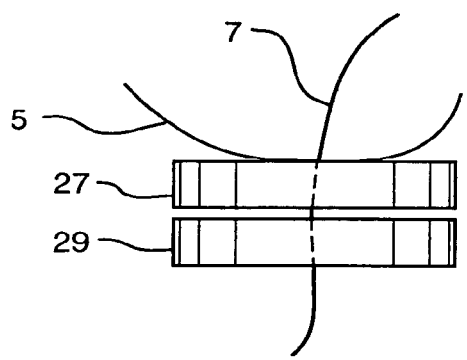
FIG. 15 is a side elevational view of a suture clip assembly in a closed position according to a further embodiment of the invention.
Figure 16:
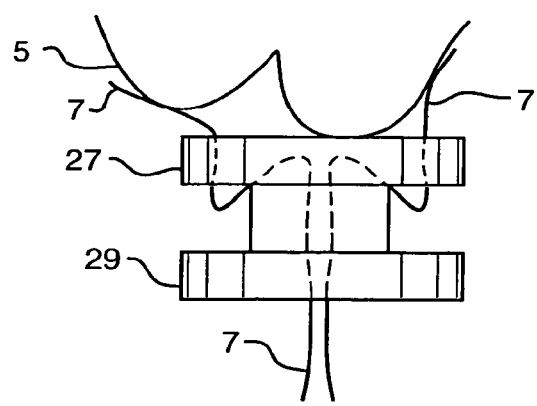
FIG. 16 is a side elevational view of a suture clip assembly in a partially closed position according to another embodiment of the invention.

In the embodiment shown in FIG. 6, locking post 36 has a smooth outer surface. As shown in FIG. 9, locking post 36 has a corrugated surface that can also be formed with threading to enhance grasping of sutures 7 when suture clip assembly 25 is manipulated into a closed position. Locking post 36 and disk aperture 30 can be formed with matching tapers that allow for one-way insertion of locking post 36 into disk aperture 30 to further enhance grasping of sutures 7.

To use this embodiment of suture clip assembly 25, a suture 7 (extending out of the mouth of the patient in an endoscopic procedure), is thread through post aperture 38 from a distal end of disk post 34 to a proximal face of disk post main body 34. Suture 7 is then fed through suture aperture 32 from a distal face of suture disk 27 to a proximal face of suture disk 27. Both suture disk 27 and disk post 29 are slid along suture 7 until in place in holding chamber 4 of device 1.

Before securing suture disk 27 to disk post 29, any slack in suture 7 is taken up by pulling suture 7 in a proximal direction. To engage disk post 29 to suture disk 27, Force is applied to pusher 14 which forces locking post 36 into disk central aperture 30. Suture 7 becomes entrapped or captured between the mating surface of locking post 36 and disk central aperture 30 as well as between the proximal face of suture disk 27 and the distal face of disk post 29. The tortuous path followed by suture 7 adds to the friction achieved between suture 7 and suture clip assembly 25. FIGS. 11-16 show the path followed by one suture 7 and dual sutures 7 in this embodiment.

Once suture clip assembly 25 has been assembled, suture 7 is captured with suture clip assembly 25 interfacing with plication 5. Suture 7 passes between proximal tang 13 and pusher distal end 19 such that when distal end 19 is forced against proximal tang 13, suture 7 captured. As shown in FIG. 3, an edge 23 formed in device 1 acts as a knife to sever suture 7 when suture 7 is tensioned by pulling suture 7 proximally while pusher 14 is forced distally through device 1.

In an alternative embodiment shown in FIG. 9, suture disk 27 is not formed with suture apertures 32. Instead, disk post main body 34 is provided with disk post suture apertures 40 that are formed radially outwardly from locking post 36. Sutures 7 are fed through central aperture 30 and through disk post suture apertures 40. Joining of suture disk 27 and disk post 29 results in the same capture of sutures 7 as previously described.

A further embodiment is shown in FIG. 17. In this embodiment, top plate 40 conforms to the shape of a "T" with a flange 62 situated at a bottom portion of top plate 40. Bottom plate 42, separate from top plate 40, is sized and shaped to conform to the shape of flange 62 and has a radially inwardly extending lip 64 dimensioned to conform to the shape of a main trunk 66 of top plate 40. When combined and locked together, the interfacing surfaces of top plate 40 and bottom plate 42 capture suture 7 as shown.

FIGS. 18-34 show suture clip embodiments with alignable finger systems that capture suture 7 when placed in an unaligned condition. FIGS. 18 and 19 show a suture clip 3 that is generally rectangular in shape and is comprised of rails 110 that form the perimeter of the clip. A middle rail 112 attached to two rails 110 has a central humped portion 114 that projects upwardly from the plane occupied by suture clip 3. Suture apertures 116 one each in middle rail 112 through humped portion 114 and in the two rails 110 oriented in parallel to middle rail 112 are provided through the sides of rails 110 and middle rail 112. Suture apertures 116 are preferably formed along a plane perpendicular to middle rail 112.

The offset nature of suture apertures 116 provide sufficient friction to capture sutures 7. To move suture clip 3 along sutures 7, pressure is exerted on the bottoms of parallel rails 110 and on the top of hump portion 114 until suture apertures 116 are in alignment. Middle rail 112 must be made of a material that has enough elasticity to flex into coplanar alignment with rails 110 as well as have enough material memory to rebound back into an unaligned state to provide the necessary friction to capture sutures 7.

Figure 22:
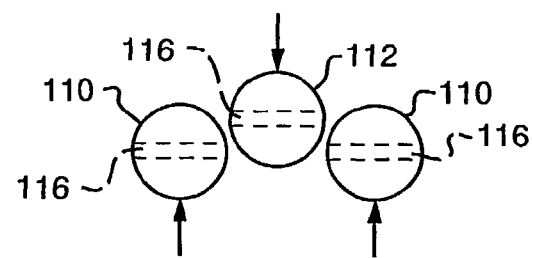
FIG. 22 is an end elevational view of a suture clip assembly in a closed initial position according to one embodiment of the invention.
Figure 23:
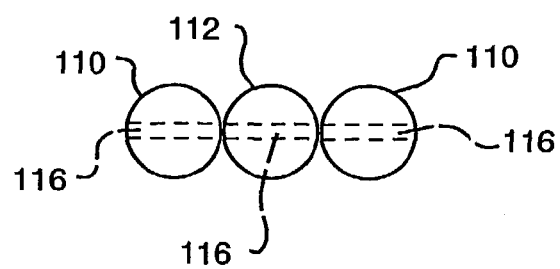
FIG. 23 is a side elevational view of a suture clip assembly in an open position according to one embodiment of the invention.

FIG. 20 shows an embodiment with suture apertures 116 in rails 110 extending from a top surface to a bottom surface of rails 110. This configuration provides additional friction by threading sutures 7 through suture apertures 116 from the bottom surfaces of rails 110. FIG. 21 shows an embodiment which utilizes rails 110 having circular cross-sectional shapes. FIG. 22 shows how forces have to be applied to the individual rails as illustrated by the arrows provided therein. FIG. 23 shows rails 110 and middle rail 112 in alignment such that friction on sutures 7 can be relieved for advancement of suture clip 3 over sutures 7.

Figure 24:
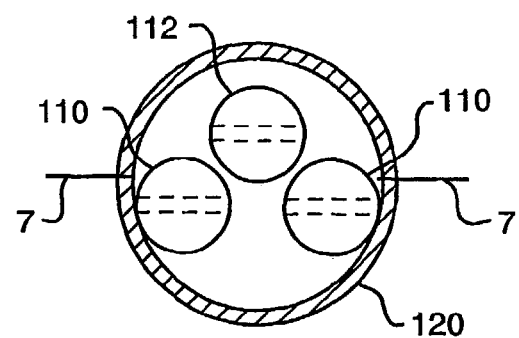
FIG. 24 is an end view of a suture clip assembly and outer tube according to one embodiment of the invention.

FIG. 24 shows a suture clip 3 with unaligned rails 110 and middle rail 112 situated in an outer tube 120. Use of an outer tube that has high internal hoop stress and minimal tendencies to set at body temperature is preferred. Braided construction or spring reinforced versions are other alternatives that can be used. Capture of sutures 7 in this embodiment is only possible when outer tube 120 is preferably circular in cross-sectional shape and deformed by a compressive force applied perpendicular to the axis of sutures 7. Deformation can be achieved by use of a pinching tool passed over sutures 7 and outer tube 120 at the point where sutures 7 is threaded through suture clip 3.

Figure 25:
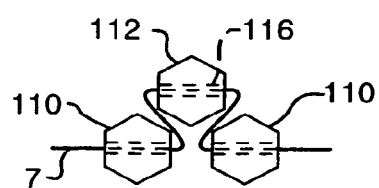
FIG. 25 is an end elevational view of a suture clip assembly according to one embodiment of the invention.
Figure 26:
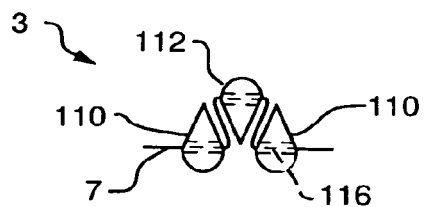
FIG. 26 is an end elevational view of a suture clip assembly according to another embodiment of the invention.
Figure 27:
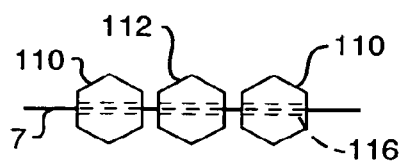
FIG. 27 is an end elevational view of a suture clip assembly according to a further embodiment of the invention.
Figure 28:
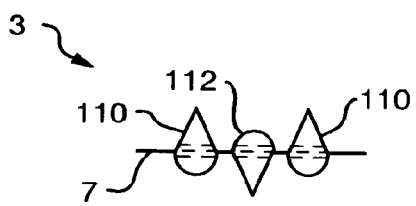
FIG. 28 is a side elevational view of a suture clip assembly according to a yet further embodiment of the invention.

FIGS. 25 and 26 show a suture clip 3 with rails 110 and middle rail 112 with hexagonal cross-sectional shapes to increase the friction or lockup in the relaxed position, i.e., unaligned position. FIG. 27 shows the same suture clip 3 in an aligned position. FIG. 26 shows a suture clip 3 with rails 110 and middle rail 112 with radiused cone-shape cross-sections with the radiused portions alternately inverted to again increase lockup in the relaxed position. FIG. 28 shows the same embodiment with the cone-shaped rails in an aligned position.

FIGS. 29 through 32 show a number of embodiments with alternative geometric cross-sectional shapes for the guide rails and the outer tube 120. With these configurations, a snare device could be used by advancing the snare along suture 7 to the point of contact with suture clip 3 where the snare could be used to apply pressure to release the lock on suture 7. Such a device is shown in FIGS. 35-38 referenced below.

Figure 33:
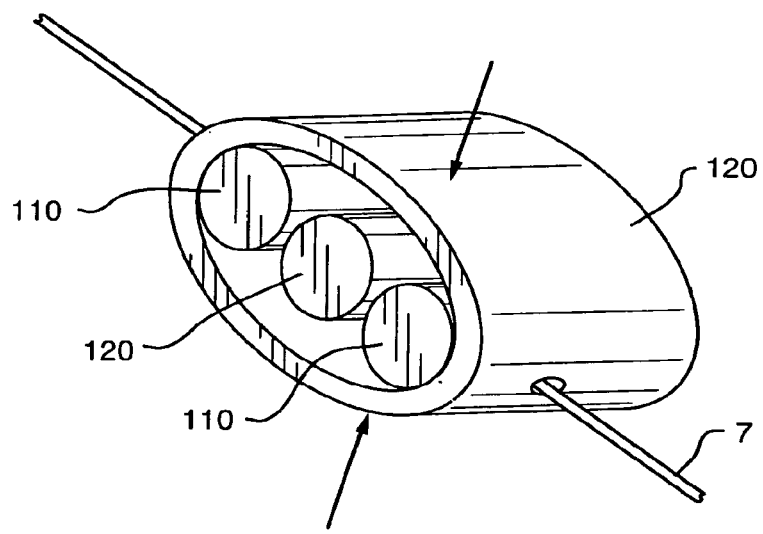
FIG. 33 is a perspective view of a suture clip assembly and outer tube according to one embodiment of the invention.
Figure 34:
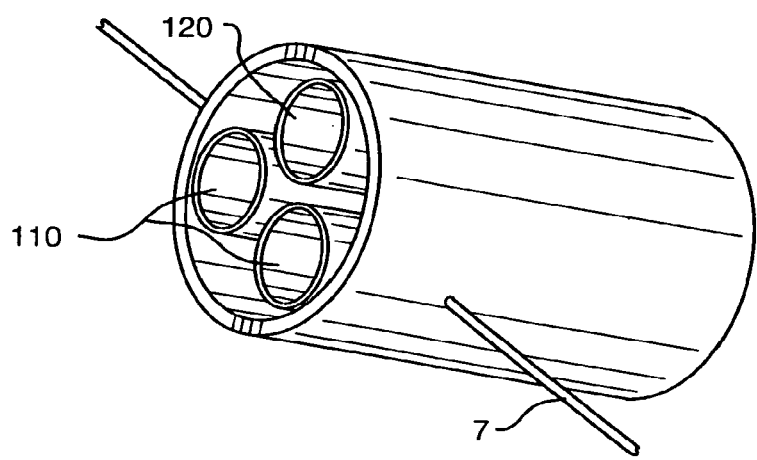
FIG. 34 is a perspective view of a suture clip assembly and outer tube according to one embodiment of the invention.
Figure 29:
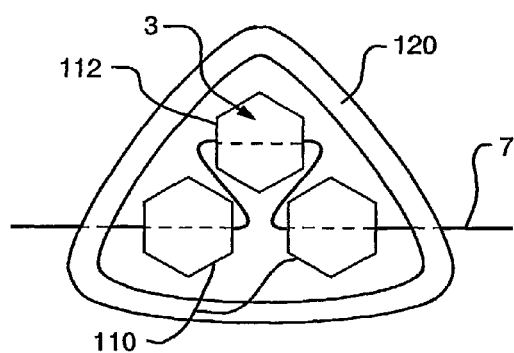
FIG. 29 is an end elevational view of a suture clip assembly and outer tube according to one embodiment of the invention.
Figure 30:
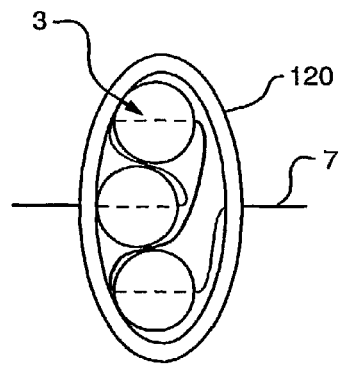
FIG. 30 is a side elevational view of suture clip assembly and outer tube according to another embodiment of the invention.
Figure 31:
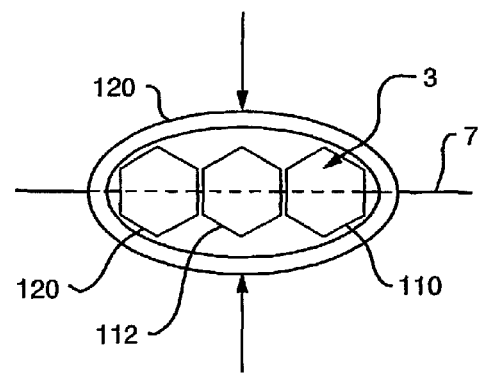
FIG. 31 is a side elevational view of a suture clip assembly and outer tube according to a further embodiment of the invention.
Figure 32:
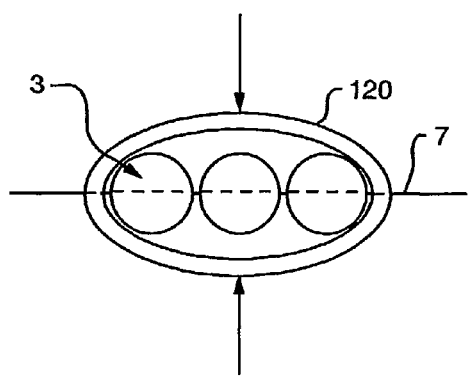
FIG. 32 is a side elevational view of a suture clip assembly and outer tube according to a yet further embodiment of the invention.

FIG. 33 shows the application of a compressive force (designated by the arrows) that causes rails to align which, in turn, releases the friction on suture 7. FIG. 34 shows the same embodiment as FIG. 33 with the compressive force removed which allows the rails to misalign and capture suture 7.

Figure 35:
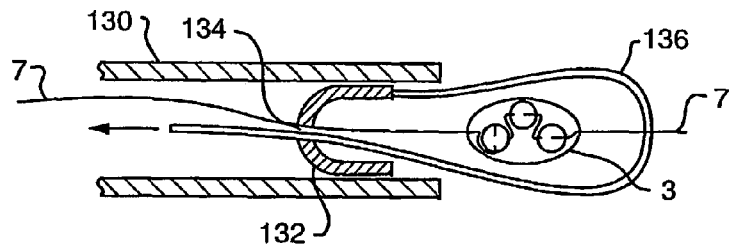
FIG. 35 is a side elevational view of a suture clip delivery tube and suture clip according to one embodiment of the invention.
Figure 36:
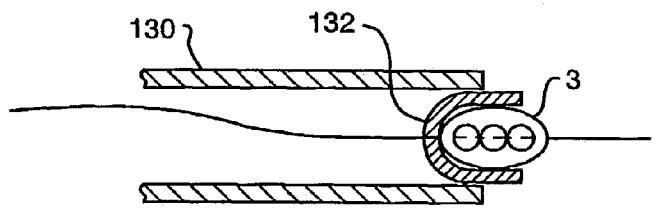
FIG. 36 is a sectional view of a delivery tube with mounted suture clip before delivery of the suture clip to the desired site according to one embodiment of the invention.
Figure 37:
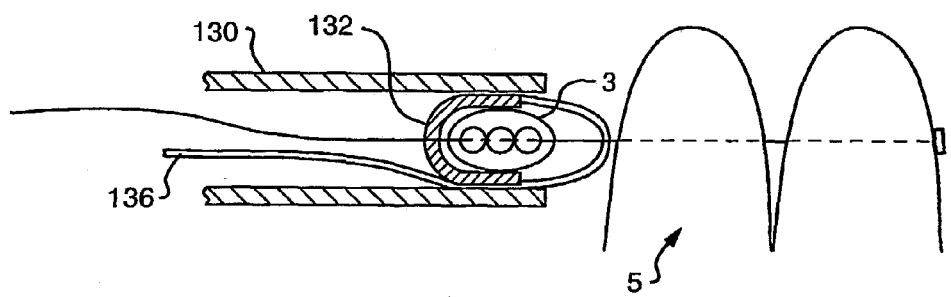
FIG. 37 is a sectional view of a delivery tube with mounted suture clip during delivery of the suture clip according to one embodiment of the invention.
Figure 38:
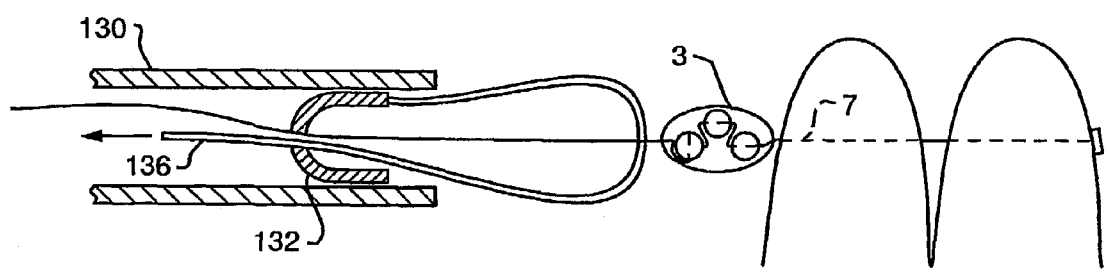
FIG. 38 is a sectional view of a delivery tube being retracted from a suture clip delivery site according to one embodiment of the invention.

FIG. 35 shows a suture delivery device for suture locks having alignable fingers. An elongate delivery tube 130 is provided with an inner partial tube 132 that is fixed to delivery tube 130 proximal to a distal end of delivery tube 130. Inner partial tube 132 has an open distal end and a proximal end that preferably conforms to the shape of an ellipse. The elliptical shape is designed to cradle a suture lock 3 that incorporates the alignable finger technology described above. An inner tube aperture 134 is formed in the proximal end of, or if elliptically shaped in a proximal apex of, inner partial tube 132.

A snare 136 is provided of which a distal end is attached to an inner wall of delivery tube 130 at the distal end of delivery tube 130. A proximal end of snare 136 is fed through inner tube aperture 134 and extends back to a proximal end of delivery tube 130 where snare 136 can be manipulated by the user.

To operate delivery tube 130, snare 136 is maintained in a loose state so that a suture clip 3 (to which suture 7 has been threaded through) can be mounted into delivery tube 130 and placed against partial inner tube 132. Tension is applied to snare 136 to secure suture clip 3 to delivery tube 130. The force applied to suture clip 3 by tensioning snare 136 causes the rails of the suture clip to align and allow for the suture clip to move along the length of suture 7.

To place suture clip 3 in position in close proximity to and preferably against a sutured tissue fold, delivery tube 130 is advanced to the tissue fold by sliding delivery tube 130 and suture clip 3 over suture 7. Once the desired position is reached, tension on snare 136 is released which allows the rails of suture clip 3 to return to an unaligned orientation which causes capture of suture 7. Preferably, the force generated by the repositioning of the rails causes suture clip 3 to move at least partially out of delivery tube 130. Once suture clip is in the desired location, delivery tube 130 is retracted and suture 7 severed at a point proximal to suture clip 3. In one embodiment, delivery tube 130 is provided with an edge that severs suture 7 when delivery tube 130 is retracted.

Figure 39:
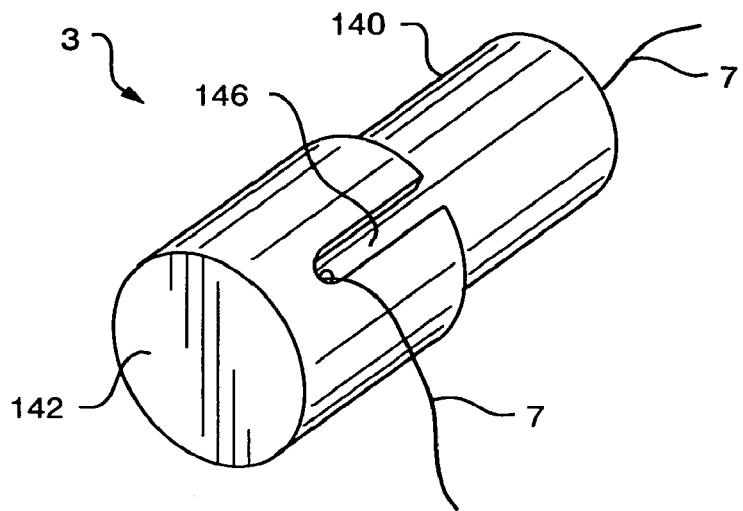
FIG. 39 is a perspective view of a suture clip comprising a cylinder and cylinder cap according to one embodiment of the invention.
Figure 40:
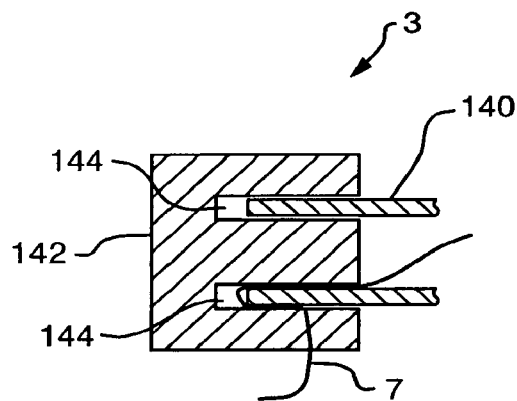
FIG. 40 is a sectional view of a partially engaged cylinder/cylinder cap suture clip assembly according to one embodiment of the invention.
Figure 41:
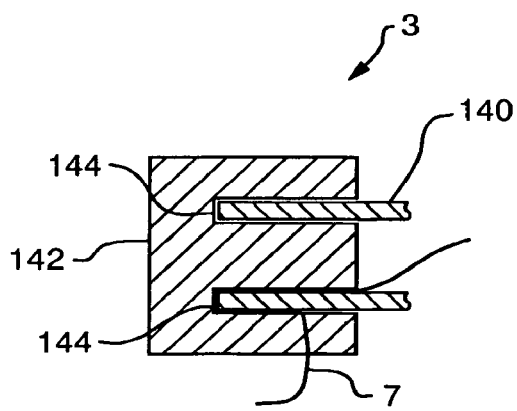
FIG. 41 is a sectional view of an engaged cylinder/cylinder cap suture clip assembly according to one embodiment of the invention.
Figure 102:
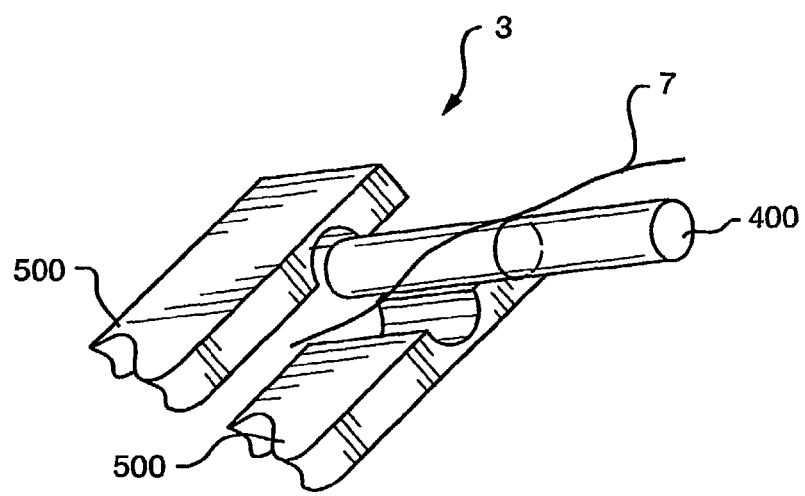
FIG. 102 is a perspective view of an unassembled rod/clamping jaw suture clip assembly according to a still further embodiment of the invention.

FIGS. 39-102 show other general embodiments of the suture clip that incorporate cylinders in a variety of configurations to achieve suture capture. FIGS. 39-43 show a suture clip embodiment that combines a cylinder with a locking cap. As shown in FIGS. 39-41, a suture lock 3 is shown that comprises an elongate hollow cylinder 140 and a cylinder cap 142. Cap 142 and an annular slot 144 that is adapted to receive an end of cylinder 140. A wall slot 146 is provided in a side wall of cap 142 and extends from the exterior surface of the side wall to annular slot 144.

Figure 42:
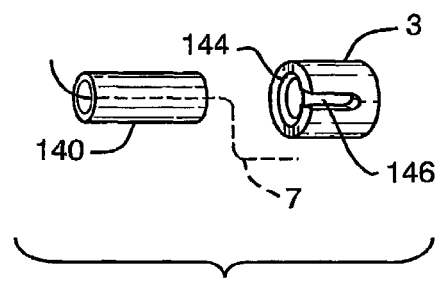
FIG. 42 is a perspective view of an unassembled cylinder/cylinder cap suture clip assembly according to one embodiment of the invention.
Figure 43:
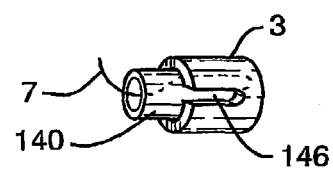
FIG. 43 is a perspective view of an assembled cylinder cap/cylinder suture clip assembly according to one embodiment of the invention.

With this suture clip embodiment, cylinder 140 is advanced over suture 7. Cap 142 is then slipped over an end of cylinder 140 with suture 7 situated in wall slot 146 as shown in FIG. 40. As shown in FIG. 41, suture 7 is captured by the interfacing surfaces of cylinder 140 and cap 142. FIGS. 42 and 43 show the tortuous path of suture 7 within suture clip 3 that aids in the capture of suture 7.

Figure 44:
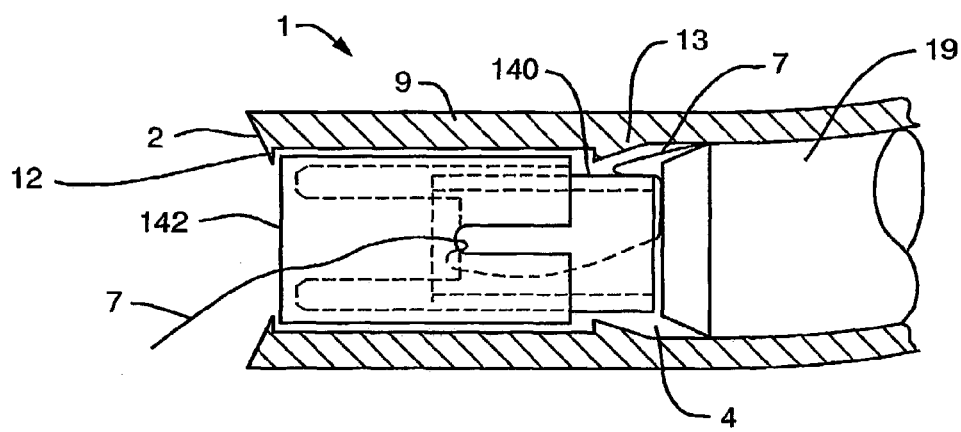
FIG. 44 is a side sectional view of a cylinder cap/cylinder suture clip assembly preloaded in a delivery device according to one embodiment of the invention.
Figure 45:
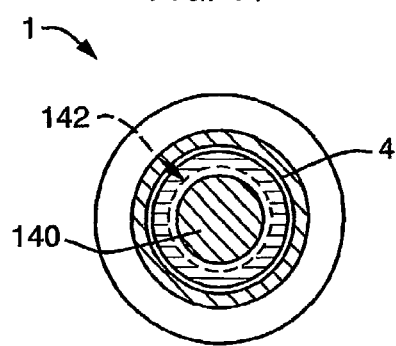
FIG. 45. is a front sectional view of a cylinder cap/cylinder suture clip assembly preloaded in a delivery device according to one embodiment of the invention.

FIGS. 44 and 45 show a suture clip 3 in a cylinder/cap embodiment premounted in device 1. To effectuate closure of cylinder 140 to cap 142, a closed end of cap 142 interfaces with distal tang 12. Cylinder 140 is forced into cap 142 by pusher 14 (not shown) via pusher head 19.

Figure 46:
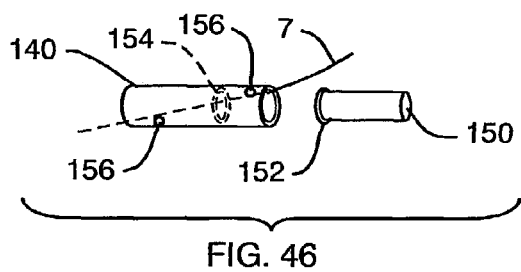
FIG. 46 is a perspective view of an unassembled cylinder/locking rod suture clip assembly according to another embodiment of the invention.

FIGS. 46-49 show a suture clip 3 in a cylinder/locking rod embodiment. FIG. 46 shows a cylinder 140 being combined with a rod 150. Rod 150 can be sized to engage the inner wall of cylinder 140 to create a friction fit or can be provided with an optional rod locking flange 152 that is sized to engage either the inner wall of cylinder 140 or an annular cylinder locking channel 154. Optionally, cylinder apertures 156 are provided, preferably at two locations, along the length of cylinder 140. Suture 7 can be advanced through cylinder 140 through the ends of the cylinder, through the cylinder apertures 156 or through a combination of the cylinder ends and apertures.

Figure 47:
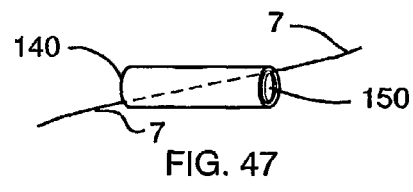
FIG. 47 is a perspective view of an assembled cylinder/locking rod suture clip assembly according to another embodiment of the invention.

With suture 7 threaded in cylinder 140, rod 150 is inserted into cylinder 140 such that the interfacing surfaces of rod 140 and cylinder 150 capture suture 7 as shown in FIG. 47. The capture point can include the interfacing surfaces of locking flange 152 and locking channel 154.

Figure 48:
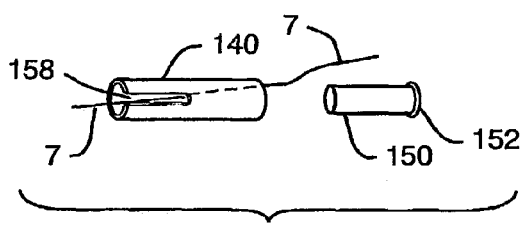
FIG. 48 is a perspective view of an unassembled slotted cylinder/locking rod suture clip assembly according to a further embodiment of the invention.
Figure 49:
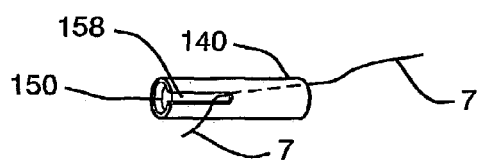
FIG. 49 is a perspective view of an assembled slotted cylinder/locking rod suture clip assembly according to a further embodiment of the invention.

FIGS. 48 and 49 show an alternative embodiment in which a cylinder slot 158 is formed in the sidewall of cylinder 140. Preferably, slot 158 extends from, and opens onto, an end of cylinder 140. In this embodiment, suture 7 is threaded through cylinder slot 158 and out the opposite end of cylinder 140. Again, the interfacing surfaces of cylinder 140 and rod 150 capture suture 7 as shown in FIG. 49.

Figure 50:
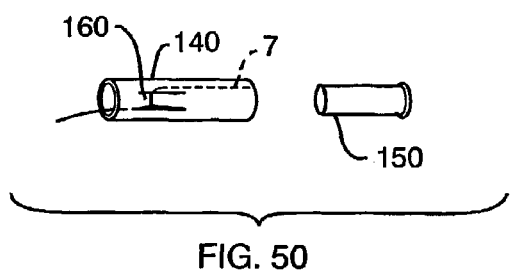
FIG. 50 is a perspective view of an unassembled eyelet-bearing cylinder/locking rod suture clip assembly according to a still further embodiment of the invention.
Figure 51:
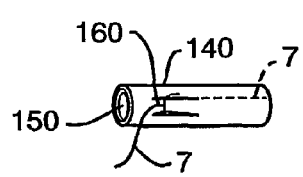
FIG. 51 is a perspective view of an assembled eyelet-bearing cylinder/locking rod suture clip assembly according to a still further embodiment of the invention.
Figure 52:
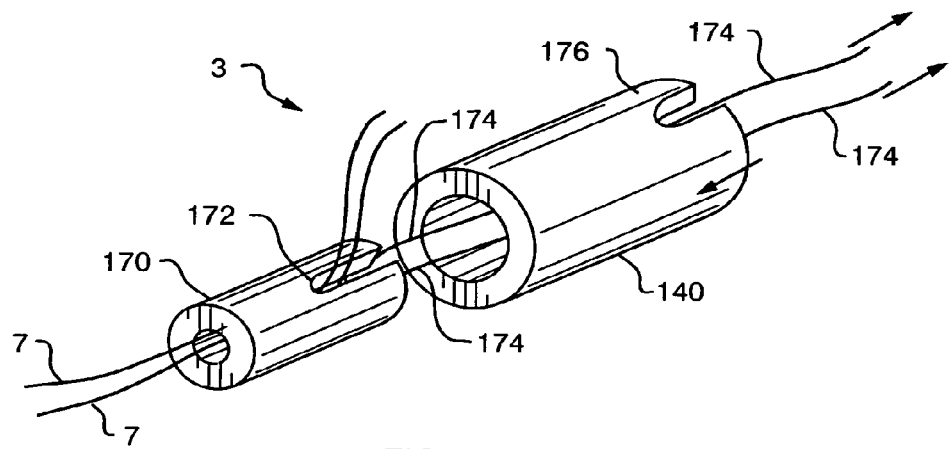
FIG. 52 is a perspective view of an unassembled dual cylinder suture clip assembly according to a yet further embodiment of the invention.

FIGS. 50 and 51 show a further alternative embodiment in which cylinder 140 is provided with an eyelet 160 that is essentially an elongated section of the sidewall of cylinder 140 that has been separated from the sidewall along the axial length of cylinder 140 and folded either inwardly to form two triangular slots. Suture 7 is threaded through a first end of cylinder 140 and over the exterior surface of eyelet 160 and out the second end of cylinder 140. Rod 150 is inserted into cylinder 140 which forces eyelet 160 to be reamed outwardly such that suture 7 is captured by the interfacing surfaces of the sidewall of cylinder 140 and the edges of eyelet 160. The friction created by the addition of eyelet 160 adds to the friction provided by the interfacing surfaces of cylinder 140 and rod 150.

Figure 53:
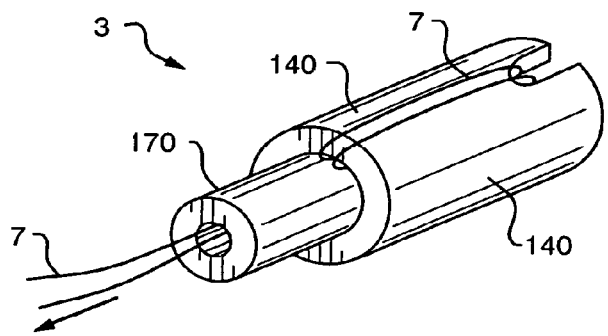
FIG. 53 is a perspective view of an assembled dual cylinder suture clip assembly according to a yet further embodiment of the invention.

FIGS. 52-57 show a suture clip 3 employing a dual cylinder system. FIG. 53 shows a cylinder 140 and an inner cylinder 170 that has an outer diameter that is preferably sized to provide a friction fit with the inner wall of cylinder 140. Inner cylinder 170 has an inner cylinder slot 172 extending from, and opening onto a proximal end of inner cylinder 170. Cylinder 140 can optionally have a groove 176 formed on a proximal end of cylinder 140 that is used to engage suture 7 as described below.

Figure 54:
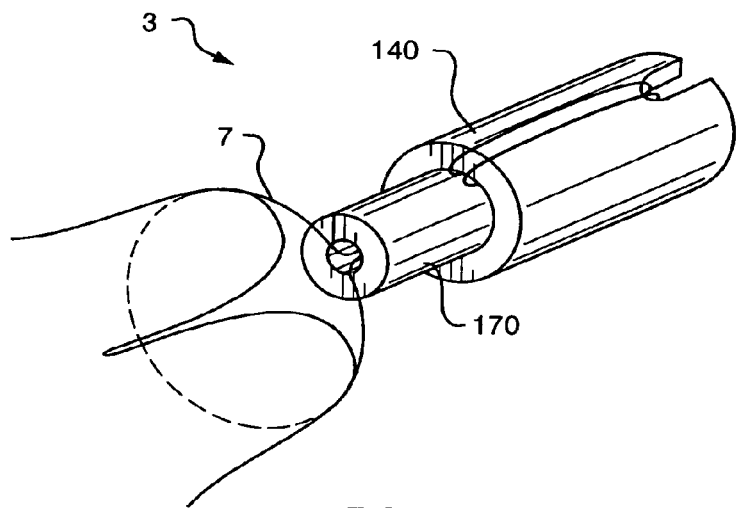
FIG. 54 is a perspective view of an assembled dual cylinder suture clip assembly cinched to a plication according to a yet further embodiment of the invention.

To operate this embodiment, inner cylinder 170 is advanced over suture 7 (or suture 7 is threaded through inner cylinder 170) so that suture 7 exits via inner cylinder slot 172 and over the side wall of cylinder 140. Pull strings 174 are attached to the proximal end of inner cylinder 170 and are threaded through cylinder 140. To join the cylinders, the user pulls on pull strings 174 toward the proximal end of the endoscope or catheter used to deliver suture clip 3. Cylinder 140 is maintained in a static position with the proximal portion of chamber 4 of device 1 within which suture clip 3 in this embodiment can be premounted. The interfacing surfaces of cylinder 140 and inner cylinder 170 capture suture 7 along the portion of the sidewall of inner cylinder 170 that is distal to the distal end of inner cylinder slot 172 as well as the tortuous path followed by suture 7. Suture 7 can be additionally captured by groove 176 such that any pulling of suture 7 will tighten the contact between cylinder 140 and inner cylinder 170. FIG. 53 shows suture clip 3 in a locked position and FIG. 54 shows suture clip 3 set on suture 7 against tissue 5.

Figure 55:
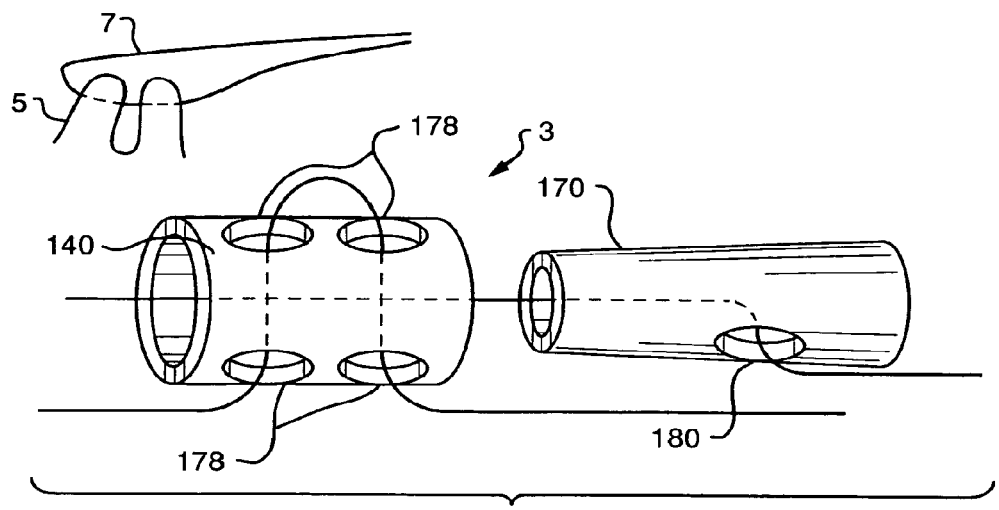
FIG. 55 is a perspective view of an unassembled dual cylinder suture clip assembly having sidewall apertures according to yet another embodiment of the invention.
Figure 56:
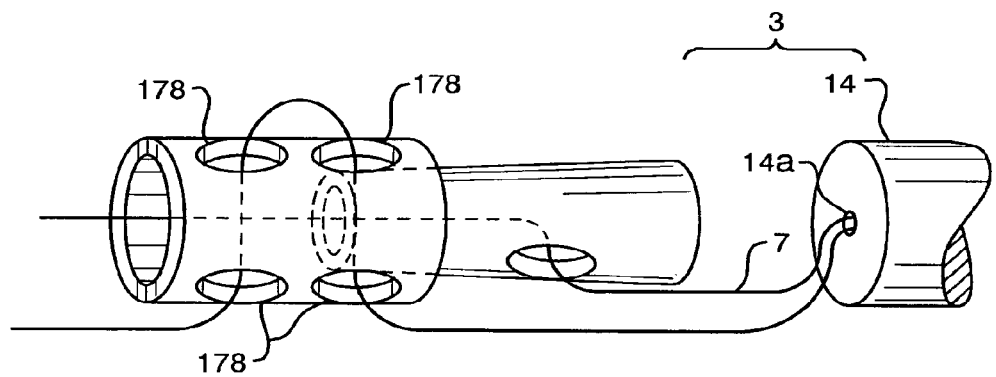
FIG. 56 is a perspective view of a partially assembled dual cylinder suture clip assembly having sidewall apertures according to yet another embodiment of the invention.
Figure 57:
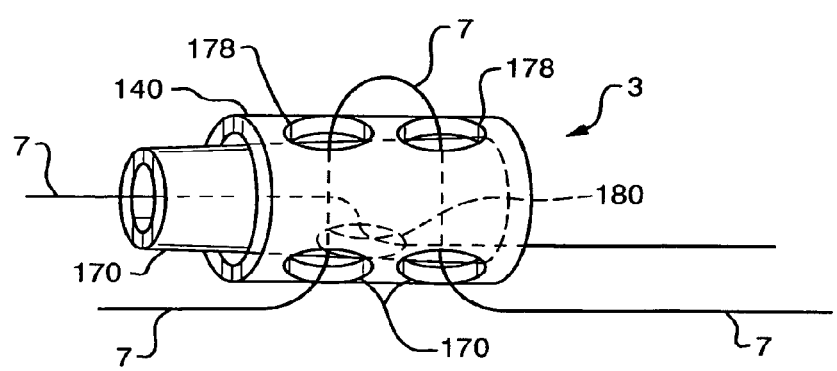
FIG. 57 is a perspective view of an assembled dual cylinder suture clip assembly having sidewall apertures according to yet another embodiment of the invention.

FIGS. 55-57 show a modification of the dual cylinder embodiment. In this embodiment, cylinder apertures 178 are formed in the sidewall of cylinder 140. Preferably, two coplanar pairs of diametrically opposed cylinder apertures 178 are provided. Inner cylinder 170 is tapered with the diameter increasing from the proximal end to the distal end. An inner cylinder aperture 180 is formed in the side wall of inner cylinder 170. Suture 7 can be threaded through any combination of a distal end of cylinder 140, cylinder apertures 178 and a proximal end of cylinder 140 as shown in FIG. 55. Suture 7 is then treaded through the distal end of inner cylinder 170 and out through inner cylinder aperture 180. Suture 7 is then threaded through a pusher aperture 14a formed in pusher 14. Pusher aperture 14a preferably extends to the proximal end of pusher 14.

To join the cylinders together, in one embodiment, cylinder 140 is set against tangs 12 of device 1. Inner cylinder 170 is situated in the proximal end of chamber 4 and is forced into cylinder 140 with pusher 14. The interfacing surfaces of cylinder 140 and inner cylinder 170 capture suture 7 and are aided by the tortuous path followed by suture 7 within this embodiment of suture clip 3. The interfacing surfaces of pusher 14 and suture clip 3 can be used to sever suture 7 distally of suture clip 3

Figure 58:
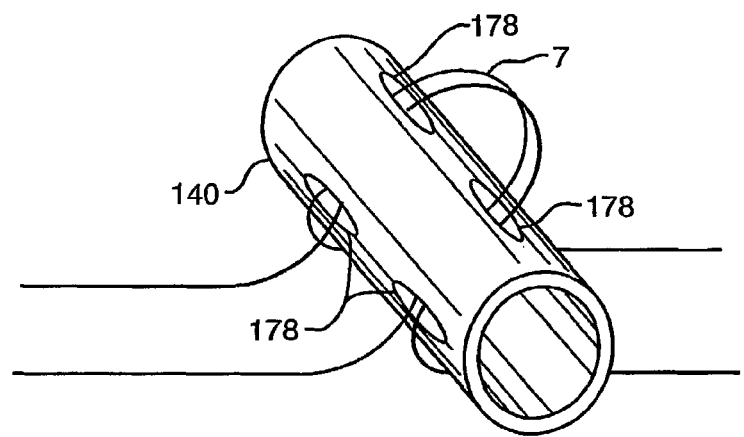
FIG. 58 is a front perspective view of a single cylinder suture clip assembly with sidewall apertures according to still another embodiment of the invention.
Figure 59:
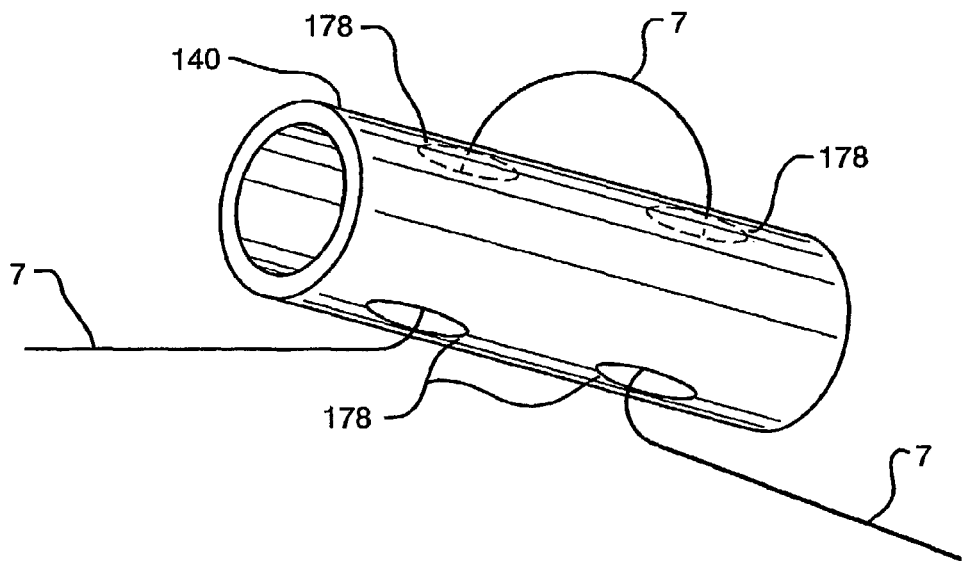
FIG. 59 is a side perspective view of a single cylinder suture clip assembly with sidewall apertures according to still another embodiment of the invention.

FIGS. 58 and 59 show a simpler version of suture clip 3 that includes cylinder 140 with cylinder apertures 178. Suture 7 is advanced through a first cylinder aperture then to a second cylinder aperture that is diametrically opposed to the first cylinder aperture then to a third cylinder aperture that is substantially coplanar with the second cylinder aperture and finally through a fourth aperture that is diametrically opposed to the third aperture. Tension is then applied to suture 7 that creates friction between suture 7 and cylinder 140.

An alternative embodiment involving cylinder 140 and a second cylinder 182 that is aligned perpendicular to the longitudinal axis of cylinder 140. Suture 7 is threaded through cylinder 140, through a distal end of cylinder 182 and through a second cylinder aperture 184 formed in a sidewall of second cylinder 182. Tension placed on suture 7 causes friction between the interfacing surfaces of suture 7, cylinder 140 and second cylinder 182. Preferably, the distal end of second cylinder 182 contacts the sidewall of cylinder 140.

Figure 60:
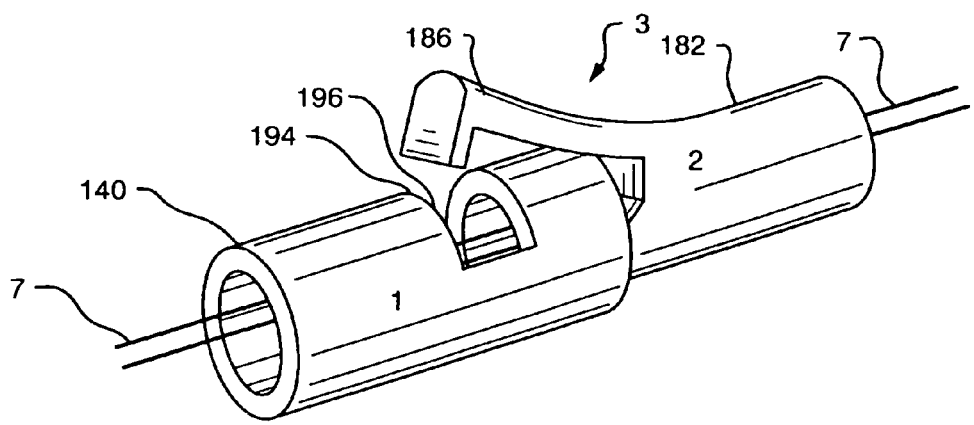
FIG. 60 is a perspective view of a partially assembled dual cylinder suture clip assembly having a locking jaw according to a further embodiment of the invention.
Figure 61:
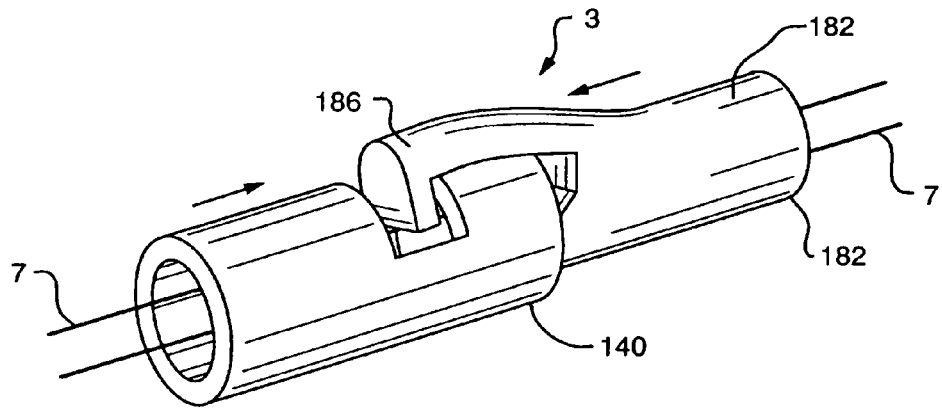
FIG. 61 is a perspective view of an assembled dual cylinder suture clip assembly having a locking jaw according to a further embodiment of the invention.
Figure 62:
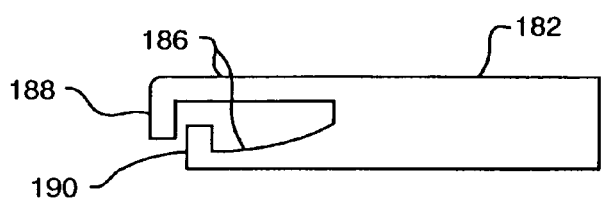
FIG. 62 is a side elevational view of a cylinder suture clip assembly component having a locking jaw according to a further embodiment of the invention.
Figure 63:
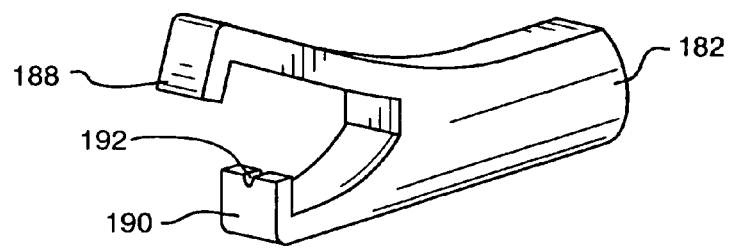
FIG. 63 is a perspective view of a cylinder suture clip assembly component having a locking jaw according to a further embodiment of the invention.

FIGS. 60-62 show an alternative embodiment of the dual cylinder embodiment in which second cylinder 182 has a locking jaw 186. Jaws 186 have a top tang 188 and a bottom tang 190 that are offset with top tang 186 offset distally relative to bottom tang 190. An optional groove 192 is formed on an uppermost tip of bottom tang 190 that is adapted to receive suture 7. Second cylinder 182 is preferably made of a material that allows for jaw 186 to be flexed from a closed position (as shown in FIG. 62) to an open position (as shown in FIG. 63) and back to a closed or semi-closed position.

A slot 194 is formed in the sidewall of cylinder 140 that is sized and adapted to receive top tang 188 in locking engagement. Suture 7 is threaded through cylinder 140, through groove 192 and through second cylinder 182 proximally to and through any device used to place suture clip 3.

To engage cylinder 140 to second cylinder 182, cylinder 140 is placed against tangs 12 of device 1. Second cylinder 182 is positioned in the distal region of chamber 4. Second cylinder 182 is pushed toward cylinder 140 until top tang 188 contacts cylinder 140 and flexes upwardly and over the exterior of cylinder 140. Second cylinder 182 is advanced until top tang 188 engages a distal shoulder 196 of aperture 194. Suture 7 is captured by the interfacing surfaces of top tang 188 and bottom tang 190 as shown in FIG. 62.

Figure 64:
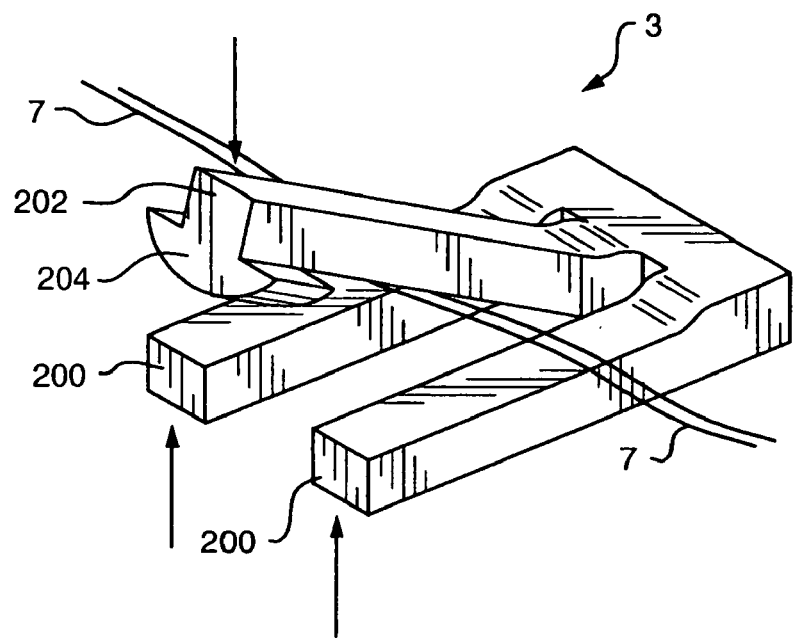
FIG. 64 is a perspective view of an unlocked three tab suture clip according to a still further embodiment of the invention.
Figure 65:
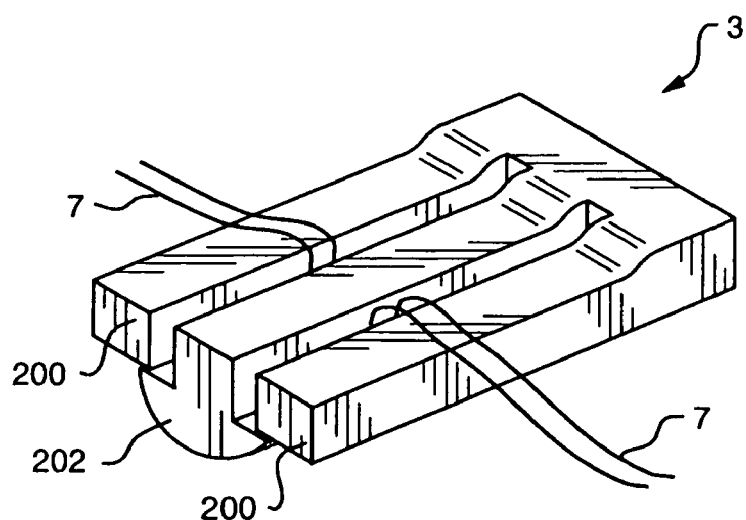
FIG. 65 is a perspective view of a locked three tab suture clip according to a still further embodiment of the invention.

FIGS. 64 and 65 show a three tab embodiment of suture clip 3. In this embodiment, suture clip 3 has two lateral tabs 200 and a central tab 202. Central tab 202 has a tab flange 204 that preferably extends perpendicular to the longitudinal axis of central tab 202 and is an integral lateral extension of a bottom face of central tab 202. Tab flange 204 extends from both lateral sides of central tab 202 beyond the adjacent sides of lateral tabs 200. Suture clip 3 is preferably made of a material that allows for central tab 202 to flex upwardly past the plane occupied by lateral tabs 200 and downwardly past the same plane.

To use this embodiment of suture clip 3, thread 7 is advanced over lateral tabs 200 and under central tab 202 that is flexed upwardly as shown in FIG. 64. Central tab 202 is then flexed downwardly beyond the plane occupied by lateral tabs 200 so that tab flange 204 contacts the bottom surfaces of lateral flanges 200. Suture 7 becomes captured by the friction created by the tortuous path followed through the tabs of suture clip 3.

Figure 66:
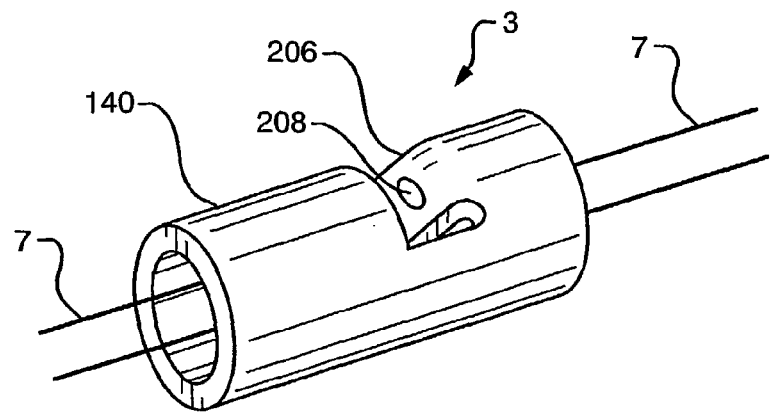
FIG. 66 is a perspective view of a cylinder suture clip having a rotatable flap according to a yet further embodiment of the invention.
Figure 67:
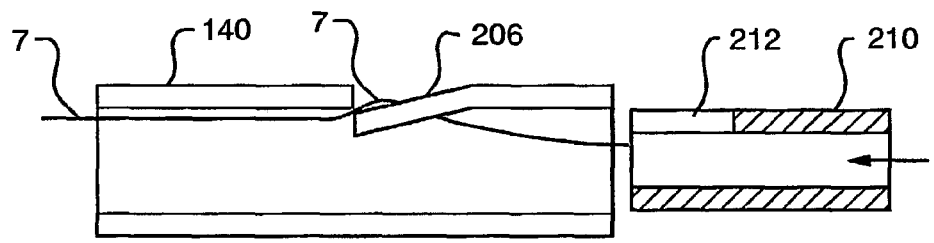
FIG. 67 is a partial sectional, perspective view of an unassembled cylinder/hollow rod suture clip assembly with the cylinder having a rotatable flap according to a yet further embodiment of the invention.
Figure 68:
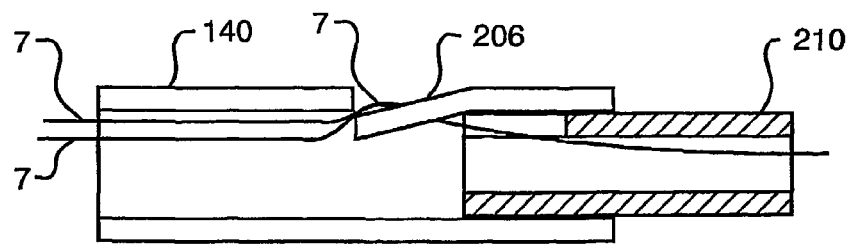
FIG. 68 is a sectional view of an assembled cylinder/hollow rod suture clip assembly with the cylinder having a secured rotatable flap according to a yet further embodiment of the invention.

FIGS. 66-68 show another embodiment using cylinder 140 and a hollow rod 210. In this embodiment, a flap 206 is formed in the sidewall of cylinder 140 by skiving the sidewall. Flap 206 has a flap aperture 208 formed therein. A distal end of flap 206 is bent downwardly so that it occupies part of the lumen of cylinder 140. Suture 7 is threaded through a distal end of cylinder 140 and through flap aperture 208 from a top side of flap 206 and out through a proximal end of cylinder 140. Suture 7 is then advanced through a rod lumen 212 of a hollow rod 210 that has an outer diameter that is sized to provide a friction fit with the inner wall of cylinder 140. Hollow rod 210 is advanced through cylinder 140 within which hollow rod 210 contacts a bottom proximal end of flap 206. Further advancement of hollow rod 210 forces flap 206 upwardly which captures suture 7 between flap 206 and the sidewall of cylinder 140 as shown in FIG. 68.

Figure 69:
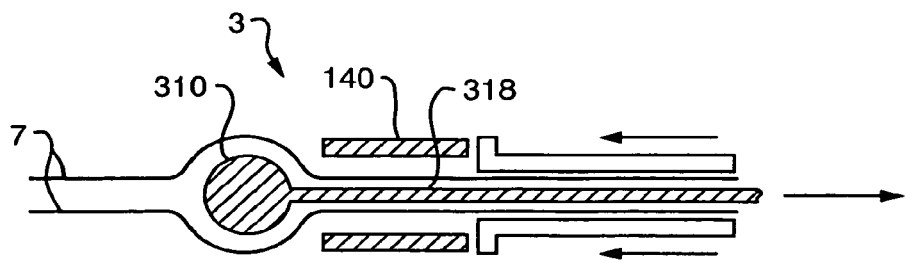
FIG. 69 is a side sectional view of an unassembled sphere-shaped wedge/cylinder suture clip assembly according to another embodiment of the invention.
Figure 70:
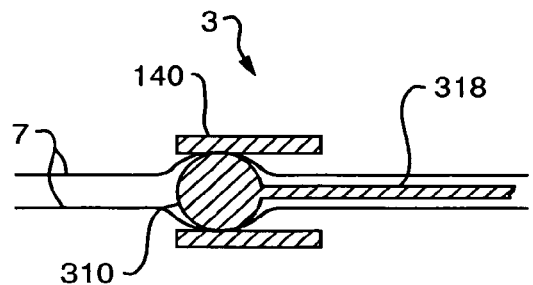
FIG. 70 is a side sectional view of an assembled sphere-shaped wedge/cylinder suture clip assembly according to another embodiment of the invention.

FIGS. 69-73 show a variety of embodiments of the wedge principle. FIGS. 69, 70 and 730 show wedge 310 conformed to the shape of a sphere. A wedge string 318 is attached to wedge 310 and is used to apply tension to force wedge 310 into a pliable version of cylinder 140. Preferably cylinder 140 is made of a material such as plastic that can be deformed to receive wedge 310 that has a diameter that is preferably greater than the diameter of the lumen of cylinder 100. The introduction of wedge 310 into cylinder 140 captures a present suture 7 between the interfacing surfaces of cylinder 140 and wedge 310.

Figure 71:
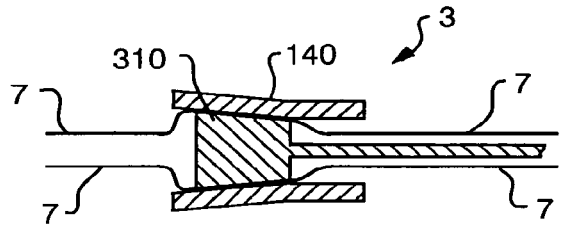
FIG. 71 is a side sectional view of a conical wedge/cylinder suture clip assembly according to yet another embodiment of the invention.
Figure 72:
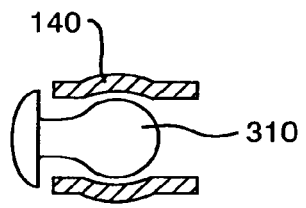
FIG. 72 is a side sectional view of an assembled bulbous plug/cylinder suture clip assembly according to a further embodiment of the invention.
Figure 73:
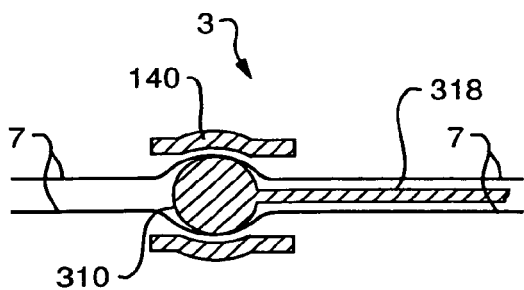
FIG. 73 is a side sectional view of an assembled sphere-shaped plug/cylinder suture clip assembly with the cylinder having an annular inner channel according to a still further embodiment of the invention.

FIGS. 71 and 72 show alternative embodiments of wedge 310 combined with cylinder 140. FIG. 71 shows wedge 310 being solid with a tapered sidewall. FIG. 72 shows wedge 310 with a bulbous proximal end and a domed cap distal end that has a diameter that is preferably greater than the inner diameter of cylinder 140. Again, suture 7 is captured by the mating surfaces of the components.

Figure 74:
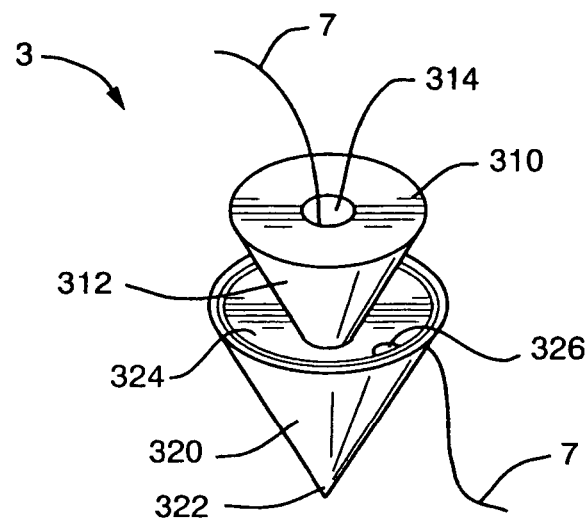
FIG. 74 is a perspective view of an unassembled wedge/cone suture clip assembly according to another embodiment of the invention.
Figure 75:
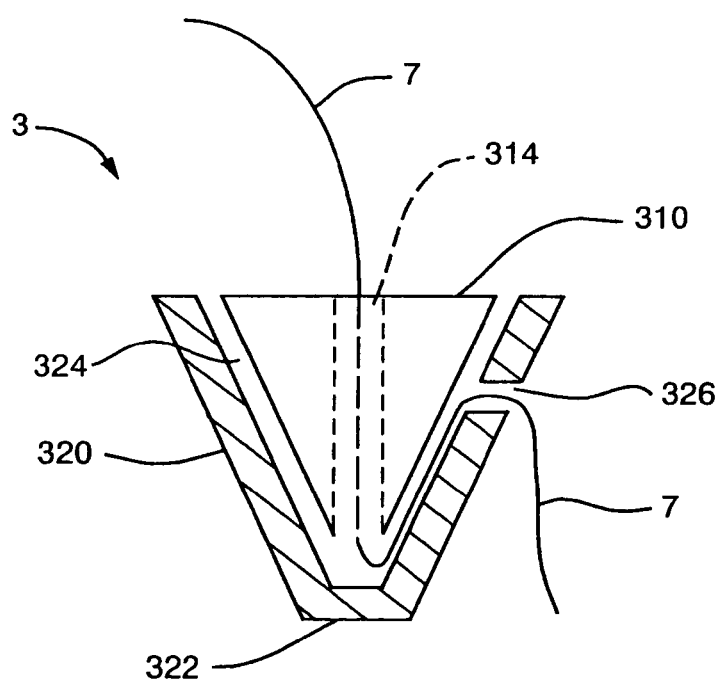
FIG. 75 is a sectional view of an assembled wedge/cone suture clip assembly according to another embodiment of the invention.

FIGS. 74 and 75 show a further embodiment of suture clip 3 comprised of wedge 312 and cone 320. Wedge 312 has central aperture 314 and cone 320 has a cone aperture 326 that is formed in the sidewall of cone 320. Cone 320 can be formed with a pointed or flat tip 322. In this embodiment, suture 7 is advanced through central wedge aperture 314, into a cone cavity 324 formed in cone 320 and out through cone aperture 326. Wedge 310 is then advanced into cavity 324 of cone 320, the interfacing surfaces of which capture suture 7. The further wedge 320 is advanced into cone 320 the greater the capture force on suture 7.

Figure 76:
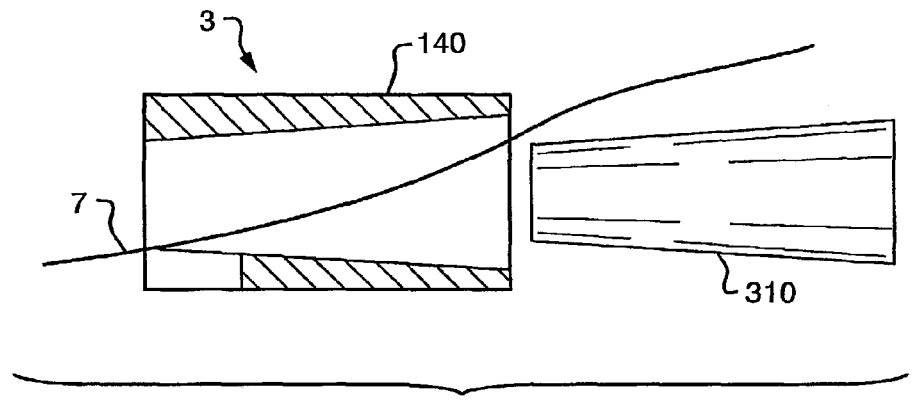
FIG. 76 is a side sectional view of an unassembled tapered wedge/cylinder suture clip assembly according to yet another embodiment of the invention.
Figure 77:
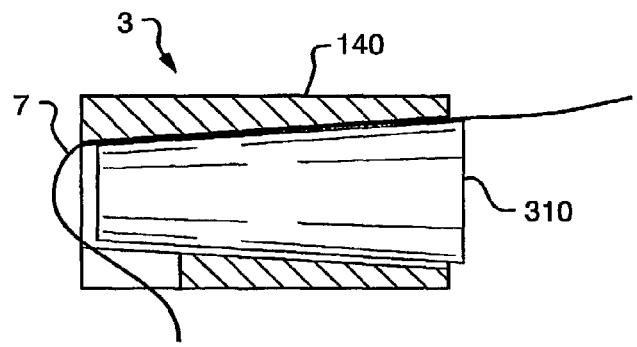
FIG. 77 is a side sectional view of an assembled tapered wedge/cylinder suture clip assembly according to yet another embodiment of the invention.
Figure 78:
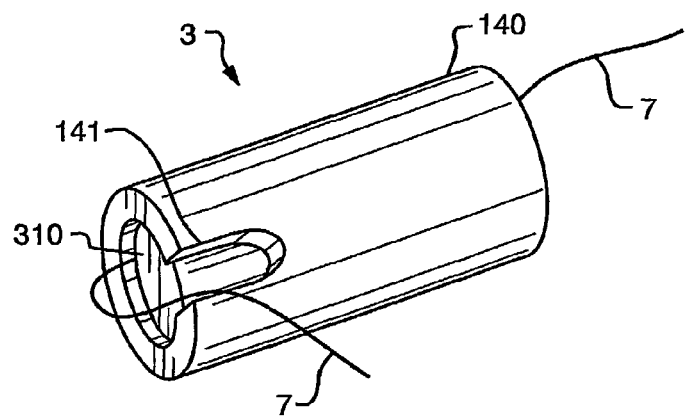
FIG. 78 is a perspective view of an assembled tapered wedge/cylinder suture clip assembly with a slot in the cylinder according to a further embodiment of the invention.

FIGS. 76-83 show additional embodiments of suture clip 3 using various shaped wedges. FIGS. 76 and 77 show cylinder 140 with a tapered wedge 310. Again, the interfacing surfaces of cylinder 140 and wedge 310 capturing suture 7 as shown in FIG. 77. FIGS. 78, 81, 82 and 83, show a similar embodiment however with cylinder 140 having a cylinder slot 141 formed on the sidewall and extending from, and opening on, an end of cylinder 140. As described for previous similar embodiments, suture 7 is placed in slot 141 before engagement of cylinder 140 and wedge 310.

Figure 79:
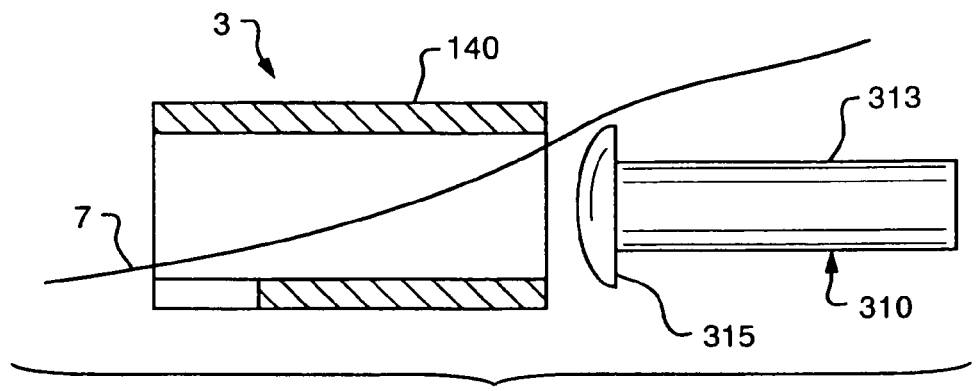
FIG. 79 is a side sectional view of an unassembled domed, flanged plug/cylinder suture clip assembly according to a still further embodiment of the invention.
Figure 80:
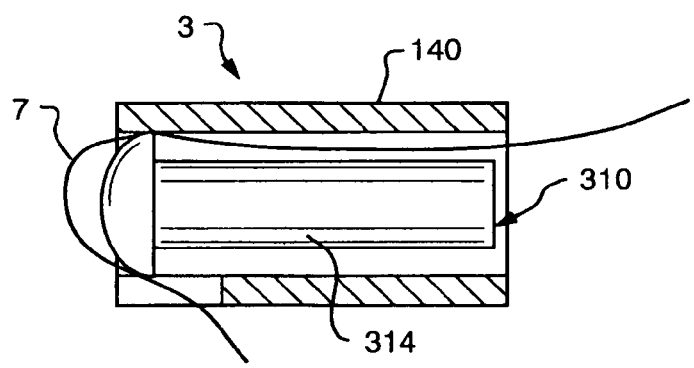
FIG. 80 is a side sectional view of an assembled domed, flanged plug/cylinder suture clip assembly according to a still further embodiment of the invention.
Figure 81:
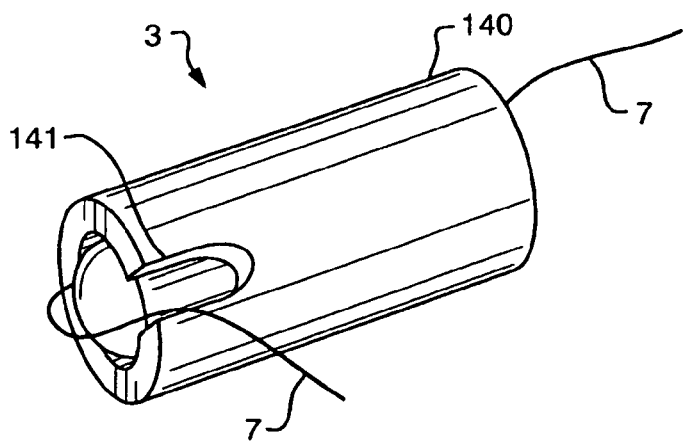
FIG. 81 is a perspective view of a cylinder component with a slot according to a further embodiment of the invention.
Figure 82:
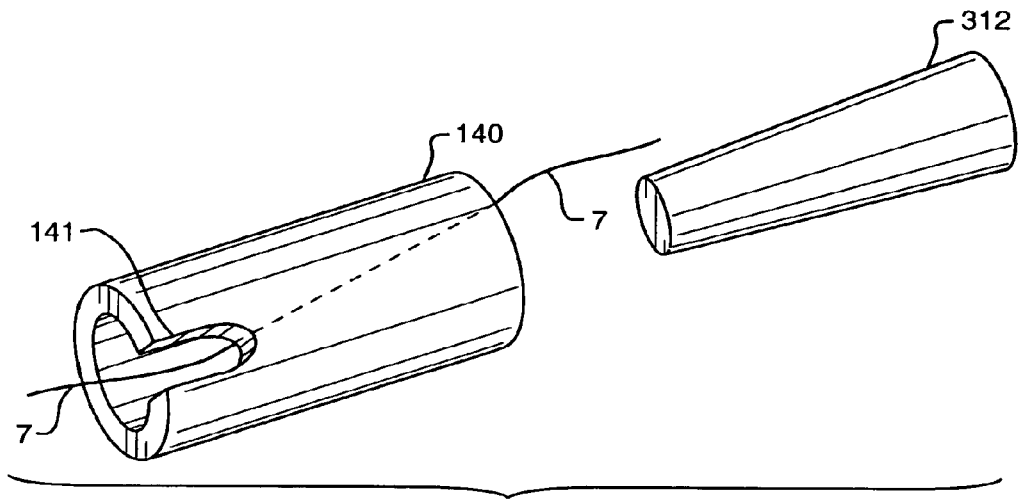
FIG. 82 is a perspective view of a tapered wedge/cylinder suture clip assembly with a slot in the side of the cylinder according to a further embodiment of the invention.
Figure 83:
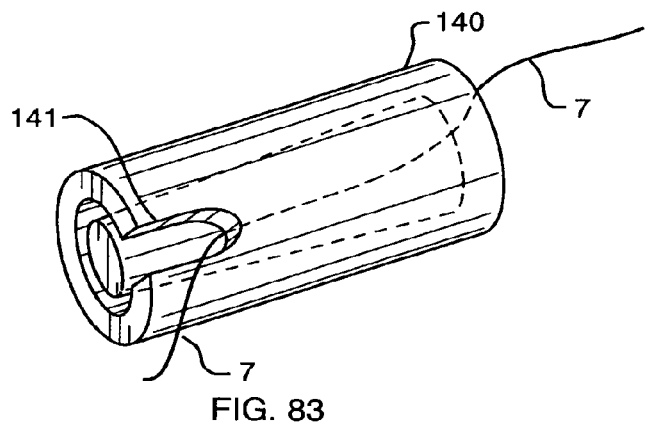
FIG. 83 is a perspective view of an assembled tapered rod/cylinder suture clip assembly according to a further embodiment of the invention.

FIGS. 79 and 80 show a yet further embodiment of suture clip 3 in which wedge 310 has a cylindrically shaped main body 313 and a domed and flanged distal end 315. Suture 7 is captured by the interfacing surfaces of distal end 315 and the inner wall of cylinder 140.

Figure 84:
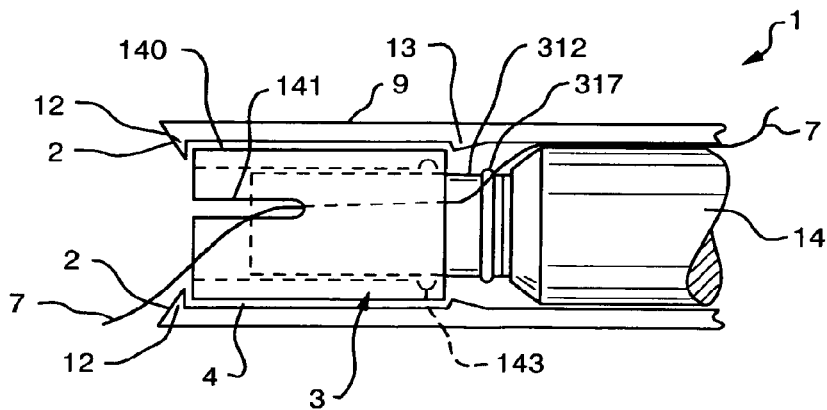
FIG. 84 is a side sectional view of a tapered wedge/cylinder suture clip assembly in a delivery device according to a further embodiment of the invention.
Figure 85:
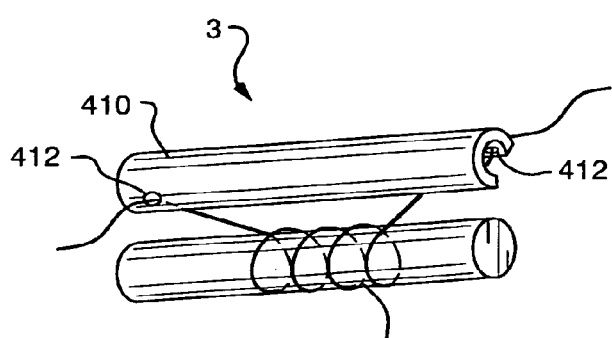
FIG. 85 is a perspective view of an unassembled rod/half-sleeve suture clip assembly according to another embodiment of the invention.

FIG. 84 shows device 1 with a suture clip 3 loaded into chamber 4. Cylinder 140 is shown being confined by distal tangs 12 while pusher 14 advances wedge 312 through the lumen of cylinder 140. An annular cylinder channel 143 is formed on the inner wall of cylinder 140 to receive in mating engagement, an annular flange 317 formed on a proximal end of wedge 312. Suture 7 enters cylinder 140 via cylinder slot 141 and out the proximal end of cylinder 140. The interfacing surfaces of cylinder 140 and wedge 312 capture suture 7.

Figure 86:
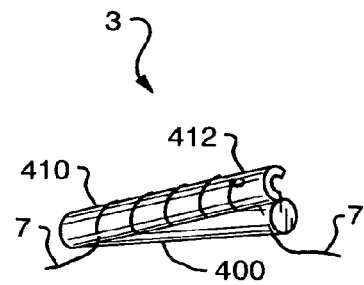
FIG. 86 is a perspective view of a partially assembled rod/half-sleeve suture clip assembly according to another embodiment of the invention.
Figure 87:
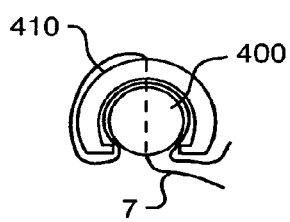
FIG. 87 is a front view of an unassembled rod/half-sleeve suture clip assembly according to another embodiment of the invention.
Figure 88:
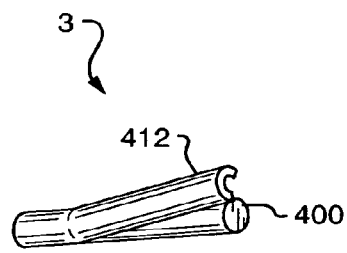
FIG. 88 is a perspective view of an unlocked joined rod/half-sleeve suture clip assembly according to another embodiment of the invention.
Figure 89:
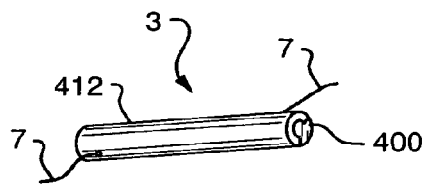
FIG. 89 is a perspective view of a locked joined rod/half-sleeve suture clip assembly according to another embodiment of the invention.
Figure 92:
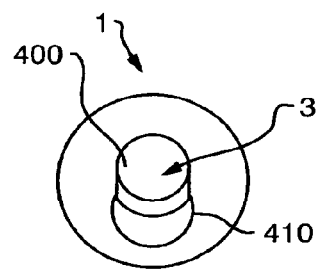
FIG. 92 is a front perspective view of a partially locked joined rod/half-sleeve suture clip assembly according to another embodiment of the invention.

A final category of suture clip embodiments is shown in FIGS. 85 through 102 that involve a cylinder or rod being wrapped with suture 7 and captured with external semicircular sleeves. FIGS. 85-89 show a rod 400 and a sleeve 410 that is preferably semicircular and more preferably has a hyper semi-circular cross sectional shape that is sized to releasably lock onto rod 400. Sleeve 410 has sleeve apertures 412 that are preferably formed proximal to distal and proximal ends of sleeve 410. Suture 7 is threaded through a distal member of the sleeve apertures 412 then wound around rod 400 then threaded through a proximal member of the sleeve apertures 412. Sleeve 410 is then clipped onto rod 400 as shown in FIGS. 86 and 87. FIGS. 88, 89 and 91-95 show an embodiment in which rod 400 and sleeve 410 are joined at a proximal end. In this embodiment suture clip 3 is made of a material that allows sleeve 410 to be flexed from an open position to a closed position.

Figure 90:
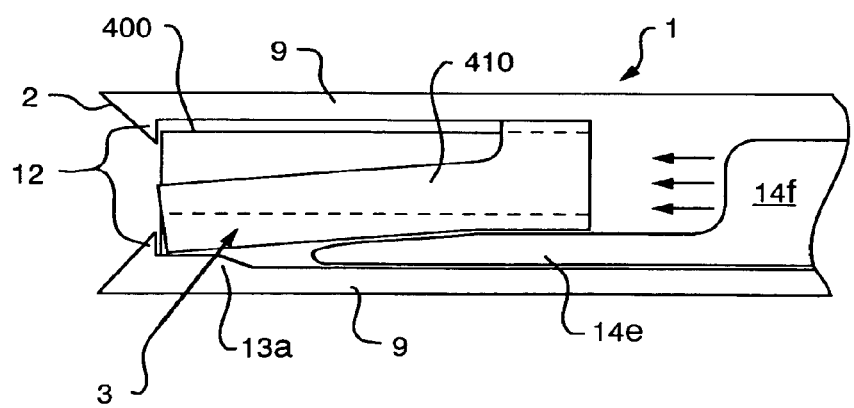
FIG. 90 is a side sectional view of an unlocked rod/half-sleeve suture clip assembly in a delivery device according to another embodiment of the invention.
Figure 91:
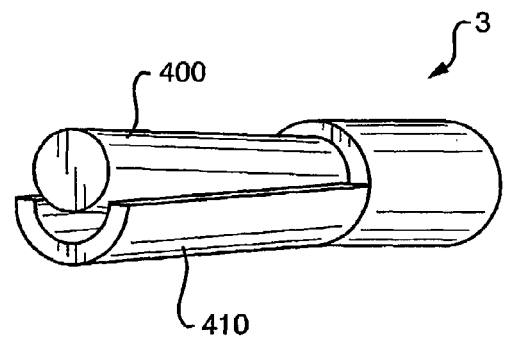
FIG. 91 is a perspective view of a partially locked joined rod/half-sleeve suture clip assembly according to another embodiment of the invention.
Figure 93:
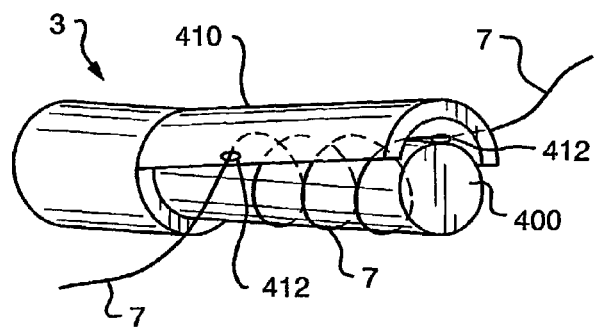
FIG. 93 is a perspective view of a partially locked joined rod/half-sleeve suture clip assembly with the half-sleeve having a suture aperture according to a further embodiment of the invention.
Figure 94:
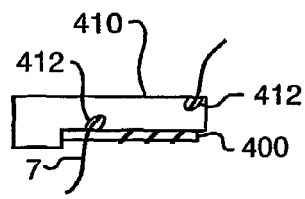
FIG. 94 is a side elevational view of a locked joined rod/half-sleeve suture clip assembly with the half-sleeve having a suture aperture according to a further embodiment of the invention.
Figure 95:
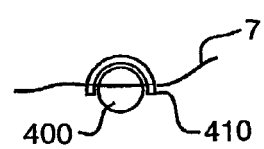
FIG. 95 is a front view of a locked joined rod/half-sleeve suture clip assembly with the half-sleeve having a suture aperture according to a further embodiment of the invention.
Figure 96:
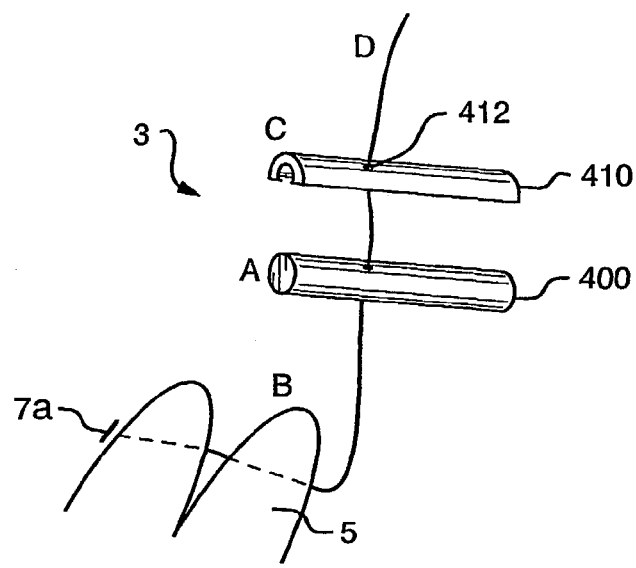
FIG. 96 is a perspective view of an unassembled rod/half-sleeve suture clip assembly with the half-sleeve having a suture aperture according to a yet further embodiment of the invention.
Figure 97:
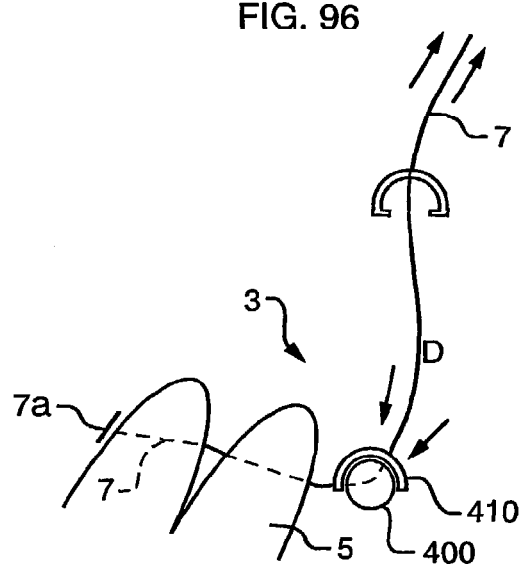
FIG. 97 is an end view of an unassembled rod/half-sleeve suture clip assembly according to a yet further embodiment of the invention.
Figure 98:
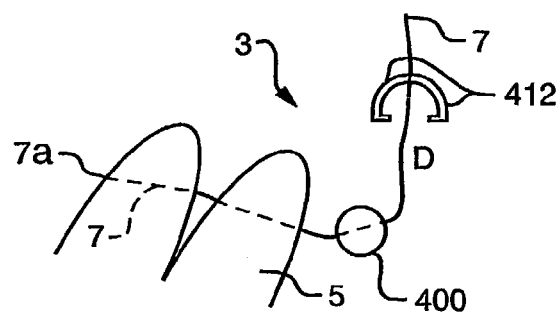
FIG. 98 is an end view of a partially assembled rod/half-sleeve suture clip assembly according to a yet further embodiment of the invention.
Figure 99:
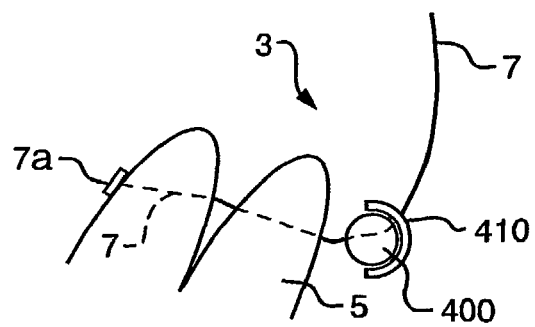
FIG. 99 is an end view of an assembled and cinched rod/half-sleeve suture clip assembly according to a yet further embodiment of the invention.
Figure 100:
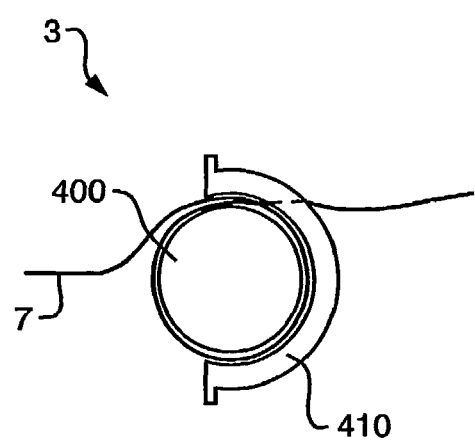
FIG. 100 is an end view of an assembled rod/half-sleeve suture clip assembly according to a yet further embodiment of the invention.

FIGS. 90 and 91 show a modification of device 1 that can be used to lock suture clip that incorporates a rod and mating sleeve. As shown, rod 400 and sleeve 410 are mounted in chamber 4. Pusher 14f has a distally extending tapered segment 14e that when advanced distally, forces sleeve 410 to rotate toward rod 400 until sleeve 410 is locked onto rod 400. A tapered proximal tang 13a provided proximally to distal tang 12 is situated to contact segment 14e. Full distal advancement of segment 14e results in segment 14e riding along tang 13e that, in turn, causes the outward flexion of finger 9 which releases suture clip 3.

FIGS. 96-100 show suture clip 3 in various stages of advancement from a pre-locked position (FIG. 96) to an intermediate position (FIGS. 97 and 98) to a locked position (FIGS. 99-100) adjacent to tissue 5. The process begins by advancing rod 400 down suture 7 toward tissue 5 with a pusher (not shown). Once rod 400 reaches tissue 5, tension is applied to suture 7. Sleeve 410 is then advanced distally along suture 7 with a pusher (not shown) until reaching rod 400. Alternatively, rod 400 and sleeve 410 can be advanced simultaneously by providing sleeve 410 with a suture contacting surface that has additional friction. Any slack in suture 7 is captured between rod 400 and sleeve 410 when locked together. The suture 7 is then severed by the pusher at a point proximal to the suture clip 3. The suture capturing effect can be enhanced by winding suture 7 about rod 400 before locking sleeve 410 to rod 400. In alternate embodiments, the mating surfaces of rod 400 and sleeve 410 can be textured or provided with mating projections and cavities to enhance the frictional grasp of suture 7. It should be noted that a suture tag 7a can be used to anchor a distal end of suture 7.

Figure 101:
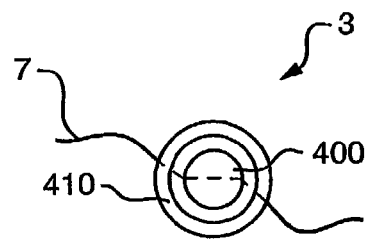
FIG. 101 is a front view of a joined rod/half-sleeve suture clip assembly according to a yet further embodiment of the invention.

FIGS. 101 and 102 show an additional embodiment of suture clip 3. FIG. 102 shows rod 400 about which suture 7 is wound. Clamping jaws 500 are closed to capture suture 7 between the interfacing surfaces of rod 400 and clamping jaws 500. One method that can be used to close clamping jaws 500 employs device 1 with the modifications shown for the rod/sleeve suture clip embodiment. The open end of clamping jaws 500 are positioned in the distal end of chamber 4 against distal tangs 12.

Figure 103:
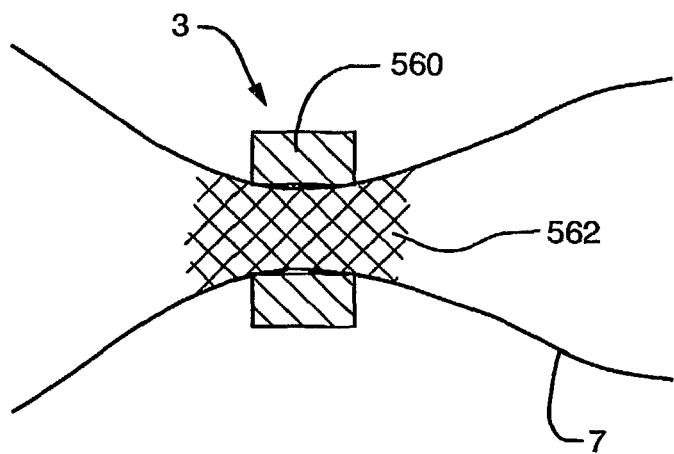
FIG. 103 is a side sectional view of an assembled mesh plug/rigid ring suture clip assembly according to one embodiment of the invention.
Figure 104:
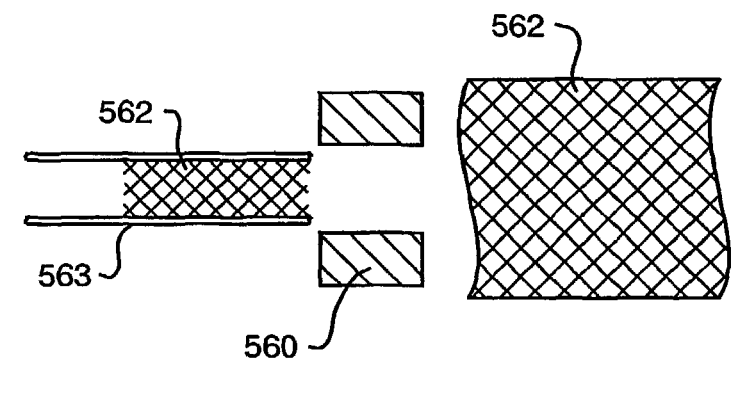
FIG. 104 is a side sectional view of a mesh plug delivery catheter with a mesh plug positioned within adjacent to a rigid ring and an expanded mesh plug according to one embodiment of the invention.
Figure 105:
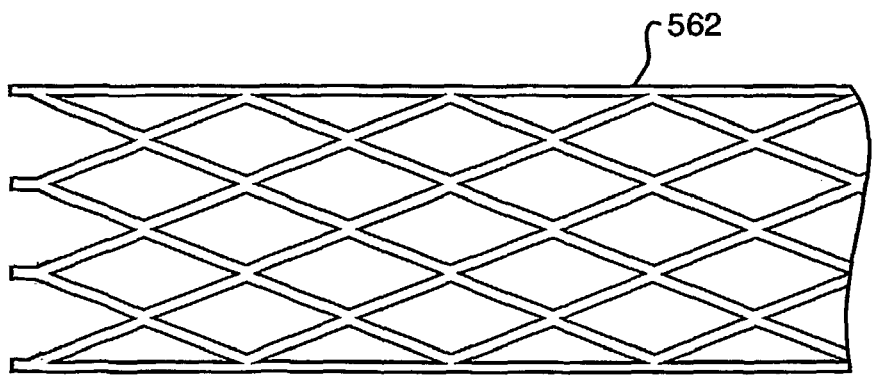
FIG. 105 is a side sectional view of a mesh plug suture clip component according to one embodiment of the invention.
Figure 106:
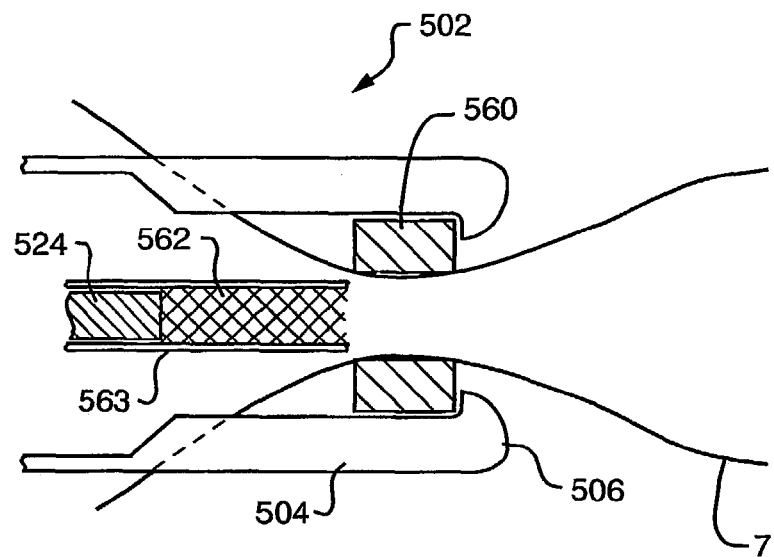
FIG. 106 is a side sectional view of an undeployed mesh plug of mesh plug/rigid ring suture clip assembly with the mesh plug positioned in a delivery catheter positioned within a suture clip delivery device.
Figure 107:
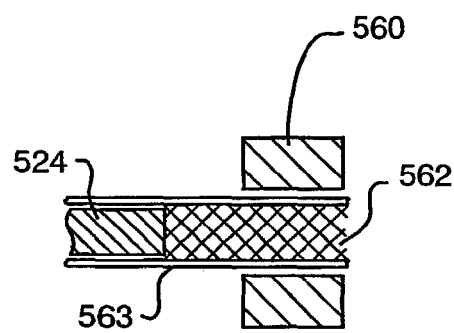
FIG. 107 is a side sectional view of an undeployed mesh plug of a mesh plug/rigid ring suture clip assembly with the mesh plug positioned in a delivery catheter positioned within the ring.
Figure 108:
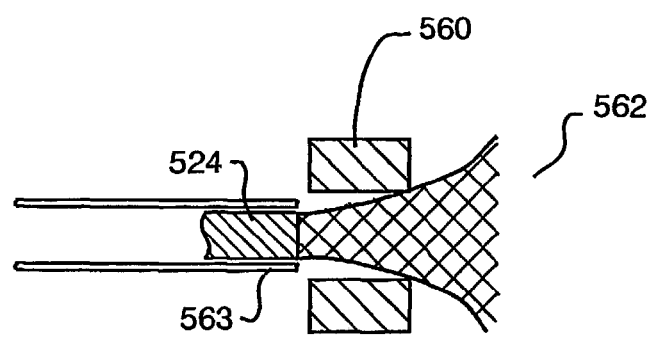
FIG. 108 is a side sectional view of a partially deployed mesh plug of a mesh plug/rigid ring suture clip assembly positioned in a delivery device including a mesh delivery catheter with pusher according to another embodiment of the invention.

FIGS. 103-120 illustrate suture clips having either expandable plugs or expandable rings combined with a rigid counterpart ring or plug, respectively. FIGS. 103-105 show a suture clip 3 comprising a ring 560 and a mesh plug 562. Ring 560 is made from a relatively rigid material such as polypropylene to withstand expanding forces generated by plug 562. Plug 562 is preferably made from an expandable material such as nitinol or an elastomeric material into the mesh pattern shown in FIG. 105. Plug 562 is configured so that the nitinol mesh has a relaxed state that has an outer diameter that exceeds the inner diameter of ring 560. Suture 7 is captured between an inner wall of ring 560 and an outer surface of plug 562 via the radial outward force generated by ever expanding nitinol based plug 562.

FIGS. 106-113 show the delivery of mesh plug 562 into ring 560. The process begins by preloading ring 560 into a suture clip delivery device 502. Resilient collet fingers 504 formed at a distal end of delivery device 502, have distal tangs 506 that provide a temporary stop to arrest distal movement of ring 560 prior to cinching with plug 562. Suture 7 is threaded through ring 560 and through delivery device 502. A plug delivery catheter 563 dimensioned to slide axially through a central bore in delivery device 502, is preferably preloaded at a distal end with a plug 562 in a compressed state. Catheter 563 is advanced until in close proximity to a proximal edge of ring 560. A ring pusher 524 dimensioned to slide axially within catheter 563 is advanced distally through catheter 563 to force ring 562 out of catheter 563 and into ring 560.

Figure 109:
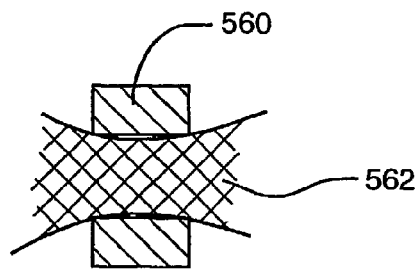
FIG. 109 is a side sectional view of an assembled mesh plug/rigid ring suture clip assembly according to another embodiment of the invention.
Figure 110:
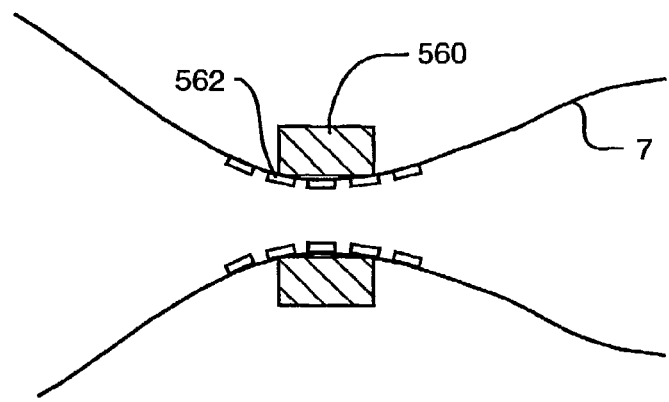
FIG. 110 is a side sectional view of an assembled ribbon plug/rigid ring suture clip assembly according to a yet another embodiment of the invention.
Figure 111:
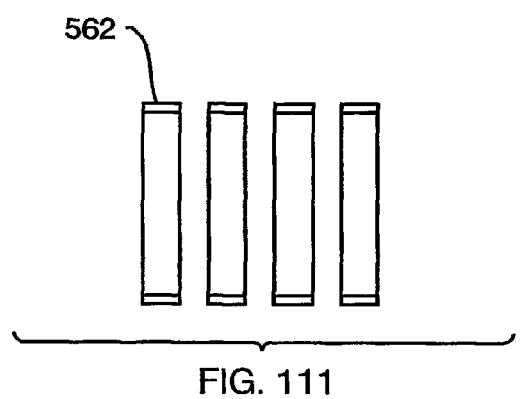
Figure 112:
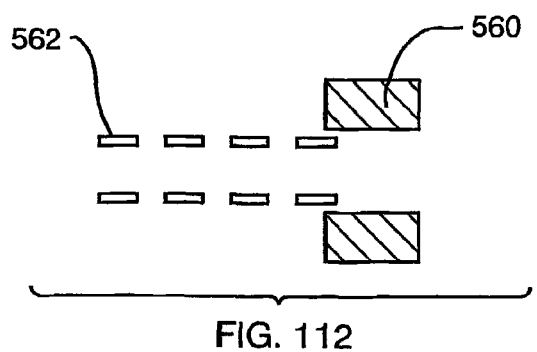
Figure 113:
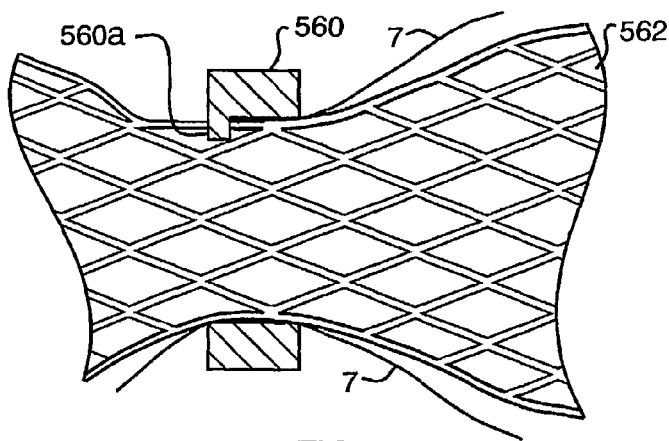
Figure 114:
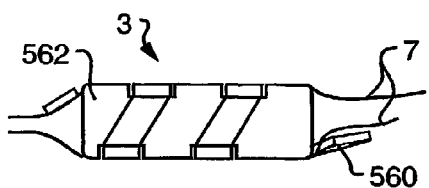
Figure 115:
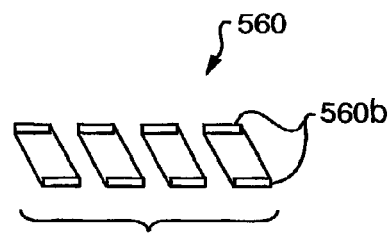
Figure 116:
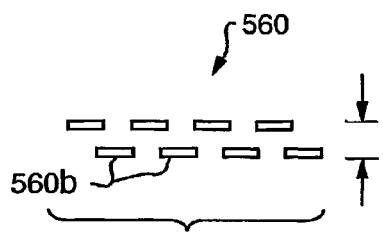
Figure 117:
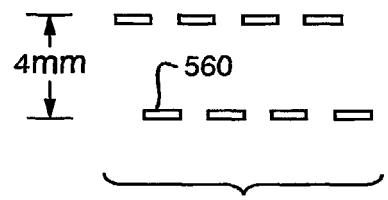
Figure 118:
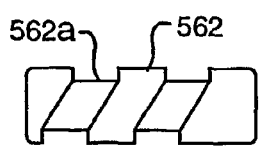

With the distal exit of plug 562 from catheter 563, the radially restraining force provided by an inner wall of catheter 563 is eliminated thereby allowing plug 562 to expand. Suture 7 is captured and held by the friction generated by plug 562 expanding into an inner wall of ring 562. As shown in FIGS. 109 and 110, plug 562 is preferably longer than ring 560 so that the ends of plug 562 preferably expand beyond the outside diameter of ring 560 to provide a locking function to prevent relative axial movement of plug 562 to ring 560. Optionally as shown in FIG. 113, ring 560 can be formed with an anti-migration tab 560a that extends inwardly from the inner wall of ring 560. Tab 560a operates to prevent relative axial movement of plug 562 by engaging one or more web apertures formed in the mesh structure of plug 562.

FIGS. 114-120 show an alternate embodiment of the expandable suture clip component design. In this embodiment, plug 562 is the rigid component and ring 560 is a compressible component. Preferably, plug 562 is formed with diagonal channels 562a formed on an outer surface while ring 560 is formed as a ribbon dimensioned so that the spacing between adjacent ribbon sections 560b corresponds with the spacing of the plug channels 562a. With this embodiment, ring 560 is stressed into an initial open, large diameter state for delivery onto plug 562. Following the insertion of suture 7 into ring 560, plug 562 is inserted into ring 560 so that suture 7 is positioned between the outer wall of plug 562 and the inner surfaces of ring 560. Once positioned, ring 560 is allowed to transition to a smaller diameter relaxed state that causes the migration of the individual ribbon sections 560b into plug channels 562a. The tortuous path followed by suture 7 by virtue of the plug channels 562a coupled with the frictional force generated by the compression of ring 560 results in suture clip 3 being secured against axial displacement relative to suture 7.

Figure 120:
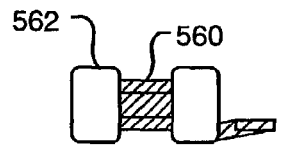
Figure 119:
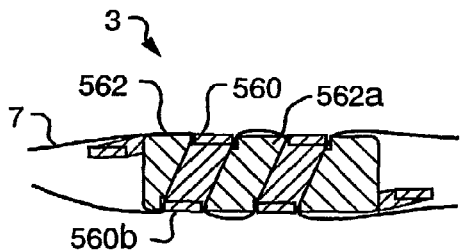
Figure 121:
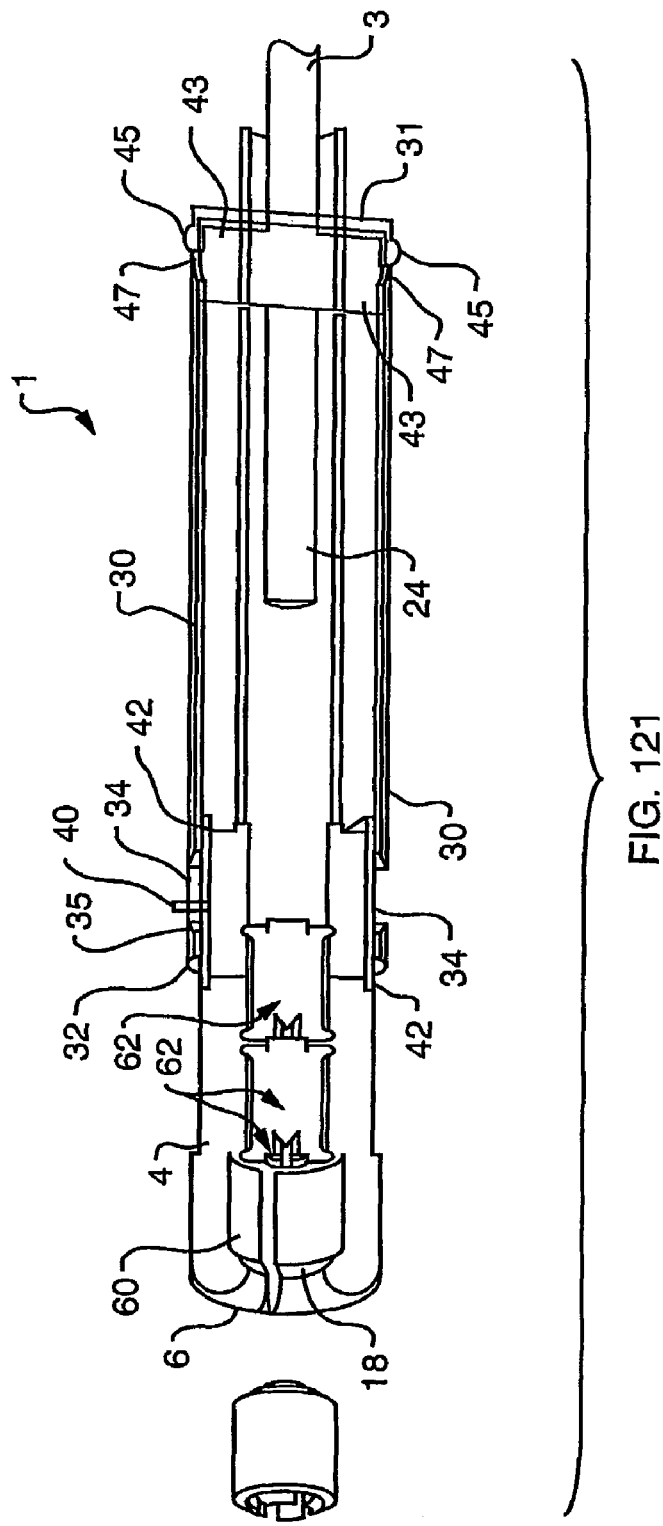
Figure 122:
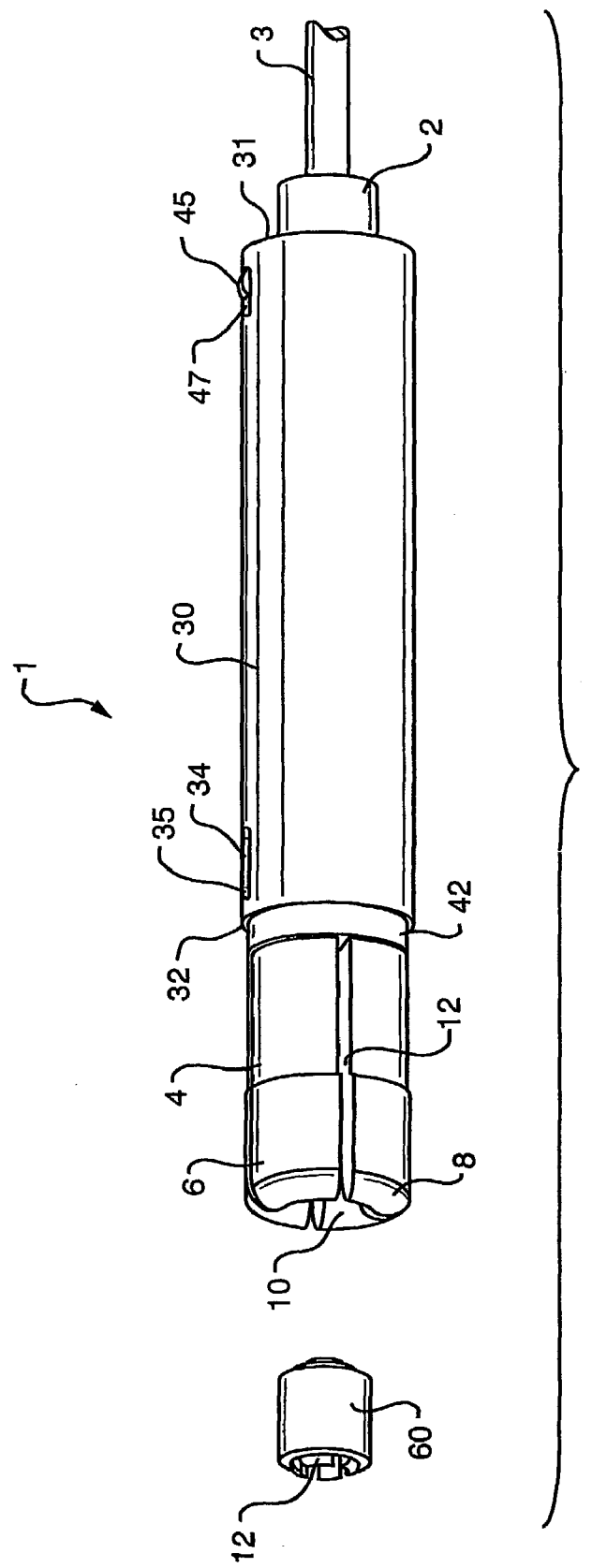

A further embodiment of plug 562 is shown in FIG. 120. In this embodiment, plug 562 is formed with enlarged ends that give plug 562 a "dumbbell" shape. The diametrically enlarged ends provide axial stops for mesh ring 560.

Referring to FIGS. 121-125, the distal end of a low profile single pusher suture clip delivering and locking catheter designed primarily headless suture clip assemblies is shown generally as 1. A catheter distal end is comprised primarily of a collet 2 to which the other components of distal end 1 are attached. Collet 2 is essentially a cylinder with two or more collet fingers 4 extending distally from a distal end of collet 2. Collet fingers 4 are biased in an open position. Extending radially inwardly from a distal end of each collet finger 4 is a collet finger flange 6 that functions as a stop to arrest distal advancement of a suture clip loaded into collet 2. The combination of the distal end of collet 2, collet fingers 4 and distal flanges 6 define a collet cage within which the components of a suture clip are releasably encapsulated for delivery to a sutured tissue site. The cage further functions to align the suture clip components for assembly.

In a preferred embodiment, collet finger flanges 6 have radiused outer distal edges 8 to minimize trauma to a patient and radiused inner distal edges 10 to ease loading of suture clip components. In a preferred embodiment, outer distal edges 8 extend radially outwardly beyond outer collet finger walls 4 to function as a stop for an outer sliding sleeve 30 described below. Inner proximal faces of collet finger flanges 6 are oriented to a longitudinal axis of collet fingers so that a plane occupied by flange proximal surfaces 18 forms an angle from about 90° to about 135° and preferably about 128° to optimally balance the need to provide a stopping function against the need to not hinder suture clip deployment from the delivery catheter. Optionally, collet finger flanges 6 can be formed to extend radially outwardly from the outer wall of collet fingers 4 to act as a distal stop for a sliding sleeve 30.

Finger slots 12 are formed between and defined by collet fingers 4 and function as egress ports for sutures threaded through the components of a suture clip loaded into the collet cage. Because collet fingers 4 are biased in an open position, a radially constraining force need only be applied to move the fingers from an open, suture clip loading/releasing position to a closed, suture clip confining position. Alternatively, finger collets 4 can be biased in a closed position.

The distance between a proximal face of collet finger flanges 6 and the distal end of the body of collet 2 is set to preferably accommodate at least one set of unassembled suture clip components along with two unassembled suture clip plugs 62. This distance can be modified to accommodate different numbers of suture clip plugs.

Situated within a hollow chamber defined by the inner walls of collet 2 is a cylindrically shaped pusher 24. Pusher 24 slides freely within collet 2. Pusher 24 is preferably adapted to matingly engage a proximal end of a suture clip plug situated in the collet cage. Distal advancement of pusher 24 engages the suture clip plug and drives the suture clip plug distally into a suture clip ring. Collet finger flanges 6 function as a stop for the suture clip ring so that the distal axial force applied causes engagement of the suture clip components.

Pusher 24 is formed with diametrically opposed guide tabs 43 that ride axially within diametrically opposed channels formed in the inner walls of collet 2. Extending radially outwardly from guide tabs 43 are depressible finger tabs 45.

Situated in coaxial relationship with and freely sliding about collet 2 is outer sliding sleeve 30 that performs at least two functions; providing radial force against collet fingers 4 to maintain the fingers in a closed position during suture clip delivery to a tissue site to minimize potential trauma that could be caused by open collet fingers and providing a means to sever the tail ends of a suture that has been secured with a suture clip. When advanced distally, sliding sleeve 30 encompasses collet fingers 4 and restricts radial movement of the fingers regardless whether the fingers are biased in an open or closed position.

When proximally retracted, sliding sleeve 30 severs directly or cooperates with other components to sever suture material proximal to a secured suture clip. In one embodiment, a distal end 35 of suture slot 34 engages the suture and carries it toward a distal end of the body of collet 2. When the distal end of suture slot 34 travels past the distal end of the body of collet 2, the suture is severed. In another embodiment, sliding sleeve 34 interacts with a fixed cutter 42, described below, to sever the suture tail ends. In yet a further embodiment suture slot distal end 35 is sharpened to perform the severing function when sliding sleeve 30 is proximally retracted.

Diametrically opposed sliding sleeve locking slots 47 are formed in the outer cylindrical wall of sliding sleeve 30 in close proximity to a proximal end of sliding sleeve 30. Locking slots 47 are adapted to receive finger tabs 45 of pusher 24. Interlocking of finger tabs 45 and locking slots 47 provide a means to retract sliding sleeve 30 with pusher 24. To retract sliding sleeve 30, pusher 24 is proximally retracted until it contacts a proximal end 31 of sliding sleeve 30. Upon contact finger tabs 45 engage locking slots 47 which allows proximal retraction of sliding sleeve 30 via proximal retraction of pusher 24. To advance sliding sleeve 30, finger tabs 45 have to be manually depressed out of the patient. Sliding sleeve 30 can then be manually advanced to contain collet fingers 4 in a closed position.

In an alternate embodiment as shown in FIGS. 132 and 133, a pusher head 24a extends from a distal end of pusher 24. Pusher head 24a has portions defining an axially oriented sleeve pin slot 24b that is adapted to receive in sliding engagement, a sliding sleeve pin 40a. Sliding sleeve pin 40a extends radially inwardly from sliding sleeve 30 and is dimensioned to freely slide axially within sleeve pin slot 24b. Sleeve pin slot 24b is positioned within pusher head 24a so that the pusher 24/pusher head 24a assembly can be advanced distally sufficient to completely cinch the suture clip assembly without advancing sliding sleeve 34 past the distal end of collet fingers 4. With this arrangement, a proximal end of sleeve pin slot 24b acts as a stop for sliding sleeve 30 and thereby eliminates the need for collet finger flanges 6 to provide a distal stop for sliding sleeve 30. A distal end of sleeve pin slot 24b is positioned so that retraction of the pusher 24/pusher head 24a assembly causes the distal end of sleeve pin slot 24b to engage sliding sleeve pin 40a and retract sliding sleeve 30 a sufficient axial distance to allow release of the cinched suture clip assembly. A subsequent forward advancement of the pusher 24/pusher head 24a assembly causes the proximal end of sleeve pin slot 40b to engage sliding sleeve pin 40a that translates the distal motion of pusher 24 into a distal motion of sliding sleeve 34 to retract collet fingers 4 radially inwardly for full retraction of delivery device 1 out of the patient.

At least one suture slot 34 is formed toward a distal end 32 of sliding sleeve 30 to provide egress for excess suture material that typically extends beyond the orifice through which the catheter is inserted. It is important that finger slots 12 and suture slots 34 are at least partially aligned to allow a path for excess suture material to exit the suture clip delivery device. To accomplish alignment with embodiments lacking sliding sleeve pin 40a, suture slot 34 functions as an alignment slot to receive an alignment pin. An alignment pin 40 is affixed to collet 2 and dimensioned to freely slide within alignment suture slot 34. The length of alignment slot 34 limits the proximal and distal travel of sliding sleeve 30. Alignment pin 40 is positioned on collet 2 at a point proximal to the distal edge and through a fixed cutter 44, if present. Suture slot 34 is positioned in sliding sleeve 30 such that at least one finger slot 12 and suture slot 34 are at least partially aligned along their longitudinal and radial axes. Preferably two diametrically opposed sets of finger slots 12 and suture slots 34 are provided to allow egress for each end of a suture. Only one alignment pin 40 need be provided to accomplish radial alignment.

An optional feature of the presently described embodiment is a fixed cutter 42. Cutter 42 is preferably a metallic ring formed about and affixed to collet 2 that has a distal edge 44 that is sufficiently sharp to sever suture material. The ring is used for embodiments that are preferably injection molded. However, filled or engineered plastics can be used to obviate the need for fixed cutter 42.

For the single pusher embodiment, a conventional control handle (not shown) with a single pusher knob attached directly to the collet cage is used to advance and retract pusher 24. The control handle does not form a part of the invention.

To load suture clip components in the single pusher embodiment, pusher 24 is fully retracted so that sliding sleeve 30 is engaged and proximally retracted to remove the radial constraint of collet fingers 4 which expand into an open position.

With collet fingers 4 arranged in an open position, two stackable suture clip plugs can be placed in the collet cage. Next, the ends of a suture 80 that has been used to stitch tissue in the internal regions of an individual are threaded through a suture clip ring and into thread apertures formed in a suture clip plug. The suture ends are then fed through either the same or separate sets of finger slots 12 and suture slots 34 so that the ends of the suture are arranged external to the suture clip delivery catheter. The suture clip plug 62 is then placed in a proximal end of the collet cage distal to the first two suture clip plugs 62 and the suture clip ring 60 is placed in a distal end of the collet cage where the ring preferably engages at least one of the collet ring flanges 6 to prohibit distal travel of the ring. It is to be understood that the collet cage can be sized to accommodate a plurality of suture clip plugs that can be stacked for deployment into suture clip rings that must be loaded one per suture clipping procedure.

With the suture clip components loaded, pusher 24 engaged to sliding sleeve 30 via the engagement of finger tabs 45 and locking slots 47 is distally advanced until sliding sleeve 30 reaches its maximum distal advancement point. At this point, due to the length of pusher 24, pusher 24 cannot engage the next suture clip plug 62 until finger tabs 45 are depressed to release sliding sleeve 30 that enables the operator to distally reposition pusher 24. Sliding sleeve 24 is sized so that locked engagement with sliding sleeve 30 prevents the distal end of pusher 24 from coming into contact with the next suture clip plug without being disengaged from sliding sleeve 30. This configuration effectively captivates the suture clip components for delivery to the sutured tissue site.

To operate the single pusher embodiment as shown in FIGS. 140-146, the control knob attached to pusher 24 is distally advanced. This causes a distal end of pusher 24 to engage the most proximal suture clip plug 62. The axial force generated is transferred through the two most proximal suture clip plugs 62 to the third most distal suture clip plug 62 that, in turn, engages suture clip plug 60 so that a complete suture clip is formed and cinched in close proximity to the stitched tissue. Once pusher 24 is maximally advanced to a bottom out position, the control knob is proximally retracted to engage sliding sleeve 30 as described above. Proximal retraction of sliding sleeve 30 severs the ends of suture 80 at a point proximal to the assembled suture clip via the interaction of the distal end of suture slot 34 and either the distal edge 44 of cutter 42 or the distal edge of the body of collet 2. To remove the catheter from the patient, pusher 24 is again proximally advanced. Due to the one-way interaction of finger tabs 45 and locking slots 47, distal advancement of pusher 24 causes sliding sleeve 30 to be advanced to again radially constrain collet fingers 4. Pusher 24 is distally advanced until sliding sleeve 30 reaches maximum advancement. At this point the catheter can be safely removed from the patient.

To begin another cycle, a suture clip ring is loaded into the collet cage. In one embodiment, a ring loading rod or mandrel (not shown) is used to load rings 60 into the distal end of the collet cage. The rod has a diameter that is sufficiently less than the inside diameter of the rings 60 to allow the free movement of rings 60 from the rod into the open collet cage. To insert a ring, the rod is forced into the radiused finger collet flanges 6 until it stops. The entering ring 60 has a diameter that is greater than the inner diameter of the finger collet flanges 6 that causes the flanges to flex inwardly. When the ring 60 is advanced proximally past the proximal faces 18 of flanges 6, the flanges flex back into their initial position and captivate the ring. The rod is then removed. To prepare for another suture clip assembling and cinching cycle, sliding sleeve 30 is released from pusher 24 and distally advanced to radially constrain collet fingers 4.

In another embodiment shown in FIG. 126, a dedicated finger hold 76 is employed to advance and retract sliding sleeve 30. In this embodiment, a collect finger hold 74 situated at a proximal end of the collet cage provides a finger grasping point to effectuate relative movement of pusher 24 and sliding sleeve 30. A thumb ring 72 is provided at a proximal end of pusher 24. To advance pusher 24, finger hold 74 is grasped while thumb ring 72 is advanced relative to finger hold 74. This enables pusher 24 to engage a suture clip plug to commence engagement of the plug with a suture clip ring. Once pusher 24 has bottomed out (a condition that can be preset by the length of pusher 24 relative to collet 2) the suture clip is fully assembled with a captured suture.

To deploy the suture clip and sever the suture ends, a sliding sleeve finger hold 76 is grasped and retracted while maintaining hold of thumb ring 72. This severs the excess suture material. If the collet fingers are pre-biased in an open position, the collet fingers will spring open absent the radially constraining force of sliding sleeve 30. If finger collets 4 are pre-biased on the closed position, a modification to collet 2 and pusher 24 has to be employed. A ramp 16 is formed on an inside wall of collet 2 at a point proximal to the area where the suture clip components are placed in the collet cage. Ramp 16 tapers radially inwardly from a distal to a proximal end. A pusher taper 17 is provided proximal to the distal end of pusher 24 and adapted to engage ramp 16. Proximal retraction of pusher 24 engages ramp 16 that causes collet fingers 4 to open and release the completed suture clip. To begin a new cycle, suture clip components are loaded into the collet cage and pusher 24 is partially advanced to effectuate the disengagement of ramp 16 and pusher 24 which allow collet fingers 4 to return to the pre-biased closed position.

The suture clips used with the suture clip delivery catheter described herein have plugs without heads. In a preferred embodiment as shown in FIGS. 127-129, plug 62 that is preferably injection molded, has a main shaft 68 that is adapted to frictionally engage the inner walls of ring 60. Extending from the distal and proximal ends of plug 62 are a plurality of plug locking tabs 63 which have outer faces that are radiused about the edges to provide ease of advancement into ring 60 which is also preferably injection molded. Locking tabs 63 are formed with sufficient flexibility to distort to ease advancement into ring so that their overall diameter is reduced while traveling through ring 60. Once the distal most locking tabs emerge from the distal end of ring 60, preferably simultaneous with the contact of the proximal locking tabs 63 with the proximal end of ring 60, the distal locking tabs 63 spring back to their original radially expanded state. The diameter of the flanges is set to be greater than the outside diameter of ring 60 so that when fully radially expanded, locking tabs 63 situated on the proximal and distal ends of plug 62 cooperate to positively lock ring 60 in an axial direction as shown in FIG. 130.

To reduce the effort needed to advance suture 80 about plug 60, plug guide slots 67 are formed between the side surfaces of locking tabs 63. A central diverter 65 is formed extending from the central distal end of plug 60. Diverter 65 has tapered sidewalls that increase radially outwardly from a distal to a proximal end. This configuration facilitates tracking and the radial disposition of suture 80 into guide slots 67. In one embodiment, diverter 65 extends distally beyond the distal end of plug 62 and an engaged ring 60 so that when the assembled suture clip is appended to suture 80, diverter 65 contacts the sutured tissue and causes fibrosis which leads to a thickening of the tissue. It is believed that this enhances the therapeutic effect of the procedure in GERD patients.

To permit stacking of multiple plugs 62, a substantially cylindrical plug cavity 61 is formed on the distal end of plug 60 and a corresponding axially extending cylindrical plug projection 69 is formed in the proximal end. To ensure positive engagement, plug projection 69 is extended above plug locking tabs 63. Plug cavity 61 and plug projection 69 are sized to loosely mate when a plug cavity 61 in the distal end of one plug is aligned with a plug projection 69 of an adjacent plug. The size tolerances for the respective mating components are maintained sufficiently loose not to interfere with suture clip deployment but tight enough to provide axial and radial alignment during the application of compressive forces to join a plug to a ring in the delivering and locking catheter described herein.

In practice, diverter 65 feeds suture 80 into guide slot 67 that is sized to allow the free movement of plug 60 along suture 80. This configuration provides a suture clip plug that decreases the effort needed to advance the plug over the ends of a suture before loading into the suture clip delivering and locking device.

A further suture clip embodiment employs rings and plugs with interlocking ribs or scales. As shown in FIG. 131, ribs 90 are provided circumferentially about the inner wall of ring 60. Corresponding plug ribs 97 are provided about the outer sidewall of plug 62. The ribs are configured to allow for the advancement of the plug into the ring with minimal effort. The ribs are tapered to allow the plug to be inserted into the ring in a distal direction and create an interference that prevents or resists proximal retraction of plug 62 out of ring 60. The suture 80 becomes entrapped between the inter-engaging ribs. The depth of the scale feature as well as the angle or taper is dependent on the suture size, material and degree of locking needed such as the life expectancy of the individual. Significant profiles will provide higher holding forces that can also adversely affect the life expectancy of the captured suture. The hardness of the components also should be factored into the design. The profile selected is preferably easily molded on the plug with the mold pulling off in the correct fashion. The inner ring detail becomes less of a challenge with the use of a spiral rib that allows the mold pin to be unthreaded. Optionally, a proximal stop 94 can be employed to limit distal advancement of the plug absent plug locking tabs 63. In the embodiment shown in FIG. 131, plug projection 69 and plug cavity 61 are shown having mating convex and concave domed surfaces, respectively.

Referring to FIGS. 134-138, the distal end of a double pusher suture clip delivery and locking catheter is shown generally as 1. Catheter distal end 1 is comprised primarily of a collet cage 2 to which the other components of distal end 1 are attached. Collet cage 2 is essentially a cylinder with two or more collet fingers 4 extending distally from a distal end of collet cage 2. Extending radially inwardly from a distal end of each collet finger 4 is a collet finger flange 6 that functions as a stop to arrest distal advancement of a suture clip loaded into collet cage 2. The combination of the distal end of collet cage 2, collet fingers 4 and distal flanges 6 define a cage within which the components of a suture clip are releasably encapsulated for delivery to a sutured tissue site. The cage further functions to align the suture clip components for assembly.

In a preferred embodiment, collet finger flanges 6 have radiused outer distal edges 8 to minimize trauma to a patient and radiused inner distal edges 10 to ease loading of suture clip components. In a preferred embodiment, outer distal edges 8 extend radially outwardly beyond outer collet finger walls 14 to function as a stop for an outer sliding sleeve 30 described below. Inner proximal faces of collet finger flanges 6 are oriented to a longitudinal axis of collet fingers so that a plane occupied by flange proximal surfaces 18 forms an angle from about 90° to about 135° and preferably either 135° or 90° with 90° being the most preferred to maximize the stopping function.

Finger slots 12 are formed between and defined by collet fingers 4 and function as egress ports for sutures threaded through the components of a suture clip loaded into the collet cage. Preferably, collet fingers 4 are biased in an open position so that radial force need only be applied to move the fingers from an open, suture clip loading/releasing position to a closed, suture clip confining position. Alternatively, finger collets 4 can be biased in a closed position.

Formed on an inner wall and toward the proximal end of collet fingers 4 are ramps 16 that taper radially inwardly from proximal to distal ends. Ramps 16 function as cam surfaces that when engaged with a pusher, as described below, cause collet fingers 4 to open. The distance between a proximal face of collet finger flanges 6 and the most distal point of ramps 16 is set to accommodate at least one set of unassembled suture clip components. This distance can be modified to receive the components for multiple suture clips.

Situated within a hollow chamber defined by the inner walls of collet cage 2 is an outer pusher 20 that freely slides within collet cage 2. Pusher 20 is preferably a hollow cylinder. A distal end 22 of outer pusher 20 is formed with a taper on the outside wall of pusher 20 that preferably conforms to and mates with the angle formed by ramp 16. Distal advancement of outer pusher 20 engages pusher distal end 22 with ramp 16. As outer pusher 20 slides distally along ramp 16, collet finger 4 is forced open. Outer pusher 20 can be used with either a collet finger that is biased in a closed position or an open position.

Situated within the hollow chamber formed by the walls of outer pusher 20 is cylindrically shaped inner pusher 24. Inner pusher 24 slides freely within outer pusher 20. Inner pusher 24 is designed to engage a head of a suture plug situated in the collet cage. Distal advancement of inner pusher 24 engages the suture plug and drives the suture plug distally into a suture clip ring. Collet finger flanges 6 function as a stop for the suture ring so that the distal axial force applied causes engagement of the suture clip components.

An inner pusher bore 26 is formed in inner pusher 24 and extends from a point proximal to the distal end of inner pusher 24 proximally through and out a proximal end of inner pusher 24. Inner pusher bore 26 provides a chamber for receiving a wire (not shown) that is used to apply axial force to inner pusher 24. Use of a wire provides adequate force to accomplish suture clip assembly and allows for flexibility over the length of the catheter.

Situated in coaxial relationship with and freely sliding about collet cage 2 is outer sliding sleeve 30 that performs at least two functions; providing radial force against collet fingers 4 to maintain the fingers in a closed position during suture clip delivery to a tissue site to minimize potential trauma that could be caused by open collet fingers and providing a means to sever the tail ends of a suture that has been secured with a suture clip. When advanced distally, sliding sleeve 30 encompasses collet fingers 4 and restricts radial movement of the fingers regardless whether the fingers are biased in an open or closed position. In this position, sliding sleeve 30 prevents outer pusher 20 from prematurely opening the collect.

When proximally retracted, sliding sleeve 30 severs directly or cooperates with other components to sever suture material proximal to a cinched suture clip. In one embodiment, a distal end of suture slot 34 engages the suture and carries it toward a distal end of the body of collet cage 2. When the distal end of suture slot 34 travels past the distal end of the body of collet cage 2, the suture is severed. In another embodiment, sliding sleeve 34 interacts with a fixed cutter 42, described below, to sever the suture tail ends.

At least one suture slot 34 is formed toward a distal end 32 of sliding sleeve 30 to provide egress for excess suture material that typically extends beyond the orifice through which the catheter is inserted. It is important that finger slots 12 and suture slots 34 are at least partially aligned to allow a path for excess suture material to exit the suture clip delivery device. To accomplish alignment, an alignment slot 36 is formed preferably near a proximal end of sliding sleeve 30. An alignment pin 40 is affixed to collet cage 2 and dimensioned to freely slide within alignment slot 36. The length of alignment slot 36 limits the proximal and distal travel of sliding sleeve 30. Alignment pin 40 is positioned on collet cage 2 and alignment slot 36 is positioned in sliding sleeve 30 such that at least one finger slot 12 and suture slot 34 are aligned along their longitudinal axes. Preferably two diametrically opposed sets of finger slots 12 and suture slots 34 are provided to allow egress for each end of a suture.

An optional feature of the presently described embodiment is a fixed cutter 42. Cutter 42 is preferably a metallic ring formed about and affixed to collet 2 that has a distal edge 44 that is sufficiently sharp to sever suture material. The ring is used for embodiments that are preferably injection molded. However, the use of filled or engineered plastics can be used to obviate the need for fixed cutter 42.

For the double pusher embodiment, a pistol grip control handle, well known in the art, is used to manipulate the various sliding components of the catheter. As shown in FIG. 139, pistol grip control 50 has three control surfaces for advancing and retracting the inner pusher 24, the outer pusher 20 and the outer sliding sleeve 30. A first control knob 52 and a second control knob 54 are coaxially arranged at a proximal end of pistol grip 50 and operate inner pusher 24 and outer pusher 20, respectively. A third control knob 56 extends from a top surface of, and in the distal end of, pistol grip 50. Third control knob 56 is connected to and operates outer sliding sleeve 30.

The first control knob 52 is connected to inner pusher 24 via a wire (not shown) that is preferably 0.030 inches in diameter and that fits within and frictionally engages the walls defining inner pusher bore 26. The second control knob 54 is connected to outer pusher 20 via a first hypotube (not shown) coaxially arranged about the inner pusher wire and that is preferably 0.042 inches in diameter. The pistol grip control 50 is attached to the catheter distal end 1 (the collect cage assembly) by a second hypotube 3 that is preferably 0.050 inches in diameter and coaxially arranged about the first hypotube. The third control knob 56 is attached to sliding sleeve 30 via a third hypotube (not shown) that is preferably about 0.065 inches in diameter and coaxially arranged about the second hypotube. Bushings between the hypotubes are provided in the collet cage assembly to seal the assembly and do not form a part of the invention. Preferably, the outer diameter of the catheter distal end 1 is 0.067 inches when all the components are assembled. This ensures a wide application of use for the invention.

To load suture clip components in the double pusher embodiment, first control knob 52 and third control knob 56 are placed in proximally retracted positions. If collet fingers 4 are biased in an open position, second control knob 54 can also be placed in a proximally retracted position. Otherwise, second control knob 54 is placed in a distally advanced position to open collet fingers 4 by causing distal end 22 of outer pusher 20 to engage ramps 16.

With collet fingers 4 arranged in an open position, ends of a suture 80 that has been used to stitch tissue in the internal regions of an individual are threaded through a suture clip ring and into thread apertures formed in a suture clip plug. The suture ends are then fed through either the same or separate sets of finger slots 12 and suture slots 34 so that the ends of the suture are arranged external to the suture clip delivery catheter. The suture clip plug is then placed in a proximal end of the collet cage and the suture clip ring is placed in a distal end of the collet cage where the ring preferably engages at least one of the collet finger flanges 6 to prohibit distal travel of the ring. It is to be understood that the collet cage can be sized to accommodate a plurality of suture clip plugs that can be stacked for deployment into suture clip rings that must be loaded one per suture clipping procedure.

As shown in FIGS. 140 and 141, with the suture clip components loaded, second control knob 54 is retracted if previously advanced, and third control knob 56 is distally advanced so that outer sliding sleeve 30 engages and applies a radially constraining force to collet fingers 4 to maintain the fingers in a closed position during insertion of the catheter into a patient. In this configuration, catheter distal end 1 is advanced to the suture-clipping site in a patient.

To operate the double pusher embodiment, first control knob 52 is distally advanced so that inner pusher 24 engages the suture clip plug and forces a distal shaft of the plug into the suture clip ring. The frictional engagement of the suture clip plug to the suture clip ring captures the suture 80 via frictional engagement as shown in FIG. 142. The advancement of inner pusher 24 also causes the suture clip components to be cinched in close proximity to the stitched tissue. Once the plug has been secured to the ring and the assembled suture clip cinched to the stitched tissue, third control knob 56 is retracted to release the radial force applied to the collet fingers 4 by sliding sleeve 30. The proximal retraction of sliding sleeve 30 also causes a distal end of suture slot 34 to engage suture 80 and carry it proximally toward either the sharp distal end of the collet cage 2 or the distal edge 44 of fixed cutter 42 as shown in FIG. 143. When the distal end of suture slot 34 passes proximally beyond either the distal end of the collet body or distal edge 44, the suture is severed proximal to the assembled clip as shown in FIG. 144. The severed ends of the suture can then be pulled out of the individual.

If collet fingers 4 are biased in a closed position, second control knob 54 is distally advanced to ramp open the collet fingers to release the assembled plug as shown in FIG. 145. Once the suture clip has been released as shown in FIG. 146, second control knob 54 is retracted and third control knob 56 is advanced to place collet fingers 4 in a closed position to reduce the potential for trauma when the catheter is removed from the individual.

In an alternate embodiment, outer pusher 20 is eliminated as shown in FIG. 147. Optional fixed cutter 44 is also not present in FIG. 147. In this alternate embodiment, collet cage 2, outer sliding sleeve 30 and inner pusher 24 are configured the same as with the double pusher embodiment. Ramps 16 formed on the inner walls of the collet fingers can be eliminated. To ramp open the collet fingers, the proximal surfaces of the collet finger flanges 6 are preferably provided with a taper that increases radially inwardly from a proximal to a distal end and that preferably forms an inclusive angle with the body of the associated collet finger of preferably from about 128° to about 135° to perform the cam function of ramps 16. Like the double pusher embodiment, sliding sleeve 34 is maintained in a distally advanced position to radially constrain collet fingers 4 while inner pusher 24 is distally advanced to secure the suture clip components and cinch the assembled suture clip to the stitched tissue.

When inner pusher 24 is proximally advanced, a distal edge of the suture clip ring engages the beveled surfaces of collet finger flanges 6 the combination of which generates a ramp opening force against the constrained collet fingers 4. Proximal retraction of sliding sleeve 30 allows finger collets 4 to return to their pre-biased open positions and severs the ends of the suture in the same manner as with the double pusher embodiment. The ramp opening force generated by inner pusher 24 can aid the opening process and facilitate release of the assembled suture clip. As with the double pusher version, sliding sleeve 30 is again distally advanced to constrain collet fingers 4 for removal of the catheter from the individual. Essentially, eliminations of outer pusher 20 reduces the three-step process of the double pusher embodiment to the two-step process of the single pusher embodiment.

Another embodiment of the single pusher system employs ramps 16 with or without the tapered collet finger flanges 6. In this embodiment, the collet cage assembly is used with a suture clip that is comprised of a ring 60 and a plug 62 having a head 64 with a chamfered edge 66, as shown in FIG. 148, that engages and mates with ramps 16 to ramp open finger collets 4 when the plug is distally advanced. This configuration is applied particularly with collet fingers that are biased in a closed position.

In a further collet cage assembly embodiment, the need for resilient collet fingers is eliminated as shown in FIGS. 165-171. Referring to FIGS. 165, 166, 168 and 172, collet cage 2 has a collet cage body 2a with axially oriented finger slots 2b(shown in FIGS. 170 and 171), dimensioned to receive pivot collet fingers 4a. Formed in a sidewall of collet cage body 2a are collet pin apertures 4d (shown in FIGS. 170 and 171), adapted to receive collet finger pin 4c. Collet pin apertures 4d are formed on either side of each finger slot 2a and are aligned in pairs to receive rod-shaped collet finger pin 4c. Formed in the bodies of pivot collet fingers 4a are finger apertures 4e also adapted to receive collet finger pin 4c. Pin 4c is secured within collet pin apertures 4d via friction fit, adhesive or mechanical manipulation of pin 4c to cause the cold flow of material at the ends of pin 4c. The materials used for collet cage body 2a and collet fingers 4a described herein provide sufficient lubricity to allow for the free rotation of collet fingers 4a about pin 4c.

Pivot collet fingers 4a have the same distal finger flanges 6 with beveled inner surfaces to provide a temporary axial stop for the suture clip components as described for the resilient collet finger embodiments. Collet fingers 4a have proximal ends 4f dimensioned so that shortest distance between two opposing collet fingers 4a is a dimension D. The transition between proximal ends 4f and the main body of fingers 4a forms a shoulder 4b positioned proximal to the point of connection to pin 4c. In this configuration, collet fingers 4a act as dogs that are radially constrained in a position parallel to a central longitudinal axis of collet cage body 2a via a temporary radial constraint. A radially extended distal end of pusher 24, plug head 64, plug 62 in headless embodiments, or other components can act as the source of the radial constraint by virtue of having diameters that are just slightly less than distance D.

Restraint is accomplished, as shown in FIG. 165, when the restraining component (plug head 64 in FIG. 165), is positioned to contact collet finger proximal ends 4f in a pre-cinched condition. Once the restraining component is advanced distally past proximal ends 4f, as shown in FIG. 167, the suture clip components, i.e., plug 62 and ring 60, are cinched and collet fingers flanges 6 are free to rotate radially outwardly to release the cinched suture clip. As with other previously described embodiments, the same distal advancement of pusher 24 causes a suture (not shown) to be severed proximal to the suture clip components. With the pivoting collet fingers, sliding sleeve 30 can be eliminated, if desired, because radial restraint is provided internally.

Shown in FIG. 169 is an alternate embodiment of the pivoting collet finger design that eliminates the need for pin 4c and any potential problems with wall thickness and removal of cross-sectional area inherent when forming finger apertures 4e in pivot collet fingers 4a. A pivot ring 30a is secured to the exterior of collet cage body 2a at a point along the length of pivot collet fingers 4a. As with the previously described embodiment, radial constraint is provided by pusher 24, plug 62 or by some other component when the system is in a pre-cinched condition. Once the constraining component is advanced distally past collet finger proximal ends 4f, pivot collet fingers 4a pivot about a distal edge 30b of pivot ring 30a such that collet finger flanges 6 rotate radially outwardly to allow the release of the cinched suture clip components.

In a preferred embodiment of the single pusher system, the entire collet cage 2 is miniaturized to allow for collet cage 2 and the attached hypotubes to fit within the working channel of an endoscope. The miniaturized collet cage 2 and a control handle 90 for the collet cage are shown in FIGS. 157, 163 and 164. Preferably, the outer diameter of collet cage 2 is about 0.094 inches and the length is about 0.42 inches to easily accommodate the space available in the working channel of an endoscope (typically between about 0.110 and 0.115 inches) and more particularly to enable negotiation of the 45° bifurcation that is typically located toward the distal end of an endoscope.

Collet cage 2 is connected to control handle 90 via a collet cage hypotube 3. Preferably, hypotube 3 is laser welded to collet cage 2. A proximal end of collet cage hypotube 3 is attached to a collet cage handle bushing 100. Bushing 100 is used to allow for laser welding of hypotube 3 to a collet cage handle 98. Collet cage handle 98 performs the function of orienting the axial relationship of collet cage 2 to the two axially moving components, sliding sleeve 30 and pusher rod 94 (pusher 24). Situated about collet cage hypotube 3 is sliding sleeve hypotube 3a. A distal end of hypotube 3a is attached via laser welding to sliding sleeve 30 and a proximal end is attached to a sliding sleeve bushing 104. This enables hypotube 3a to be laser welded to a sliding sleeve handle 102. Sliding sleeve handle 102 is used to control axial movement of sliding sleeve 30 relative to collet cage 2. To increase the lubricity of the system for ease of delivery through an endoscope, an outer sheath 3b (preferably made from polyether-blockamide tubing, white (2% $TiO_2$)) is adhered to sliding sleeve hypotube 3a with an adhesive such as Tra-Bond® #FDA-2 epoxy.

Provided within collet cage hypotube 3 is pusher rod 94. As described above, pusher rod 94 (inner rod 24 in other embodiments) is used to cinch plug 62 into ring 60. A proximal end of pusher rod 94 is secured to an interior bore of a cinch handle insert 96 via pins or screws 107 and helicoils 108 shown in FIG. 158. An exterior surface of cinch handle insert 96 is secured via pins or screws (not shown) to cinch handle 92.

The preferred materials used to make the various collet cage 2 and control handle 90 components are as follows. Collet cage 2, sliding cutter sleeve 30, alignment pin 40, inner rod 24, sliding sleeve bushing 104, cage handle bushing 100 and cinch handle insert 96 are made from either 304L or 316L stainless steel. Pusher rod 94, collet cage hypotube 3 and sliding sleeve hypotube 3a are made from 304 stainless steel. Sliding sleeve handle 102, collet cage handle 98 and cinch handle 92 are made from Delrin®. To enhance the distinction among the three handles, each can be made from a different color of Delrin®. For example, sliding sleeve handle 102 can be red, collet cage handle 98 can be white and cinch handle 92 can be black.

In an alternate embodiment shown in FIG. 158, control handle 90 can be provided with springs to ensure that the proper orientation of the moving parts is maintained before and after the delivery and cinching of the suture clip components. First return spring 105 provides an axial force that maintains pusher rod 94 in a proximal position while second return spring 106 provides an axial force that maintains sliding cutter sleeve 30 in a distal position. The springs are selected to provide enough tension to maintain the pusher rod and sliding cutter sleeve in starting positions when advancing and retracting the suture clip delivery device. This provides desired protection to an endoscope that could potentially be damaged if collet fingers 4 where allowed to remain in radially extended positions when advancing or retracting the delivery device in the endoscope. The springs are further selected so that the manual forces needed to overcome the springs to advance pusher rod 94 and to retract sliding cutter sleeve 30 are within acceptable ranges.

In a further embodiment shown in FIGS. 159-162, a control handle 90' provides a means of cinching the suture clip components, releasing the cinched suture clip and severing the suture tails with a single action. In this embodiment, a handle main body 90a extends distally and terminates as collet cage 2. An outer handle sleeve 90b is provided about main body 90a, extends distally and terminates as sliding sleeve 30. To secure plug 62 into ring 60, a distally directed force is applied to cinch handle 92' to overcome the force of second return spring 106 which has an axial pre-bias load in tension. Distal advancement of cinch handle 92 relative to handle main body 90a causes second return spring 106 to engage a proximal end of a ramrod 94a and cause the distal advancement of ramrod 94a into a proximal end of pusher 94. Distal advancement of pusher 94 causes engagement and distal advancement of plug 62. Second return spring 106 is of sufficient resiliency to resist compression while moving ramrod 94a distally to effectuate the insertion of plug 62 into ring 60.

A restraining force to hold outer handle sleeve 90b and sliding sleeve 30 in a stationary position relative to advancing ramrod 94a and cinch handle 92 is provided by a user's fingers engaged in finger rings 5a, mounted to a proximal end of outer handle sleeve 90b. Spring plunger 30a provided at the proximal end of outer handle sleeve 90b, engages cutout 30b formed in handle main body 90a to temporarily lock outer handle sleeve 90b and main body 90a together during distal advancement of ramrod 94a. Spring plunger 30a, biased in a radially extended position by a plunger spring 30d, remains extended and in a locked position with respect to main body 90a. Plunger spring 30d have an axial pre-bias load in tension. Spring plunger 30a may be compressed only when the distal angular face 16a of cinch handle 92 has advanced distally to a point of tangency with angular face 19 of spring plungers 30a. Distal movement of the distal angular face 16 drives spring plunger 30a in a direction perpendicular to the central axis, a distance equivalent to the thickness 20a of the wall of cinch handle 92. At this point, the restraining forces provided by the user's fingers (in a proximal direction), acting on main body 90a through finger rings 5a, have been restrained. The locking action of spring plunger 30a is an interaction of a radial surface 22a with pusher face 21. Alignment of angular face 19 with angular pusher face 21 results in continued radial outward motion of spring plunger 30a with the continued distal motion of main body 90a.

Main body 90a continues distally with the application of palm pressure on cinch handle 92 and the relative opposite motion of finger rings 5a (proximally). Suture 80 (not shown), lying in a path of sliding sleeve 30 is severed with the proximal travel of sliding sleeve 30. Collet fingers 4 are now unrestrained and assume their biased open position releasing cinched plug 62 and ring 60.

In the most retracted stage of sliding sleeve 30 and finger rings 5a, a second spring plunger 23 drops into a second cutout 30c. Second spring plunger 23 is maintained in a compressed state via second plunger spring 30e. Second plunger spring 30e has an axial pre-bias load in compression. Second spring plunger 23 remains in second cutout 30c only with the application of a force by the user's thumb on the most outward end of second spring plunger 23. This temporary locking feature is provided to maintain sliding sleeve 30 in its most proximal position to allow for loading of plug 62 and ring 60 as described in detail herein. Release of the holding pressure automatically releases sliding sleeve 30 to affect a closure of the delivery system.

To operate this embodiment of the suture clip delivery system, following the loading of a suture clip assembly and the threading of sutures through ring 60 described below, the entire delivery device is advanced through the endoscope to the sutured tissue site. Next, cinch handle 92 is advanced toward collet cage handle 98 to cinch plug 62 into ring 60 so that suture 80 is captured between the mating surfaces of a plug distal shaft 68 and the inner walls of ring 60. Following completion of the cinching step, sliding sleeve handle 102 is retracted toward collet cage handle 98 to simultaneously sever the unused ends of suture 80 and to allow collet fingers 4 to spring open and release the suture clip assembly. To complete the procedure, the suture clip delivery system is partially retracted so that the suture clip is clear of the delivery system distal end. Prior to full retraction, sliding sleeve handle 102 is advanced to move collet fingers 4 into a closed position to allow for the full retraction of the suture clip delivery system out of the endoscope. With the spring embodiment of the handle (FIG. 164), release of the users' grip on sliding sleeve handle 102 allows first return spring 105 to relax thereby advancing sliding sleeve handle 102 and sliding cutter sleeve 30 to a preferably fully advanced position.

The suture clips used with the suture clip delivery catheter and/or endoscopic system described herein, have plugs with heads. In another embodiment as shown in FIG. 149, plug 62 has distal shaft 68 that is adapted to frictionally engage the inner walls of ring 60 and a head 64 that has preferably two suture receiving bores 70 formed toward the perimeter of the head 64. This configuration provides a suture clip plug that decreases the effort needed to advance the plug over the ends of a suture before loading into the suture clip delivery device.

In a preferred embodiment shown in FIGS. 150-152, the inner and outer walls of ring 60 are radiused at the ends 74 to facilitate the insertion of distal shaft 68 into ring 60. More importantly, the radiused ends provide strain relief for the sutures 80 when compressed between the plug 62 and ring 60. To further facilitate insertion, distal shaft 68 is formed with a tapered distal tip 72. Alternatively, a reduced neck distal tip 72a can be employed as shown in FIG. 153. Although interlocking features can be incorporated into the plug and clip components, it has been found that such features can lead to suture fraying, premature fracturing and failure. Use of tapered or reduced tipped plugs 62 allow for a preferred gradual reduction in compression. It has been found that suture capture is optimized and suture destruction is minimized when a distally decreasing taper leading end is used on plug 62 with a proximally increasing diameter of plug 62 to exceed the net diameter of the suture 80 in a captured state plus the diameter of plug 62 by at least 0.002 inches. The preferred materials used to make plug 62 and ring 60 are polyetherether ketone (PEEK) 450G, PEEK-Optima™ LT or polyethylene terephthalate (PET).

As previously stated, suture 80 is held via friction between plug 62 and ring 60. For example, a 0.009 inch thick suture is captured in a 0.003 inch gap between plug 62 and ring 60 so that the suture will remain captured with the application of a three pound load. The aforementioned radiused and tapered surfaces of plug 62 and ring 60 provide enough strain relief to prevent damage to suture 80 when subjected to the three-pound load.

A further suture clip embodiment employs a head with a proximal surface that is convex as shown in FIG. 148. Preferably, the distal end of inner pusher 24 is provided with a concave surface to matingly engage the convex surface of plug head. This configuration aids with the axial alignment of the ring and plug during distal advancement and engagement.

To load the suture clip assembly into collet cage 2, a suture clip loader device 110 is provided as shown in FIGS. 154-156. Loader device 110 comprises a loader housing 112 that is substantially cylindrical in shape and a plunger 114 that is also substantially cylindrical in shape. Loader housing 112 has a collet cavity 116 formed in a first end 118 that is dimensioned to receive collet cage 2. Collet cavity 116 has a cavity end 120 tapered to facilitate insertion of collet cage 2. Formed on diametrically opposed surfaces of a sidewall of loader housing 112 are finger grooves 122 that provide a stable holding surface for manipulating loader housing 112 during a suture clip loading procedure. A loader hypotube 124 is secured with an adhesive 126 (preferably cyanoacrylate Loctite® 4013 or 4014) to a loader hypotube shoulder 123 and a bore formed along the longitudinal axis of loader housing 112. Loader hypotube 124 extends from a second end 130 of loader housing 112 to at least partially within collet cavity 116 and is dimensioned to receive at a distal hypotube end 125, the tapered distal tip 72 of plug 62. A transverse groove 128 is formed proximal to second end 130 of loader housing 112. The function of groove 128 will be discussed below.

Plunger 114 comprises a plunger head 132 and a plunger rod 134 secured via friction fit or adhesive in a bore formed along a longitudinal axis of plunger head 132. Plunger rod 134 is sized to freely slide within hypotube 124. Extending from a first plunger end 136 of plunger head 132 is tab 138. A top surface of tab 138 is contoured like, and coplanar with, the outer surface of plunger head 132 while a bottom surface is substantially flat and oriented substantially perpendicular to first plunger end 136. Extending downwardly from a distal end of tab 138 is a flange 140 that is shaped to conform to the shape of groove 128. Optionally, plunger head 132 can be formed with a radiused second plunger end 142 for ease of handling.

The cross-sectional diameter of plunger head 132 is sized so that the distance between the bottom surface of tab 138 and the most distant point on the cross-sectional circumference of plunger head 132 is substantially equal to the cross-sectional diameter of loader housing 112. When plunger rod 134 is inserted into hypotube 124, the bottom surface of tab 138 rides along the outer surface of loader housing 112. Because flange 140 extends below the bottom surface of tab 138, advancement of plunger 114 toward loader housing 112 results in flange 140 engaging groove 128 and temporarily locking in the distance between plunger 114 and loader housing 112. In this orientation, a distal end of plunger rod 134 does not reach distal hypotube end 125 so that plug 62 can be received in hypotube end 125.

The preferred materials for the suture clip loader device 110 components are as follows. Plunger head 132 is made from Delrin® and is preferably white. Plunger rod 134 is made from 304V stainless steel. Loader hypotube shoulder 123 is made from 304 stainless steel. Loader housing is made from polycarbonate GE Lexan® 104-1111 and is preferably clear to allow for an unobstructed view of hypotube end 125. Hypotube 124 is made from polyetherether ketone (PEEK) 450G.

The operation of suture clip loader device 110 is as follows. The process begins by placing ring 60 over hypotube 124. Next, the distal tip 72 of plug 62 is inserted into hypotube end 125 until it is snugly secured to hypotube 124. At this point, plunger 114 is secured to loader housing 112 via the engagement of flange 140 to groove 128.

With collet cage 2 extending from the distal end of an endoscope, sliding sleeve 30 is retracted to allow collet fingers 4 to spring into an open position. Collet cage 2 is advanced over hypotube 124 and ring 60 until the distal end of collet cage 2 engages a bottom of collet cavity 116. Once the suture clip components have been correctly encapsulated by collet fingers 4, force is applied to plunger 114 to overcome the locking engagement of flange 140 and groove 128. This enables plunger rod 134 to be advanced through hypotube 124 to contact and eject plug 62 into collet cage 2. Proper ejection is assured when first plunger end 136 contacts second end 130 of loader housing 112. To capture ring 60 within collet cage 2, sliding sleeve 30 is advanced to move collet fingers 4 into a closed position about ring 60 and hypotube 124. Collet finger flanges 6 engage a distal face of ring 60 so that retraction of collet cage 2 from hypotube 124 results in ring 60 being retracted off hypotube 124 and secured within the distal end of collet cage 2.

It is important that plug 62 is maintained in the proximal end of collet cage 2 and that ring 60 is maintained in the distal end of collet cage 2. This is required to enable suture 80 to be threaded through ring 60 prior to cinching and final deployment of the suture clip assembly.

The next step in the procedure is to thread sutures previously secured to tissue through ring 60. To perform this procedure, a threader or suture loop tool 150 is used. As shown in FIGS. 173-175, threader 150 comprises a threader housing 152 that is substantially cylindrical in shape and preferably made from polycarbonate GE Lexan® 104-1111. Formed on diametrically opposed surfaces of a sidewall of threader housing 152 are threader finger grooves 160 that provide a stable holding surface for manipulating threader housing 152 during a suture threading procedure. Affixed to a bore formed along the longitudinal axis of threader housing 152 is suture loop hypotube 154. An adhesive 158 such as cyanoacrylate Loctite® 4013 (clear) is used to secure suture loop hypotube 154 (preferably made from 304 stainless steel), to threader housing 152. A suture loop 156 preferably made of two thin 304v stainless steel wires is secured inside suture loop hypotube 154 and extends beyond a distal end 162 of suture loop hypotube 154. A suture loop distal end 164 is formed into a diamond shape by overlapping the stainless steel wires. Preferably, a tip of the suture loop distal end is formed by overlapping the wires at least twice.

To thread suture 80 through ring 60, suture loop 156 of threader 150 is inserted into suture slot 34 of sliding sleeve 30, advanced through ring 60 and through the distal end of collet cage 2. Suture 80 is inserted into the diamond-shaped suture loop distal end so that it engages and preferably becomes entangled with the intertwined distal tip of suture loop distal end 164. To thread suture 80 through ring 60, threader 150 is retracted out of suture slot 34. Suture 80 is then removed from threader 150. The suture clip assembly is now ready for cinching and deployment as described above.

In an alternate embodiment, threader 150 comprises a vacuum-actuated nozzle 150' made from a pliable polymeric or elastomeric material. As shown in FIGS. 176 and 177, a nozzle head 170 is formed at the end of a vacuum hose 168 and adapted to conform to the contoured shape of collet cage 2. A proximal end of vacuum hose 168 (not shown) is attached to a vacuum source (not shown). In a further embodiment shown in FIGS. 178 and 179, nozzle head 170 is formed with nozzle ears 170' that preferably extend about and beyond collet cage 2 to enhance the ease with which the nozzle head can be secured against suture slot 34, again with either finger or forceps pressure.

To operate nozzle 150', nozzle head 170 is maintained against suture slot 34 with either finger pressure or pressure exerted with forceps while a vacuum is applied. The vacuum draws suture 80 through ring 60 and out of collet cage 2 via suture slot 34. The vacuum is then released, nozzle head 170 is removed from collet cage 2 and suture 80 is grasped and pulled a desired amount through ring 60 and collet cage 2.

It should be understood that the foregoing description of the invention is intended merely to be illustrative thereof and that other modifications, embodiments and equivalents may be apparent to those who are skilled in the art without departing from its spirit.

Having thus described the invention what we desire to claim and secure by Letters Patent is:

1. A non-locking suture clip comprising:
   a plug that is adapted to be implanted within a human body, the plug having a head and a shaft extending distally from the head, the shaft having a first diameter and the head having a shoulder with a second diameter greater than the first diameter, the shaft having a tapered distal end that tapers inwardly in a direction extending away from the head; and a ring that is adapted to be implanted within the human body, the ring being continuous and having an inner annular wall defining a through aperture extending from a proximal end to a distal end of the ring, the through aperture having an aperture diameter greater than the first diameter and less than the second diameter, the shoulder adapted to contact an end of the ring to prevent insertion of the head into the through aperture, wherein an axial vacancy is located between the shaft and the annular wall when the shaft is inserted into the through aperture and the shoulder contacts the end of the ring, the axial vacancy adapted to receive a suture therein, the plug and the ring having a non-locking arrangement wherein the plug and the ring do not lock together when the shaft is inserted into the through aperture without the suture located in the axial vacancy.

2. The suture clip of claim 1 wherein the axial vacancy is at least about 0.003 inches.

3. The suture clip of claim 1 wherein the axial vacancy is no greater than about 0.003 inches.

4. The suture clip of claim 1 further comprising a suture situated between the plug shaft and the ring wherein the suture has a diameter greater than the axial vacancy.

5. The suture clip of claim 1, wherein:
the ring comprises one or more ring suture apertures extending through the ring from the proximal end to the distal end of the ring, each ring suture aperture configured to receive a suture; and
the plug has one or more plug suture apertures extending through the plug from the proximal end to the distal end of the plug, each plug suture aperture configured to receive a suture.

6. The suture clip of claim 5, wherein the ring comprises two ring suture apertures positioned oppositely from each other.

7. A non-locking suture clip comprising:
a plug that is adapted to be implanted within a human body, the plug having a head and a shaft extending distally from the head, the shaft having a first diameter and the head having a shoulder with a second diameter greater than the first diameter, the shaft having a reduced neck distal end; and
a ring that is adapted to be implanted within the human body, the ring being continuous and having an inner annular wall defining a through aperture extending from a proximal end to a distal end of the ring, the through aperture having an aperture diameter greater than the first diameter and less than the second diameter, the shoulder adapted to contact an end of the ring to prevent insertion of the head into the through aperture, wherein an axial vacancy is located between the shaft and the annular wall when the shaft is inserted into the through aperture and the shoulder contacts the end of the ring, the axial vacancy adapted to receive a suture therein, the plug and the ring having a non-locking arrangement wherein the plug and the ring do not lock together when the shaft is inserted into the through aperture without the suture located in the axial vacancy.

8. A non-locking suture clip comprising:
a plug that is adapted to be implanted within a human body, the plug having a head and a shaft extending distally from the head, the shaft having a first diameter and the head having a shoulder with a second diameter greater than the first diameter; and
a ring that is adapted to be implanted within the human body, the ring being continuous and having an outer wall and an inner annular wall defining a through aperture extending in a longitudinal direction from a proximal end to a distal end of the ring, the through aperture having an aperture diameter greater than the first diameter and less than the second diameter, the shoulder adapted to contact an end of the ring to prevent insertion of the head into the through aperture, wherein an axial vacancy is located between the shaft and the annular wall when the shaft is inserted into the through aperture and the shoulder contacts the end of the ring, the axial vacancy adapted to receive a suture therein, the plug and the ring having a non-locking arrangement wherein the plug and the ring do not lock together when the shaft is inserted into the through aperture without the suture located in the axial vacancy, the ring including one or more ring suture apertures located between the outer wall and the inner wall, each ring suture aperture extending through the ring in the longitudinal direction from the proximal end to the distal end of the ring, each ring suture aperture configured to receive a suture.

9. The suture clip of claim 8, wherein the ring comprises two ring suture apertures positioned oppositely from each other.

10. The suture clip of claim 8, wherein the plug has one or more plug suture apertures extending through the plug from the proximal end to the distal end of the plug, each plug suture aperture configured to a receive suture.

11. The suture clip of claim 10, wherein the plug has a single plug suture aperture located in the radial center of the plug.

12. The suture clip of claim 10, wherein the plug has two plug suture apertures, located oppositely from each other and near the radial edge of the head of the plug.

* * * * *

UNITED STATES PATENT AND TRADEMARK OFFICE
CERTIFICATE OF CORRECTION

| | | |
|---|---|---|
| PATENT NO. | : 7,993,368 B2 | Page 1 of 1 |
| APPLICATION NO. | : 10/220413 | |
| DATED | : August 9, 2011 | |
| INVENTOR(S) | : Richard A. Gambale et al. | |

It is certified that error appears in the above-identified patent and that said Letters Patent is hereby corrected as shown below:

At column 42, claim 10, line 44, replace "a receive suture" with -- receive a suture --.

Signed and Sealed this
Fourth Day of October, 2011

David J. Kappos
*Director of the United States Patent and Trademark Office*